(12) United States Patent
Shyur

(10) Patent No.: US 8,728,787 B2
(45) Date of Patent: May 20, 2014

(54) FUNGAL LACCASES AND USES THEREOF

(71) Applicant: Academia Sinica, Taipei (TW)

(72) Inventor: Lie-Fen Shyur, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 13/923,816

(22) Filed: Jun. 21, 2013

(65) Prior Publication Data

US 2013/0273631 A1  Oct. 17, 2013

Related U.S. Application Data

(62) Division of application No. 12/777,569, filed on May 11, 2010, now Pat. No. 8,492,131.

(51) Int. Cl.
| *C12N 9/02* | (2006.01) |
| *C12Q 1/26* | (2006.01) |
| *C07K 14/00* | (2006.01) |
| *C12P 21/00* | (2006.01) |

(52) U.S. Cl.
USPC .............. 435/189; 435/69.1; 435/25; 530/350

(58) Field of Classification Search
USPC ............................ 435/189, 25, 69.1; 530/350
See application file for complete search history.

(56) References Cited

FOREIGN PATENT DOCUMENTS

JP      2006-158252      6/2006

OTHER PUBLICATIONS

Branden et al., Introduction to Protein Structure, Garland Publishing Inc., New York, p. 247, 1991.
Seffernick et al., J. Bacteriol. 183(8):2405-2410, 2001.
Witkowski et al., Biochemistry 38:11643-11650, 1999.
Khammuang et al., "Laccase From Spent Mushroom Compost of *Lentinus polychrous* Lev, and its Potential for Remazol Brilliant Blue R Decolourisation," Biotechnology 6(3):408-413 (2007).
D'Annibale et al., "Substrate Specificity of Laccase from *Lentinus edodes*," Acta Biotechnol. 16(4):257-270 (1996).

*Primary Examiner* — Delia Ramirez
(74) *Attorney, Agent, or Firm* — Cesari and McKenna, LLP

(57) ABSTRACT

Novel laccases from *Cerrena* sp. WR1 and *Lentinus* sp. and uses thereof.

8 Claims, 13 Drawing Sheets

A.

B.

C.

D.

A.

B.

A.

B.

C.

A

B

FUNGAL LACCASES AND USES THEREOF

RELATED APPLICATION

This application is a division of U.S. application Ser. No. 12/777,569, filed on May 11, 2010, the content of which is incorporated herein by reference in its entirety.

BACKGROUND OF THE INVENTION

Laccases (benzenebiol:oxygen oxidoreductase; EC 1.10.3.2) are multi-copper-containing oxidases found in various organisms, e.g., insect, plant, and fungi.

They catalyze oxidation of a broad range of compounds, e.g., diphenol, polyphenol, diamine, and aromatic amine. Many of these compounds are important raw materials for making various industrial products. Others are toxic components contained in industrial wastes.

Laccases have great potential in industrial applications, such as biopulping, biobleaching, food processing, bioremediation, and wastewater treatment.

SUMMARY OF THE INVENTION

The present invention is based on an unexpected discovery that six novel laccases, three from *Cerrena* sp. WR1 (i.e., Lcc1, Lcc2, and Lcc3) and the other three from *Lentinus* sp. (LccA, LccB, and LccC), exhibit high laccase activity.

Accordingly, one aspect of this invention features an isolated polypeptide containing an amino acid sequence at least 85% (e.g., 90%, 95%, or 98%) identical to one of SEQ ID NOs: 1-6, referring to mature laccases Lcc1, Lcc2, Lcc3, LccA, LccB, and LccC, respectively. In one example, the isolated polypeptide has the amino acid sequence of one of SEQ ID NOs: 7-12, referring to precursor (i.e., including an N-terminal signal peptide) Lcc1, Lcc2, Lcc3, LccA, LccB, and LccC, respectively.

Another aspect of the invention features an isolated nucleic acid (e.g., an expression vector) containing a nucleotide sequence coding for one of the laccases mentioned above. In one example, the nucleotide sequence is one of SEQ ID NOs: 13-18, coding for SEQ ID NOs: 1-6, respectively. In another example, it is one of SEQ ID NOs: 19-24, coding for SEQ ID NOs: 7-12, respectively. Preferably, the nucleotide sequence is in operative linkage with a suitable promoter for expressing the encoded polypeptide in a host cell.

The terms "isolated polypeptide" and "isolated nucleic acid" used herein respectively refer to a polypeptide and a nucleic acid substantially free from naturally associated molecules. A preparation containing the polypeptide or nucleic acid is deemed as "an isolated polypeptide" or "an isolated nucleic acid" when the naturally associated molecules in the preparation constitute at most 20% by dry weight. Purity can be measured by any appropriate method, e.g., column chromatography, polyacrylamide gel electrophoresis, and HPLC.

Also within the scope of this invention is a method of oxidizing a laccase substrate (i.e., a compound that can be oxidized by a laccase) by contacting one of the laccases mentioned above with the substrate. In one example, the substrate is hardwood stem, softwood stem, nut shell, corn cob, paper (e.g., newspaper or waste paper from chemical pulps), straw (e.g., straw from rice, wheat, barley, oat, or rye), sorted refuse, leaf, cotton seeds hair, swine waste, cattle manure, grass (e.g., switch grass, Coastal Bermuda grass, S32 rye grass, Grass Esparto, Grass Sabai, Grass Elephant), sugar cane bagasse, bamboo, fiber (e.g., Bast fiber Seed flax, Bast fiber Kenaf, Bast fiber Jute, Leaf fiber Abaca, Leaf fiber Sisal, or Leaf fiber Henequen), coffee pulp, banana waste, and yucca waste. In another example, the substrate is an aromatic dye, such as a polyphenol-containing dye.

The details of one or more embodiments of the invention are set forth in the description below. Other features or advantages of the present invention will be apparent from the following drawings and detailed description of two examples, and also from the appended claims.

BRIEF DESCRIPTION OF THE DRAWINGS

The drawings are first described.

DETAILED DESCRIPTION OF THE INVENTION

Figure 1:
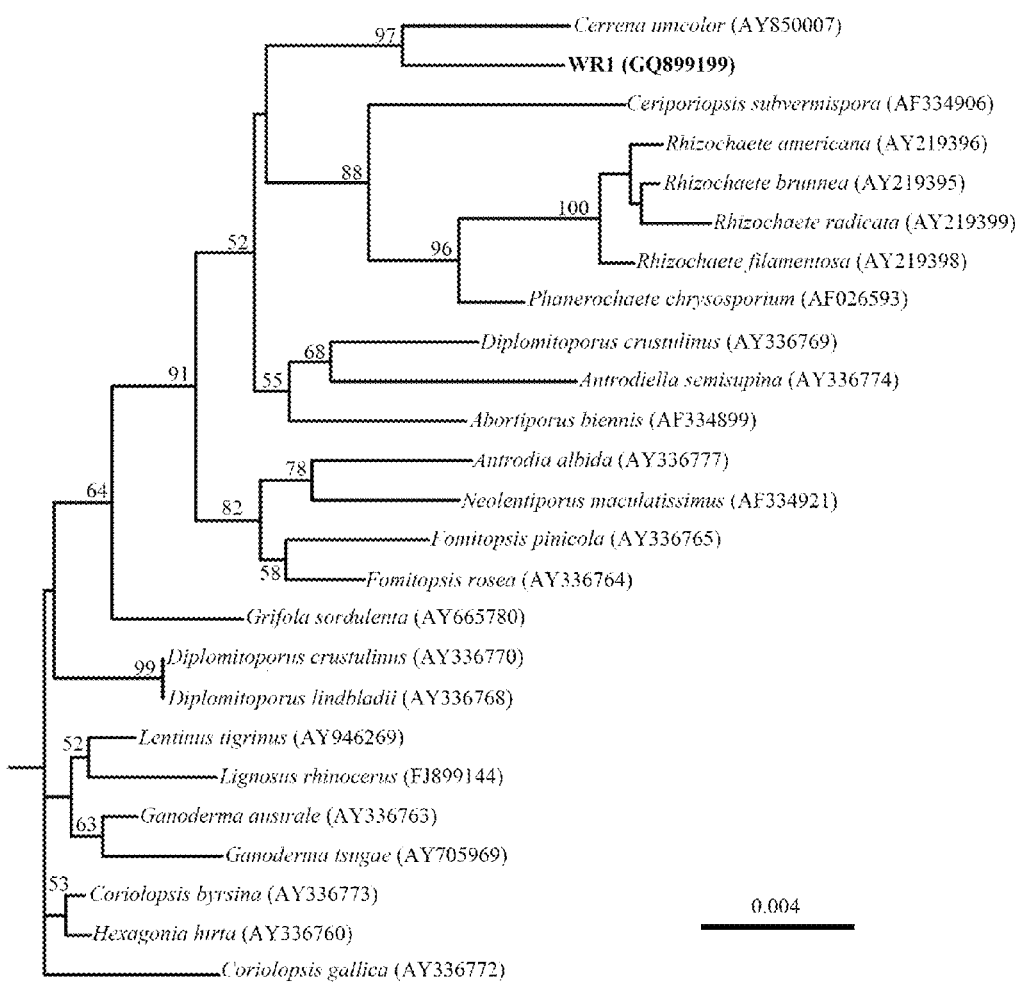
FIG. 1 is a diagram showing the phylogenetic relationship between *Cerrena* sp. WR1 and other fungal strains. Bootstrap values at nodes refer to the percentage of 500 replicates. Scale bar: base substitutions per 100 bases.

Described below are laccases Lcc1, Lcc2, and Lcc3, isolated from *Cerrena* sp. WR1, and laccases LccA, LccB, and LccC, isolated from *Lentinus* sp. The amino acid sequences of these enzymes, in precursor form, and their coding sequences are shown below.

Cerrena sp. WR1 Lcc1 (GenBank accession no. GQ899201)

```
ATGCTTAACTTTAATTCGCTTTCCACCTTCGCAGTCCTTGCTTTGTCGATGCGCGCAAATGCCGCTATCGGTCCTGTCACTGACTTAGAA    30
 M   L   N   F   N   S   L   S   T   F   A   V   L   A   L   S   M   R   A   N   A  A  I  G  P  V  T  D  L  E

ATCACGAACGGCACCATCTCTCCCGATGGCTATTCTCGTGCAGCCGTCCTTGCTGGAGGCTCTTTCCCCGGCCCACTTATCACAGGAAAC    60
 I  T  N  G  T  I  S  P  D  G  Y  S  R  A  A  V  L  A  G  G  S  F  P  G  P  L  I  T  G  N
                                                                                        Cu²⁺ binding site-I
AAAAGTGACAACTTCCAAATCAACGTTGTGAACTCGTTGGCCGATTCCGACATGCTTAAGTCTACAACCGTTCACTGGCACGGTTTCTTC    90
 K  S  D  N  F  Q  I  N  V  V  N  S  L  A  D  S  D  M  L  K  S  T  T  V  H  W  H  G  F  F CAAAAGGGTACCAACTGGGCTGACGGCCCTGCTTTCGTCAACCAGTGTCCCATTGCGACGGGCAACTCTTTCCTTTACAACTTCAACGCT   120
 Q  K  G  T  N  W  A  D  G  P  A  F  V  N  Q  C  P  I  A  T  G  N  S  F  L  Y  N  F  N  A
                        Cu²⁺ binding site-II
ACGGACCAGGCTGGTACTTTCTGGTACCATTCTCACTTGGAGACTCAGTACTGTGATGGTCTTCGTGGCCCGATGGTTGTCTATGACCCA   150
 T  D  Q  A  G  T  F  W  Y  H  S  H  L  E  T  Q  Y  C  D  G  L  R  G  P  M  V  V  Y  D  P GACGATCCTCATGCTGACCTCTACGATGTCGACGACGATAGCACTGTCATTACTCTTGCCGATTGGTATCACACCCTTGCTCGACTTGGT   180
 D  D  P  H  A  D  L  Y  D  V  D  D  D  S  T  V  I  T  L  A  D  W  Y  H  T  L  A  R  L  G GCCGCTTTCCCGACTTCGGACGCTACTTTGATCAACGGTTTGGGCCGTTACAGCGATGGTAACACAACCGATCTCGCTGTCATTACTGTC   210
 A  A  F  P  T  S  D  A  T  L  I  N  G  L  G  R  Y  S  D  G  N  T  T  D  L  A  V  I  T  V GAATCCGGCAAGAGGTACCGATTCAGGCTGGTCAGCATTTCTTGCGATCCCAACTTCACTTTCTCCATCGACAACCACACCATGACAATC   240
 E  S  F  K  R  Y  R  F  R  L  V  S  I  S  C  D  P  N  F  T  F  S  I  D  N  H  T  M  T  I ATCGAGGCTGATGCTGTCAACTATACACCCCTCGATGTTGACGAGATTCAAATCTTCGCTGGTCAACGTTACTCCTTCATTCTCACTGCC   270
 I  E  A  D  A  V  N  Y  T  P  L  D  V  D  E  I  Q  I  F  A  G  Q  R  Y  S  F  I  L  T  A AACCAGACCGTCGACAACTACTGGATTCGTGCTGACCCCAACGTTGGTACGACTGGCTTCGACAATGGCATCAACTCCGCTATCCTTCGT   300
 N  Q  T  V  D  N  Y  W  I  R  A  D  P  N  V  G  T  T  G  F  D  N  G  I  N  S  A  I  L  R TACAGCGGTGCCGACGAGGTCGAGCCTACCACCAACCAGACCACCAGTACTAACCCTCTTGTTGAGGCTAACTTGGTTCCTCTCGATGGT   330
 Y  S  G  A  D  E  V  E  P  T  T  N  Q  T  T  S  T  N  P  L  V  E  A  N  L  V  P  L  D  G GCTGCTGCTCCCGGTGAAGCTGTCGCTGGAGGTGTTGACTATGCGCTGAACTTGGCTCTCGCTTTCGACGGTACAAACCTCGATTTCACC   360
 A  A  A  P  G  E  A  V  A  G  G  V  D  Y  A  L  N  L  A  L  A  F  D  G  T  N  L  D  F  T GTCAACGGTTACGAGTACACCTCTCCTACCGTCCCAGTCCTACTCCAAATTCTCAGCGGTGCCTCTTCCGTCGACGACTTGCTCCCCAGT   390
 V  N  G  Y  E  Y  T  S  P  T  V  P  V  L  L  Q  I  L  S  G  A  S  S  V  D  D  L  L  P  S
                                                                                        Cu²⁺ binding site-III
GGAAGCATTTACTCACTGCCAAGCAACTCCACTATCGAGCTCAGTATTCCCGCACTTGCCGTCGGTGCTCCCCACCCTATCCATTTGCAC   420
 G  S  I  Y  S  L  P  S  N  S  T  I  E  L  S  I  P  A  L  A  V  G  A  P  H  P  I  H  L  H GGTCACACTTTCTCTGTCGTTCGTAGTGCCGGATCTCACCACCTACAACTACGACAACCCCCTCGTCGTGACGTCAGCATTGGTACC    450
 G  H  T  F  S  V  V  R  S  A  G  S  T  T  Y  N  Y  D  N  P  P  R  R  D  V  V  S  I  G  T
                                                                                        Cu²⁺ binding site-IV
GCCACTGATGATAACGTTACCATTCGTTTCACCACCGACAACCCGGGACCTTGGTTCCTCCACTGTCACATTGACTTCCACTTGGAAGCT   480
 A  T  D  D  N  V  T  I  R  F  T  T  D  N  P  G  P  W  F  L  H  C  H  I  D  F  H  L  E  A GGTTTCGCAGTCGTCTTTGCTGAAGACTTTAATGACACTGCTTCTGCTAACACTGTCACCACTGAATGGAGCGACCTCTGCACTACCTAC   510
 G  F  A  V  V  F  A  E  D  F  N  D  T  A  S  A  N  T  V  T  T  E  W  S  D  L  C  T  T  Y GATGCCCTCTCCTCCGATGACCTCTAA            (SEQ ID NO: 19)                                     518
 D  A  L  S  S  D  D  L  *              (SEQ ID NO: 7)
```

Cerrena sp. WR1 Lcc2 (GenBank accession no. GQ899202)

```
ATGATTAACTTTAATTCGTTACTTACTTTCACAGTCCTAGCACTGTCGATGCGCGCACATGCCGCTATCGGTCCCGTCACTGACCTCACA        30
 M   I   N   F   N   S   L   L   T   F   T   V   L   A   L   S   M   R   A   H   A   A   I   G   P   V   T   D   L   T

ATCACTAATGCCACCATTTCCCCGGATGGTTTCTCTCGTCAAGCCGTGCTTGCTGGAGGTGTTTTCCCTGGTCCGCTTATTACCGGAAAC        60
 I   T   N   A   T   I   S   P   D   G   F   S   R   Q   A   V   L   A   G   G   V   F   P   G   P   L   I   T   G   N
                                                                                                   Cu²⁺ binding site-I
AAGGGCGACAACTTCCAAATCAATGTTGTTAATTCATTGGAAAACTCTGACATGCTTAAGTCTACGACCATTCACTGGCACGGTTTCTTC        90
 K   G   D   N   F   Q   I   N   V   V   N   S   L   E   N   S   D   M   L   K   S   T   T   I   H   W   H   G   F   F CAGAAGGGTACCAACTGGGCCGATGGTCCTGCCTTCGTTAACCAATGCCCCATCGCCACGGGCAACTCTTTCCTGTACAACTTCAACGCA       120
 Q   K   G   T   N   W   A   D   G   P   A   F   V   N   Q   C   P   I   A   T   G   N   S   F   L   Y   N   F   N   A
                                                Cu²⁺ binding site-II
GACGACCAGGCTGGTACATTCTGGTACCACTCTCACTTGTCTACTCAATATTGCGATGGTCTCCGAGGCCCTATGGTCGTCTACGACCCG       150
 D   D   Q   A   G   T   F   W   Y   H   S   H   L   S   T   Q   Y   C   D   G   L   R   G   P   M   V   V   Y   D   P AACGATCCTCACGCTTCCCTCTACGATGTTGATGATGAGAGCACTGTGATTACCCTCGCCGATTGGTACCACACCCTTGCCCGACTTGGT       180
 N   D   P   H   A   S   L   Y   D   V   D   D   E   S   T   V   I   T   L   A   D   W   Y   H   T   L   A   R   L   G GCAGCTTTCCCGACTGCGGATGCTACCCTCATTAACGGCTTGGGTCGTTACAGCGATGGTACTACTTCGGACCTTGCTGTTATCACCGTT       210
 A   A   F   P   T   A   D   A   T   L   I   N   G   L   G   R   Y   S   D   G   T   T   S   D   L   A   V   I   T   V GAGTCCGGAAAGAGGTACCGATTCCGATTGGTCAACATTTCTTGCGACCCCAACTACACTTTCTCTATCGACAACCACACATTCACCGTC       240
 E   S   G   K   R   Y   R   F   R   L   V   N   I   S   C   D   P   N   Y   T   F   S   I   D   N   H   T   F   T   V ATTGAGGTCGATGGTGTCAACCACGCGGCGCTTGATGTCGATGAAATCCAGATCTTCGCTGGTCAACGTTACTCCTTTGTTCTCACTGCT       270
 I   E   V   D   G   V   N   H   A   A   L   D   V   D   E   I   Q   I   F   A   G   Q   R   Y   S   F   V   L   T   A AACCAAACCGTCGACAACTACTGGATCCGRGCAAACCCCAATCTCGGAACCACCGGCTTCGACAACGGCATCAACTCCGCTATCCTCCGT       300
 N   Q   T   V   D   N   Y   W   I   R   A   N   P   N   L   G   T   T   G   F   D   N   G   I   N   S   A   I   L   R TACAGCGGTGCTAACGAGACTGAACCCACCACCACCCAGACCACCGCTACTGCTGCTCTCAGCGAAGCTAGCCTCGTTCCTCTCGAGGAC       330
 Y   S   G   A   N   E   T   E   P   T   T   T   Q   T   T   A   T   A   A   L   S   E   A   S   L   V   P   L   E   D CCTGCTGCTCCTGGTGAGGCCGTTGCCGGAGGTGTCGATTATGCTTTGAACTTGGCATTCGCCTTCGACGGTGCCAACCTTGACTTCACA       360
 P   A   A   P   G   E   A   V   A   G   G   V   D   Y   A   L   N   L   A   F   D   G   A   N   L   D   F   T GTCAACGGTGAAACCTACGTCTCCCCTACCGTCCCCGTCCTCCTCCAAATTCTTAGCGGTGCTTCCTCCGTCTCTGACTTGCTCCCTGCC       390
 V   N   G   E   T   Y   V   S   P   T   V   P   V   L   L   Q   I   L   S   G   A   S   S   V   S   D   L   L   P   A
                                                                                                   Cu²⁺ binding site-III
GGAAGCGTCTACTCCTTGCCCAGCAACTCCACCATCGAGCTCAGCATGCCTGGAGGTGTCGTCGGTGGTGGTCACCCCCTTCACTTGCAC       420
 G   S   V   Y   S   L   P   S   N   S   T   I   E   L   S   M   P   G   G   V   V   G   G   G   H   P   L   H   L   H GGTCACGCCTTCTCCGTTGTTCGTAGTGCCGGCTCTGACACTTACAACTACGTCAACCCCCCTCGCCGTGATGTTGTCAACATTGGTGCT       450
 G   H   A   F   S   V   V   R   S   A   G   S   D   T   Y   N   Y   V   N   P   P   R   R   D   V   V   N   I   G   A
                                                                                                   Cu²⁺ binding site-IV
GCTGGTGACAACGTCACTATCCGTTTCACCACTGACAACCCCGGACCCTGGTTCCTCCACTGCCACATCGATTTCCACTTGGAAGCTGGC       480
 A   G   D   N   V   T   I   R   F   T   T   D   N   P   G   P   W   F   L   H   C   H   I   D   F   H   L   E   A   G TTCGCTGTCGTCTTTGCTGAGGACTTCAACGCCACCGCTTCTTCTAACACCGTCACCACTGAGTGGAGCAACCTTTGCACCACCTACGAC       510
 F   A   V   V   F   A   E   D   F   N   A   T   A   S   S   N   T   V   T   T   E   W   S   N   L   C   T   T   Y   D GCCCTCTCTGCCGACGATCAGTAA         (SEQ ID NO: 20)
 A   L   S   A   D   D   Q   *   (SEQ ID NO: 8)                                                                          517
```

Cerrena sp. WR1 Lcc3 (GenBank accession no. GQ899203)

```
ATGGCCTTCCGAACCGGGTTTTCCGCTTTCATCTCTCTCAGCCTTGCCCTTGGTGCACTCGCTGCTATCGGTCCTGTTGCTGACCTTCAC     30
 M  A  F  R  T  G  F  S  A  F  I  S  L  S  L  A  L  G  A  L  A  A  I  G  P  V  A  D  L  H
ATCACGGATGCGAACGTTTCTCCTGATGGCTTCACTCGACCTGCTGTCCTTGCTGGTGGCACCTTCCCCGGCCCTCTCATTACGGGAAAG     60
 I  T  D  A  N  V  S  P  D  G  F  T  R  P  A  V  L  A  G  G  T  F  P  G  P  L  I  T  G  K
                                                                                Cu²⁺ binding site-I
CAGGGTGACAACTTCCAGATCAATGTCATCGACGAACTCACGGACGCGACTATGTTGAAGTCTACGTCTATTCATTGGCACGGTATCTTC     90
 Q  G  D  N  F  Q  I  N  V  I  D  E  L  T  D  A  T  M  L  K  S  T  S  I  H  W  H  G  I  F
CAGAAAGGCACCAACTGGGCTGACGGCCCCTCCTTCGTCAATCAGTGCCCCATCACTACAGGAAACTCGTTCCTGTACGACTTTTCTGTC    120
 Q  K  G  T  N  W  A  D  G  P  S  F  V  N  Q  C  P  I  T  T  G  N  S  F  L  Y  D  F  S  V
                                Cu²⁺ binding site-II
CCCGACCAGACCGGCACGTACTGGTATCACAGTCATTTATCCACCCAGTACTGTGACGGTTTGCGAGGAGCCCTTGTCATTTACGACGAC    150
 P  D  Q  T  G  T  Y  W  Y  H  S  H  L  S  T  Q  Y  C  D  G  L  R  G  A  L  V  I  Y  D  D
AATGATCCTCACAAGGATCTCTATGATGTTGATGATGAGACTACCGTCATCACCCTCGCCGACTGGTATCATACCCAGGCTCGCCTGATC    180
 N  D  P  H  K  D  L  Y  D  V  D  D  E  T  T  V  I  T  L  A  D  W  Y  H  T  Q  A  R  L  I
ACTGGTGTCCCTGTCTCCGATGCGACTCTGATCAACGGTCTTGGCCGTTATCTTAATGGCCCAACCGATGCTCCGCTCGCTGTTATCACT    210
 T  G  V  P  V  S  D  A  T  L  I  N  G  L  G  R  Y  L  N  G  P  T  D  A  P  L  A  V  I  T
GTCGACCAAGGAAAAACGTTATCGTTTCCGTCTCGTCTCTATTTCATGCGACCCGAACTTCGTCTTCTCCATTGACAACCATTCCATGACT    240
 V  D  Q  G  K  R  Y  R  F  R  L  V  S  I  S  C  D  P  N  F  V  F  S  I  D  N  H  S  M  T
GTCATTGAAGTCGATGCTGTCAACAGCCAGCCTCTCGTCGTCGACTCTATTCAAATCTTCGCGGCACAGCGATACTCCTTCATTTTGAAT    270
 V  I  E  V  D  A  V  N  S  Q  P  L  V  V  D  S  I  Q  I  F  A  A  Q  R  Y  S  F  I  L  N GCCAACCAAAGTGTCGGAAACTACTGGATCCGTGCCAACCCCAACTTGGGCAACACTGGTTTTACGAATGGCATTAACTCGGCCATTCTT    300
 A  N  Q  S  V  G  N  Y  W  I  R  A  N  P  N  L  G  N  T  G  F  T  N  G  I  N  S  A  I  L
CGGTACAATGGTGCTCCTGTTGCTGAGCCCAACACCACCCAAACTGCTAGCACCAACCCCTTGAACGAGGTTAACCTTCACCCTCTAGTT    330
 R  Y  N  G  A  P  V  A  E  P  N  T  T  Q  T  A  S  T  N  P  L  N  E  V  N  L  H  P  L  V
CCCACGCCCGTCCCTGGTACTCCTCAGCCTGGCGGTGTTGATGTTGTCCAGAACCTTGTCCTCGGTTTCAGCGGCGGCAAGTTCACTATC    360
 P  T  P  V  P  G  T  P  Q  P  G  G  V  D  V  V  Q  N  L  V  L  G  F  S  G  G  K  F  T  I
AACGGTGTTGCCTTTTCTCCCCCGACGGTCCCAGTTCTCCTTCAAATCCTTAGCGGTACTACTACTGCCCAAGATCTTCTTCCCACTGGA    390
 N  G  V  A  F  S  P  P  T  V  P  V  L  L  Q  I  L  S  G  T  T  T  A  Q  D  L  L  P  T  G
                                                                                Cu²⁺ binding site-III
TCCATTATCGAGCTTCCCCTCGGAAAGACTGTTGAACTTACCCTGGCAGCGGGCGTTCTCGGTGGTCCCCACCCCTTCCACTTGCACGGT    420
 S  I  I  E  L  P  L  G  K  T  V  E  L  T  L  A  A  G  V  L  G  G  P  H  P  F  H  L  H  G
CACACTTTCCACGTTGTTCGCAGCGCTGGTCAGACTACTCCTAACTACGTCGATCCTATTCTTCGTGACACTGTCAACACCGGTGCTGCT    450
 H  T  F  H  V  V  R  S  A  G  Q  T  T  P  N  Y  V  D  P  I  L  R  D  T  V  N  T  G  A  A
                                                                                Cu²⁺ binding site-IV
GGCGACAATGTTACTATCCGTTTCACCACTGACAACCCTGGACCCTGGTTCCTCCACTGCCACATTGATTGGCACTTGGAAGCCGGTTTC    480
 G  D  N  V  T  I  R  F  T  T  D  N  P  G  P  W  F  L  H  C  H  I  D  W  H  L  E  A  G  F
GCTGTTGTCTTCGCTGAAGGTCTTAACCAGACCAATGCTGCTAACCCCACTCCTGATGCTTGGAACAACCTTTGCGACCTCTACAATGCC    510
 A  V  V  F  A  E  G  L  N  Q  T  N  A  A  N  P  T  P  D  A  W  N  N  L  C  D  L  Y  N  A
CTTCCTGCTGGTGACCAGTAG          (SEQ ID NO: 21)                                                516
 L  P  A  G  D  Q  *            (SEQ ID NO: 9)
```

Lentinus sp. LccA (GenBank accession no. FJ693715)

```
ATGGCCAAGTTTCAGTCTTTGCTCTCCTACACCCTTCTCTCCCTCGTCGCCACTGTCTATGCAGGCATCGGCCCCATTGCTAGCCTCGTC    30
 M   A   K   F   Q   S   L   L   S   Y   T   L   L   S   L   V   A   T   V   Y   A  G   I   G   P   I   A   S   L   V

GTCACCGATGCCCAGATTAGCCCCGACGGCTACTTGCGCGATGCTATCGTGACCAATGGGGTCTTCCCAGCCCCTCTGATCACTGGACGT    60
 V   T   D   A   Q   I   S   P   D   G   Y   L   R   D   A   I   V   T   N   G   V   F   P   A   P   L   I   T   G   R
                                                                                        Cu²⁺ binding site-I
AAGGGTGATCACTTCCAGCTGAATGTCGTGGATTCCATGACAAACCACACCATGCTGAAATCCACAAGTATCCACTGGCATGGCTTCTTC    90
 K   G   D   H   F   Q   L   N   V   V   D   S   M   T   N   H   T   M   L   K   S   T   S   I   H   W   H   G   F   F CAGAAGGGCACAAACTGGGCTGATGGTCCTGCATTTGTGAACCAGTGCCCTATTTCCAGCGGCCACTCGTTCCTCTACGACTTCCACGTT   120
 Q   K   G   T   N   W   A   D   G   P   A   F   V   N   Q   C   P   I   S   S   G   H   S   F   L   Y   D   F   H   V
                           Cu²⁺ binding site-II
CCGGACCAAGCAGGGACGTTCTGGTACCACAGTCACTTGTCCACTCAATACTGCGACGGTTTGAGGGGCCCGATGGTTGTGTACGATCCC   150
 P   D   Q   A   G   T   F   W   Y   H   S   H   L   S   T   Q   Y   C   D   G   L   R   G   P   M   V   V   Y   D   P AACGACCCTCATGCAAATCTCTACGACATCGATAACGACAGCACTGTGATAACTCTCGCCGATTGGTATCACGTCGCGGCCAAGCTCGGC   180
 N   D   P   H   A   N   L   Y   D   I   D   N   D   S   T   V   I   T   L   A   D   W   Y   H   V   A   A   K   L   G CCTCGCTTCCCACTTGGGGCTGATGCTACCCTTATCAACGGAAAGGGCAGAAGCCCTGCCACTCCCACAGCAGCACTGTCCGTCATCAAC   210
 P   R   F   P   L   G   A   D   A   T   L   I   N   G   K   G   R   S   P   A   T   P   T   A   A   L   S   V   I   N GTGGTCAAAGGCAAGCGGTATCGGTTCCGCTTGGTTTCAATCTCCTGCGACCCGAACTATGTGTTCAGCATCGACAACCATACGATGACG   240
 V   V   K   G   K   R   Y   R   F   R   L   V   S   I   S   C   D   P   N   Y   V   F   S   I   D   N   H   T   M   T GTCATCGAGGCCGATACCGTGAACACCCAGCCCCTCGCCGTCGACAGCATCCAGATCTTCGCGGCCCAGCGTTACTCATTCATTCTCAAC   270
 V   I   E   A   D   T   V   N   T   Q   P   L   A   V   D   S   I   Q   I   F   A   A   Q   R   Y   S   F   I   L   N GCCAACCAGCCCGTCGACAACTACTGGATTCGCGCCAACCCCGAACTTCGGGAACGTCGGATTTACGGATGGCATCAACTCTGCTATCCTC   300
 A   N   Q   P   V   D   N   Y   W   I   R   A   N   P   N   F   G   N   V   G   F   T   D   G   I   N   S   A   I   L CGTTACACTGGGGCGGCACTGGTCGAACCGTCTGCGACCACCGCTCCGACACTGAGCAACCCTCTCGTCGAGACAAACCTGCATCCTCTT   330
 R   Y   T   G   A   A   L   V   E   P   S   A   T   T   A   P   T   L   S   N   P   L   V   E   T   N   L   H   P   L GCGCCCATGCCTGTGCCCGGACAACCCGTTTCCGGTGGTGTCGATAAGGCTATCAACTTCGCCTTCAACTTCGATGGCACGGACTTCTTC   360
 A   P   M   P   V   P   G   Q   P   V   S   G   G   V   D   K   A   I   N   F   A   G   N   F   D   G   T   D   F   F ATCAACGGCGCGAGCTTCGTCCCACCTACGGTTCCGGTCCTTCTCCAAATCATGAGCGGCGCCAGCACGGCGCAGGACCTCCTTCCTTCC   390
 I   N   G   A   S   F   V   P   P   T   V   P   V   L   L   Q   I   M   S   G   A   S   T   A   Q   D   L   L   P   S
                                                                                                      Cu²⁺ binding
GGCAGCGTCTACCCGCTTCCATCAAACGCGACGATCGAGCTCTCCTTCCCGGCGACCGCCGCTGCGCCTGGCGCCCCCACCCCTTCCAC   420
 G   S   V   Y   P   L   P   S   N   A   T   I   E   L   S   F   P   A   T   A   A   A   P   G   A   P   H   P   F   H
                                                                                                  site-III
TTGCACGGCCACGTCTTCGCCGTCGTCCGAGCGCGGGAAGCACCACCTACAATTACAACAACCCCATCTGGCGCGATGTCGTCAGCACT   450
 L   H   G   H   V   F   A   V   V   R   S   A   G   S   T   T   Y   N   Y   N   N   P   I   W   R   D   V   V   S   T
                                                                                                    Cu²⁺ binding
GGCACCCCTGCAGCGGGCGACAACGTCACCATCCGTTTTTCGACGAACAACCCGGGTCCGTGGTTCCTCCACTGCCACATCGACTTCCAC   480
 G   T   P   A   A   G   D   N   V   T   I   R   F   S   T   N   N   P   G   P   W   F   L   H   C   H   I   D   F   H
                                                                                                    site-IV
CTCGAGGCGGGCTTCGCAGTAGTCATGGCCGAAGACGTCCCCGACATTCCGTCTGCGAACCCTGTGCCCCAGGCGTGGTCGAACCTTTGC   510
 L   E   A   G   F   A   V   V   M   A   E   D   V   P   D   I   P   S   A   N   P   V   P   Q   A   W   S   N   L   C CCAACTTACAACGCGCTCAGTTCTGATGATCAGTAA    (SEQ ID NO: 22)                                             521
 P   T   Y   N   A   L   S   S   D   D   Q   *   (SEQ ID NO: 10)
```

*Lentinus* sp. LccB (GenBank accession no. FJ693716)

```
ATGGCCAAGTTTCAGTCTTTGCTCTCCTACACCCTTCTCTCCCTCGTCGCCACTGTCTATGCAGGCATCGGCCCCATTGCTAGCCTCGTC     30
 M   A   K   F   Q   S   L   L   S   Y   T   L   L   S   L   V   A   T   V   Y   A  G  I  G  P  I  A  S  L  V

GTCACCGATGCCCAGATTAGCCCCGACGGCTACTTGCGCGATGCTATCGTGACCAATGGGGTCTTCCCAGCCCCTCTGATCACTGGACGT     60
 V   T   D   A   Q   I   S   P   D   G   Y   L   R   D   A   I   V   T   N   G   V   F   P   A   P   L   I   T   G   R
                                                                                                          Cu²⁺ binding site-I
AAGGGTGATCACTTCCAGCTGAATGTCGTGGATTCCATGACAAACCACACCATGCTGAAATCCACAAGTATCCACTGGCATGGCTTCTTC     90
 K   G   D   H   F   Q   L   N   V   V   D   S   M   T   N   H   T   M   L   K   S   T   S   I   H   W   H   G   F   F CAGAAGGGCACAAACTGGGCTGATGGTCCTGCATTTGTGAACCAGTGCCCTATTTCCAGCGGCCACTCGTTCCTCTACGACTTCCACGTT    120
 Q   K   G   T   N   W   A   D   G   P   A   F   V   N   Q   C   P   I   S   S   G   H   S   F   L   Y   D   F   H   V
                                                Cu²⁺ binding site-II
CCCGACCAAGCAGGGACGTTCTGGTACCACAGTCACTTGTCCACTCAATACTGCGACGGTTTGAGGGGCCCGATGGTTGTGTACGATCCC    150
 P   D   Q   A   G   T   F   W   Y   H   S   H   L   S   T   Q   Y   C   D   G   L   R   G   P   M   V   V   Y   D   P AACGACCCTCATGCAAATCTCTACGACATCGATAACGACAGCACTGTGATAACTCTCGCCGATTGGTATCACGTCGCGGCCAAGCTCGGC    180
 N   D   P   H   A   N   L   Y   D   I   D   N   D   S   T   V   I   T   L   A   D   W   Y   H   V   A   A   K   L   G CCTCGCTTCCCACTTGGGGCTGATGCTACCCTTATCAACGGAAAGGGCAGAAGCCCTGCCACTCCCACAGCAGCACTGTCCGTCATCAAC    210
 P   R   F   P   L   G   A   D   A   T   L   I   N   G   K   G   R   S   P   A   T   P   T   A   A   L   S   V   I   N GTGGTCAAAGGCAAGCGGTATCGGTTCCGCTTGGTTTCAATCTCCTGCGACCCGAACTATGTGTTCAGCATCGACAACCATACGATGACG    240
 V   V   K   G   K   R   Y   R   F   R   L   V   S   I   S   C   D   P   N   Y   V   F   S   I   D   N   H   T   M   T GTCATCGAGGCCGATACCGTGAACACCCAGCCCCTCGCCGTCGACAGCATCCAGATCTTCGCGGCCCAGCGTTACTCATTCATTCTCAAC    270
 V   I   E   A   D   T   V   N   T   Q   P   L   A   V   D   S   I   Q   I   F   A   A   Q   R   Y   S   F   I   L   N GCCAACCAGCCCGTCGACAACTACTGGATTCGCGCCAACCCCGAACTTCGGGAACGTCGGATTTACGGATGGCATCAACTCTGCTATCCTC    300
 A   N   Q   P   V   D   N   Y   W   I   R   A   N   P   N   F   G   N   V   G   F   T   D   G   I   N   S   A   I   L CGTTACACTGGGGCGGCACTGGTCGAACCGTCTGCGACCACCGCTCCGACACTGAGCAACCCTCTCGTCGAGACAAACCTGCATCCTCTT    330
 R   Y   T   G   A   A   L   V   E   P   S   A   T   T   A   P   T   L   S   N   P   L   V   E   T   N   L   H   P   L GCGCCCATGCCTGTGCCCGGACAACCCGTTTCCGGTGGTGTCGATAAGGCTATCAACTTCGCCTTCAACTTCGATGGCACGGACTTCTTC    360
 A   P   M   P   V   P   G   Q   P   V   S   G   G   V   D   K   A   I   N   F   A   G   N   F   D   G   T   D   F   F ATCAACGGCGCGAGCTTCGTCCCACCTACGGTTCCGGTCCTTCTCCAAATCATGAGCGGCGCCAGCACGGCGCAGGACCTCCTTCCTTCC    390
 I   N   G   A   S   F   V   P   P   T   V   P   V   L   L   Q   I   M   S   G   A   S   T   A   Q   D   L   L   P   S
                                                                                                          Cu²⁺ binding
GGCAGCGTCTACCCGCTTCCATCAAACGCGACGATCGAGCTCTCCTTCCCGGCGACCGCCGCTGCGCCTGGCGCCCCCACCCCTTCCAC    420
 G   S   V   Y   P   L   P   S   N   A   T   I   E   L   S   F   P   A   T   A   A   A   P   G   A   P   H   P   F   H
                                                                                                          site-III
TTGCACGGCCACGTCTTCGCCGTCGTCCGCAGCGCGGGAAGCACCACCTACAATTACAACAACCCCATCTGGCGCGATGTCGTCAGCACT    450
 L   H   G   H   V   F   A   V   V   R   S   A   G   S   T   T   Y   N   Y   N   N   P   I   W   R   D   V   V   S   T
                                                                                                          Cu²⁺ binding
GGCACCCCTGCAGCGGGCGACAACGTCACCATCCGTTTTTCGACGAACAACCCGGGTCCGTGGTTCCTCCACTGCCACATCGACTTCCAC    480
 G   T   P   A   A   G   D   N   V   T   I   R   F   S   T   N   N   P   G   P   W   F   L   H   C   H   I   D   F   H
                                                                                                          site-IV
CTCGAGGCGGGCTTCGCAGTAGTCTAG            (SEQ ID NO: 23)                                                    488
 L   E   A   G   F   A   V   V   *      (SEQ ID NO: 11)
```

```
Lentinus sp. LccC (GenBank accession no. GQ220322)
ATGGCCAAGTTCCAGTCGTTGCTTTCTTACACTGTCCTCTCCTTCGTCGCGGCTGCCTATGCTGCCATCGGCCCAGTCGCTGACCTTACC    30
 M  A  K  F  Q  S  L  L  S  Y  T  V  L  S  F  V  A  A  A  Y  A  A  I  G  P  V  A  D  L  T ATCAGCAATGCCCAAGTCAGCCCCGACGGCTTCCTCCGCGATGCCGTCGTGACCAACGGCCTGGTCCCTGGGCCCCTCATCACGGGCAAC    60
 I  S  N  A  Q  V  S  P  D  G  F  L  R  D  A  V  V  T  N  G  L  V  P  G  P  L  I  T  G  N
                                                                                 Cu²⁺ binding site-I
AAGGGCGATCGCTTCCAGTTGAATGTCATTGATCAAATGACCAACCACACGATGTTGAAGACTACGAGCATTCACTGGCACGGCTTCTTC    90
 K  G  D  R  F  Q  L  N  V  I  D  Q  M  T  N  H  T  M  L  K  T  T  S  I  H  W  H  G  F  F CAGAAGGGCACCAACTGGGCTGATGGACCTGCGTTTGTGAACCAGTGCCCCATTGCCAGCGGCAACTCCTTCCTCTACGACTTCCAGGTC   120
 Q  K  G  T  N  W  A  D  G  P  A  F  V  N  Q  C  P  I  A  S  G  N  S  F  L  Y  D  F  Q  V
                                 Cu²⁺ binding site-II
CCTGACCAGGCTGGCACCTTCTGGTATCACAGCCACCTTTCGACCCAGTACTGCGACGGTCTCCGGGGGCCTCTCGTTGTGTACGACCCC   150
 P  D  Q  A  G  T  F  W  Y  H  S  H  L  S  T  Q  Y  C  D  G  L  R  G  P  L  V  V  Y  D  P AATGACCCACACGCTGCCCTCTATGATATCGACGATGATAACACCGTTATTACTTTGACTGACTGGTACCATACTGCGGCCAGGCTCGGA   180
 N  D  P  H  A  A  L  Y  D  I  D  D  D  N  T  V  I  T  L  T  D  W  Y  H  T  A  A  R  L  G CCTCGTTTCCCGCTGGGAGCAGATGCCACTCTCATCAACGGCCTGGCCGCAGCCCAGCCACGCCGACCGCCAACCTAACTGTCATCAAC    210
 P  R  F  P  L  G  A  D  A  T  L  I  N  G  L  G  R  S  P  A  T  P  T  A  N  L  T  V  I  N GTTACTCAGGGCAAGCGCTACCGCTTCCGCCTCGTGTCGATCTCTTGCGACCCGAACTATGTGTTCAGCATCGACAACCACACGATGAGC   240
 V  T  Q  G  K  R  Y  R  F  R  L  V  S  I  S  C  D  P  N  Y  V  F  S  I  D  N  H  T  M  S GTCATTGAGACGGACACTGTCAACACTCAACCGCTCACGGTCGATAGCATTCAGATCTACGCCGCCCAGCGCTACTCCTTTGTGCTCACC   270
 V  I  E  T  D  T  V  N  T  Q  P  L  T  V  D  S  I  Q  I  Y  A  A  Q  R  Y  S  F  V  L  T GCCAACCAGTCCGTGGATAACTACTGGATCCGGGCAAACCCCAACTTCGGTAACGTCGGCTTCACGGATGCTATCAACTCGGCCATCCTC   300
 A  N  Q  S  V  D  N  Y  W  I  R  A  N  P  N  F  G  N  V  G  F  T  D  A  I  N  S  A  I  L CGCTATGACGGTGCTCCCGACGCTGAGCCCTCCGCTACCACTGCACCGACGTTGACCAACCCGCTGGTTGAGGCGAACCTTCACCCGCTT   330
 R  Y  D  G  A  P  D  A  E  P  S  A  T  T  A  P  T  L  T  N  P  L  V  E  A  N  L  H  P  L GCTTCGATGCCCGTGCCCGGATCCCCTGTGTCTGGCGGTGTGGACAAGGCCATTAACTTCGTCTTCAACTTCAACGGCACGAACTTCTCC   360
 A  S  M  P  V  P  G  S  P  V  S  G  G  V  D  K  A  I  N  F  V  F  N  F  N  G  T  N  F  S ATCAACAACGCGACTTTCGTTCCGCCCACCGTTCCGGTGCTGCTCCAGATCATGAGCGGCGCCAACACCGCCCAAGACCTCCTGCCCTCT   390
 I  N  N  A  T  F  V  P  P  T  V  P  V  L  L  Q  I  M  S  G  A  N  T  Q  D  L  L  P  S
                                                                                   Cu²⁺ binding
GGCAGCGTGTACACACTCCCGTCCAACGCTACCATTGAGCTGTCCTTCCCTGCGACGAGCAACGCCCCGGCGCTCCTCACCCCTTCCAC    420
 G  S  V  Y  T  L  P  S  N  A  T  I  E  L  S  F  P  A  T  S  N  A  P  G  A  P  H  P  F  H
   site-III
TTGCACGGTCACGTCTTCGCCGTTGTCCGCAGCGCTGGCAGCACCGTCTACAACTACGACAACCCCATCTGGCGCGACGTCGTCAGCACC   450
 L  H  G  H  V  F  A  V  V  R  S  A  G  S  T  V  Y  N  Y  D  N  P  I  W  R  D  V  V  S  T
                                                                                   Cu²⁺ binding
GGCACCCCTGCAGCGGGCGACAACGTCACCATCCGCTTCCAGACCAACAACCCTGGTCCCTGGTTCCTCCACTGTCACATCGACTTCCAC   480
 G  T  P  A  A  G  D  N  V  T  I  R  F  Q  T  N  N  P  G  P  W  F  L  H  C  H  I  D  F  H
   site-IV                                                                         Cu²⁺ binding
CTCGACGCCGGCTTTGCCGTGGTCATGGCTGAGGACCCTGTTGACACTCCGACGGCGGATCCCGTTCCCCAGGCGTGGTCCGATCTCTGC   510
 L  D  A  G  F  A  V  V  M  A  E  D  P  V  D  T  P  T  A  D  P  V  P  Q  A  W  S  D  L  C CCGACATACGACGCGCTTTCCGTCGACGACCAGTGA     (SEQ ID NO: 24)                                   521
 P  T  Y  D  A  L  S  V  D  D  Q  *      (SEQ ID NO: 12)
```

In the above listed sequences, the underlined and italic regions refer to signal peptides, the bold-faced residues refer to glycosylation sites (either predicted by computational methods or determined by mass spectrometry or mutagenesis), and the highlighted regions refer to copper-binding sites. It is known that copper-binding sites are essential to the enzymatic activity of a laccase. Further, in each of the Lentinus sp. laccases, an N-terminal domain (i.e., residues 40-265 in precursor LccB and the corresponding regions in LccA and LccC) and a C-terminal domain (i.e., residues 360-488 in precursor LccB and the corresponding domains in LccA and LccC) are functionally important. The glycosylation sites in each of the Lentinus sp. laccases have also found to be functionally important.

Also described herein are functional variants of Lcc1, Lcc2, Lcc3, LccA, LccB, and LccC that share at least 85% (e.g., 90%, 95%, or 98%) sequence identity to SEQ ID NO:1, 2, 3, 4, 5, or 6. The "percent identity" of two amino acid sequences is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

Relative to their wild-type counterparts, the functional variants of Lcc1, Lcc2, Lcc3, LccA, LccB, and LccC can contain conservative mutations inside the functional domains or at the essential residue positions as described above. A mutation is conservative when the amino acids used for the substitutions have structural or chemical characteristics similar to those of the corresponding replaced amino acids. Examples of conservative substitutions can include: substitution of Ala with Gly or Val, substitution of Arg with His or Lys, substitution of Asn with Glu, Gln, or Asp, substitution of Asp with Asn, Glu, or Gln, substitution of Cys with Ser or Ala, substitution of Gln with Asn, Glu, or Asp, substitution of Glu with Gly, Asn, Gln, or Asp, substitution of Gly with Val or Ala, substitution of Ile with Leu, Met, Val, or Phe, substitution of Leu with Ile, Met, Val, or Phe, substitution of Lys with His or Arg, substitution of Met with Ile, Leu, Val, or Phe, substitution of Phe with Trp, Tyr, Met, Ile, or Leu, substitution of Ser with Thr or Ala, substitution of Thr with Ser or Ala, substitution of Trp with Phe or Tyr, substitution of Tyr with His, Phe, or Trp, and substitution of Val with Met, Ile, Leu, or Gly.

Conservative mutations in the functional domains would not abolish the enzymatic activity of the resultant laccase variants. On the other hand, domains not essential to the laccase activity are tolerable to mutations as amino acid substitutions within these domains are unlikely to greatly affect enzyme activity.

Lcc1, Lcc2, Lcc3, LccA, LccB, LccC, and any of its functional variants can be prepared by conventional recombinant technology. Generally, a coding sequence for one of the laccases can be isolated from *Cerrena* sp. WR1 or *Lentinus* sp. via routine molecular cloning technology. Nucleotide sequences coding for one of the variants can be prepared by modifying a wild-type laccase coding sequence. Any of the coding sequences can then be inserted into an expression vector, which contains a suitable promoter in operative linkage with the coding sequence. If necessary, the coding sequence can be subjected to codon optimization based on the type of the host cell to be used for expressing the laccase.

As used herein, a "vector" refers to a nucleic acid molecule capable of transporting another nucleic acid to which it has been linked. The vector can be capable of autonomous replication or integrate into a host DNA. Examples of the vector include a plasmid, cosmid, or viral vector. An expression is a vector in a form suitable for expression of a target nucleic acid in a host cell. Preferably, an expression vector includes one or more regulatory sequences operatively linked to a target nucleic acid sequence to be expressed. The term "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of transcription of RNA desired, and the like.

The term "promoter" refers to a nucleotide sequence containing elements that initiate the transcription of an operably linked nucleic acid sequence in a desired host cell. At a minimum, a promoter contains an RNA polymerase binding site. It can further contain one or more enhancer elements which, by definition, enhance transcription, or one or more regulatory elements that control the on/off status of the promoter. When *E. coli* is used as the host, representative *E. coli* promoters include, but are not limited to, the β-lactamase and lactose promoter systems (see Chang et al., *Nature* 275:615-624, 1978), the SP6, T3, T5, and T7 RNA polymerase promoters (Studier et al., *Meth. Enzymol.* 185:60-89, 1990), the lambda promoter (Elvin et al., *Gene* 87:123-126, 1990), the trp promoter (Nichols and Yanofsky, *Meth. in Enzymology* 101:155-164, 1983), and the Tac and Trc promoters (Russell et al., *Gene* 20:231-243, 1982). When yeast is used as the host, exemplary yeast promoters include 3-phosphoglycerate kinase promoter, glyceraldehyde-3-phosphate dehydrogenase (GAPDH) promoter, galactokinase (GAL1) promoter, galactoepimerase promoter, and alcohol dehydrogenase (ADH) promoter. Promoters suitable for driving gene expression in other types of microorganisms are also well known in the art. Examples of mammalian cell promoters include, but are not limited to, CMV promoter, SV40 promoter, and actin promoter.

The expression vector described above is then introduced into a suitable host (e.g., *E. coli*, yeast, an insect cell, and a mammalian cell) for expressing of one of the laccases described herein. Positive transformants/transfectants are selected and over-expression of the enzyme can be confirmed by methods known in the art, e.g., immune-blotting or enzymatic activity analysis. A host cell carrying the expression vector is then cultured in a suitable medium under suitable conditions for laccase production. The culture medium or the cells are harvested for isolation of the enzyme. When the enzyme is expressed in precursor form, i.e., containing an N-terminal signal peptide, it is preferred that the culture medium be collected for enzyme isolation. The activity of the isolated enzyme can then be confirmed by a conventional assay, e.g., those described in Example 1 below.

Alternatively, a wild-type laccase or a variant thereof can be prepared by culturing a suitable *Cerrena* sp. or *Lentinus* sp. strain via a traditional method. See, e.g., Examples 1 and 2 below. The enzyme can be purified from the culture medium.

The laccases described herein can oxidize various aromatic, particularly phenolic substrates (e.g. hydroquinone, guaiacol, 2,6-dimethoxyphenol or phenylene diamine), coupled to the reduction of molecular oxygen to water. As such, they have broad biotechnological and industrial applications. For example, they can be used to detoxify industrial effluents, particularly those from the paper and pulp, textile and petrochemical industries. In addition, the laccases described herein can be used to detect and clean up herbicides, pesticides, and certain explosives in environmental water or soil. They also can be used in treating industrial wastewater. Further, given their capacity of removing xenobiotic substances and producing polymeric products, they can serve as bioremediation agents to reduce environmental contamination, decoloration of phenolic dyes, or detoxification of toxic compounds produced, e.g., in bioethanol fermentation. The laccases can also be used in food industry to remove phenolic cmpounds in food products, thereby enhancing food quality or to catalyze chemical synthesis.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

EXAMPLE 1

Isolation and Characterization of Three Novel Laccases from *Cerrena* sp. WR1

(i) *Cerrena* sp. WR1 Cultivation and Laccase Production

Fungus strain *Cerrena* sp. WR1 was maintained on a 3.9% potato dextrose agar (PDA, Difico™, BD) plate. Mycelial plugs from the leading edges of a colony were shattered completely with glass beads in $dH_2O$ and inoculated into a 5 L fermenter (Biostat® B, B. Braun Biotech) containing 4 L cultivation broth, 2.4% potato dextrose broth (PDB) (Difico™, BD), 5% soytone, and 0.4 mM $CuSO_4$ at 25° C. at a stirring speed of 200 rpm with an air flow rate of 1 vvm. Three days later, 2,5-xylidine was added to the culture (final concentration 2 mM) to induce laccase production. The fungal culture was cultivated for additional ten days and the supernatant was collected. Its protein concentration was analyzed by the standard Bradford method (Bio-Rad). The laccase activity in the supernatant was also determined via routine technology.

Genomic DNAs were isolated from *Cerrena* sp. WR1, using the Genomic DNA Purification Kit provided by Easy-Pure, Bioman Scientific Co., LTD, Taiwan, following the manufacturer's protocol. Universal primers NS1 (5'-GTAGT-CATATGCTTGTCTC-3'; SEQ ID NO:25) and NS8 (5'-CCGCAGCTTCACCTACGGA-3'; SEQ ID NO:26) were used to amplify a ~1760 bp-long fragment of 18S rDNA via PCR reactions. See Cheng et al., J. Basic Microbiol. 44 (5): 339-350, 2004. PCR analysis was performed, using a Biometra TGradient Thermocycler (Biometra, Goettingen, Germany), to amplify cDNA fragments encoding 18S rRNA. The PCR conditions are: 30 cycles of 94° C. for 1 min, 56° C. for 45 sec, 72° C. for 2 min, and 72° C. for 5 min. 18S rDNAs of other fungal species were obtained from GenBank and phylogenetic analysis was performed using the computational tool provided by the Biology Workbench website, following the method described in Lai et al., Int. J. Syst. Enol. Microbiol. 51:1873-1880, 2001.

The 18S rDNA sequence of *Cerrena* sp. WR1 was compared with the 18S rDNA sequences from other fungal species retrieved from the GenBank database. A phylogenetic tree was generated based on the results. See FIG. 1. *Cerrena* sp. WR1 18S rDNA shares 99.15% identity to that from 18S rDNA *C. unicolor*, indicating that these two *Cerrena* strains are very close.

(ii) Protein Purification and Characterization

Mycelia of *Cerrena* sp. WR1 were grown in a culture medium containing 2.4% potato dextrose broth, 5% soytone, and 0.4 mM $CuSO_4$ for 13 days. Fungal cells were removed from the culture medium by filtration using a filter paper (5C, Advantec, Toyo Roshi Kaisha, Ltd.) and then a 0.45 μM membrane (Millipore).

Laccase activity in the medium thus collected was determined by the standard 2,2'-azino-bis-(3-ethylbenzthiazoline-6-sulfonic acid (ABTS) oxidation assay as described in Murugesan et al., *Appl. Microbiol. Biotechnol.* 72 (5):939-946, 2006. More specifically, 0.5 ml test sample was incubated with 0.5 ml citric acid buffer (100 mM, pH 3.0) containing ABTS (4 mM) and the optical density at 420 nm ($\epsilon_{420}$=36,000 $M^{-1}cm^{-1}$) of the mixture was measured at various time points. One unit of the enzyme activity was defined as the amount of enzyme needed to oxidize 1 μmol of ABTS per min. Kinetic studies were performed independently for at least three times at different substrate concentrations, pH conditions, and temperatures. All chemicals used in this study were obtained from Merck (Darmstadt, Germany) or Sigma-Aldrich (St. Louis, Mo. USA). All spectrophotometric measurements were performed using the Beckman DU 640 spectrophotometer (Beckman Coulter, USA).

Figure 2:
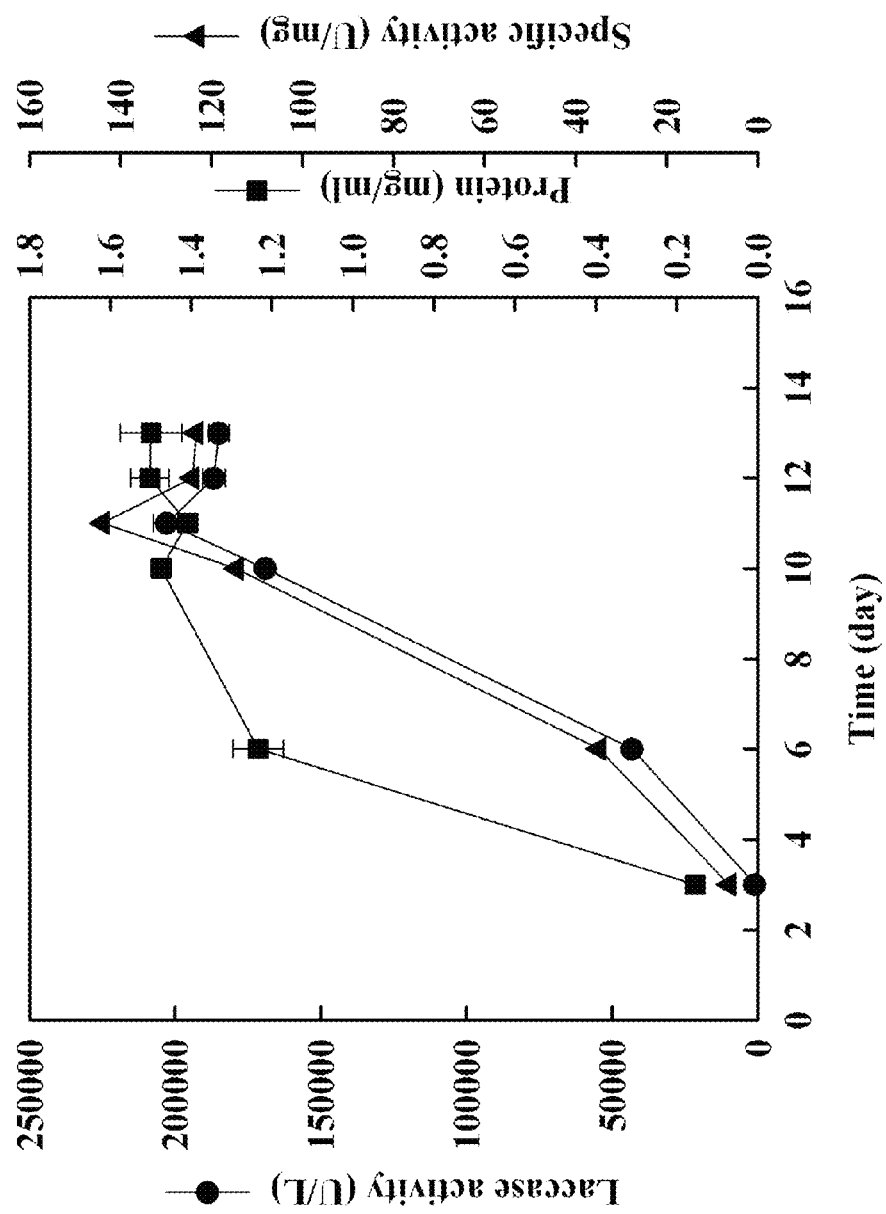
FIG. 2 is a chart showing a time course of laccase activities, protein levels, and specific activities during a 13-day fermentation period of *Cerrena* sp. WR1.

As shown in FIG. 2, the laccase activity in the culture medium increased in the 13-day fermentation period in a time dependent manner. The highest laccase activity reaches approximately 202,000 U/L, and the specific activity of the crude laccases was 144.3 U/mg.

Laccases were isolated from the medium thus collected follow the procedure described below, which was performed at 4° C. The medium was first concentrated using the Lab-scale™ TFF System (Millipore) with a 10K Pellicon®-XL filter. The concentrated medium was then subjected to ammonium sulfate precipitation. Proteins precipitated with 40-60% ammonium sulfate were collected by centrifugation at 6,000×g for 35 min and resuspended in 50 mM sodium phosphate buffer, pH 6.0 ("buffer A"). The resulting protein solution was loaded onto a Q Sepharose Fast Flow column (2.6× 40 cm, GE Healthcare, Uppsala, Sweden) equilibrated with buffer A. The column was washed with the same buffer and the proteins bound to it were eluted with a linear gradient of NaCl (0 to 1 M) in buffer A at a flow rate of 1 mL/min. Each fraction was examined to determine its laccase activity and those exhibiting laccase activity were pooled, concentrated, and dialyzed against buffer A. Homogeneity of the enzyme was confirmed the conventional SDS-PAGE analysis, as well as by zymography analysis and mass spectrometry described below.

Zymography analysis was performed to determine the enzymatic activity as follows. The proteins, suspended in a lysis buffer, were separated on a 10% SDS polyacrylamide gel. After electrophoresis, the gel was rinsed twice with 50 mM citric acid buffer (pH 3.0) for 5 min each time to remove SDS, then immersed in the same buffer containing 1 mM 2,2'-azino-bis-(3-ethylbenzthiazoline-6-sulfonic acid) (ABTS) (Sigma), which is a laccase substrate. The protein bands exhibiting laccase activity can then be visualized. The exact mass of the purified laccase was determined by use of Thermo Finnegan ProteomeX LTQ (LC-ESI-MS/MS) (Thermo, MA) at the Proteomics Core Laboratory, Institute of Plant and Microbial Biology, Academia Sinica, Taiwan.

After the second Q Sepharose Fast Flow column purification, the enzyme was purified about 24.9-fold with a yield of 6.5%, and specific activity of the purified laccase with >95% homogeneity was determined as 2,159.6 U/mg at 30° C. and pH 3.0. The purified laccase, designated as *Cerrena* sp. WR1 Lcc3, was subjected to N-terminal sequencing using a Procise® LC Protein Sequencing System, Model 492 (Applied Biosystems) and LC/MS-MS analysis.

A purified *Cerrena* sp. WR1, designated Lcc3, was also subjected to deglycosylation analysis using the Enzyme Protein Deglycosylation Kit (Sigma-Adlrich), following the manufacturer's protocol. PNGase F, O-glycosidase, α-2(3,6, 8,9) neuraminidase, β-1,4-galactosidase, and β-N-acetylglucosaminidase were used for deglycosylation. The treated laccase, together with an untreated laccase (as a control), was subjected to transblotting onto a polyvinylidene fluoride (PVDF) membrane (Millipore) and periodic acid Schiff staining was then performed as described in Cagatay et al., Veterinary Microbiology 126(1-3): 160-167, 2008 and Gradilone et al., Analytical Biochemistry 261(2):224-227, 1998. The molecular weight of Lcc3, before and after deglycosylation analysis, was determined to be 64.1 and 57.5 kDa, respectively, via SDS-PAGE (10% gel). The glycosylation level in this laccase was calculated to be 11.5%.

UV-Vis absorption spectra analysis showed that Lcc3 exhibited a broad absorption peak at 600 nm and a shoulder absorption at 330 nm. This indicates that Lcc3 contains both type I and type III copper ions.

Thermal denaturation of laccase was determined by differential scanning calorimetry (DSC) using a Nano Differential Scanning calorimeter (N-DSC III) (TA Instruments, New Castle, Del.) at a heating rate of 1° C./min under a temperature from 30 to 95° C. and excess pressure of 3.0 atm. The protein concentration was 0.55 mg/ml in 10 mM sodium phosphate buffer (pH 6.0). Baseline corrections were performed and smoothed by subtracting a buffer thermogram. The data were then analyzed using the Launch NanoAnalyze Software (TA Instruments, New Castle, Del.), assuming a two-state unfolding model. See Pace et al., The Protein Structure: A Practical Approach; Creighton T. E., Ed.: IRL Press; Oxford U.K., pp. 311-330; 1989. Results from this DSC analysis demonstrated that Lcc3 was denatured at a high temperature, with a midpoint temperature ($T_m$) of 73.95° C., in 10 mM sodium phosphate buffer (pH 6.0).

(iii) Effect of Temperature, pH, and Solvent on Laccase Activity and Stability

The effect of temperature on laccase activity was studied using the standard enzymatic activity assay described above under various reaction temperatures (i.e., 20-80° C.). For thermal stability study, the enzyme was pre-incubated in a 50 mM citric acid buffer (pH 3.0) at 50-80° C. for 0-180 min and the residual enzymatic activity was then determined.

Figure 3:
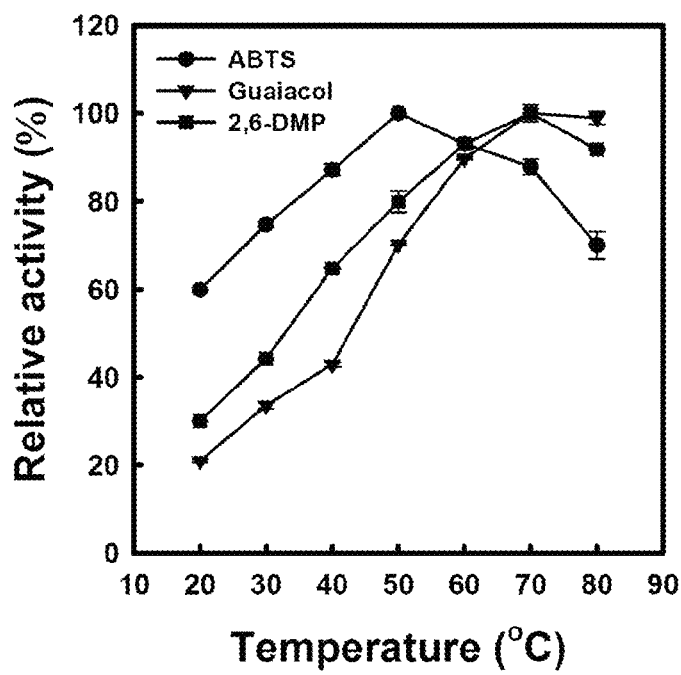
FIG. 3 is a diagram showing the effects of temperature and pH on activity and stability of *Cerrena* sp. WR1 Lcc3. Panel A: effect of temperature on laccase activity; Panel B: effect of temperature on laccase stability; Panel C: effect of pH on laccase activity; Panel D: effect of pH on laccase stability.
Figure 3:
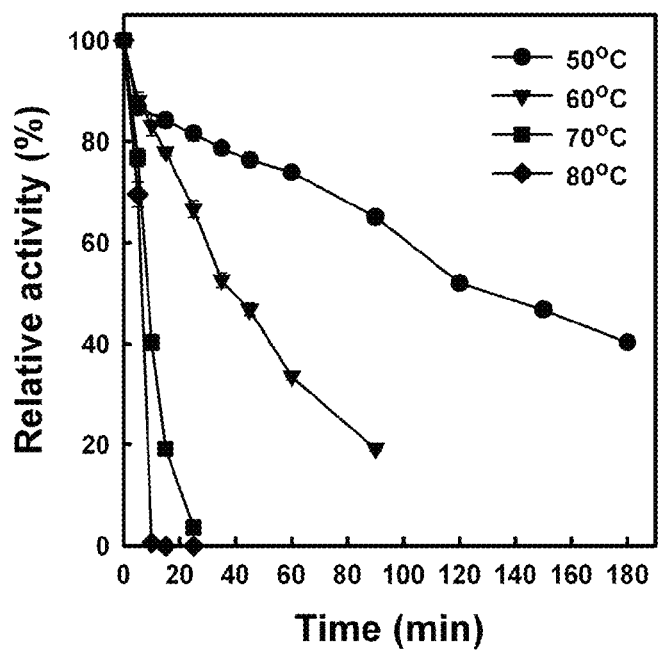
Figure 3:
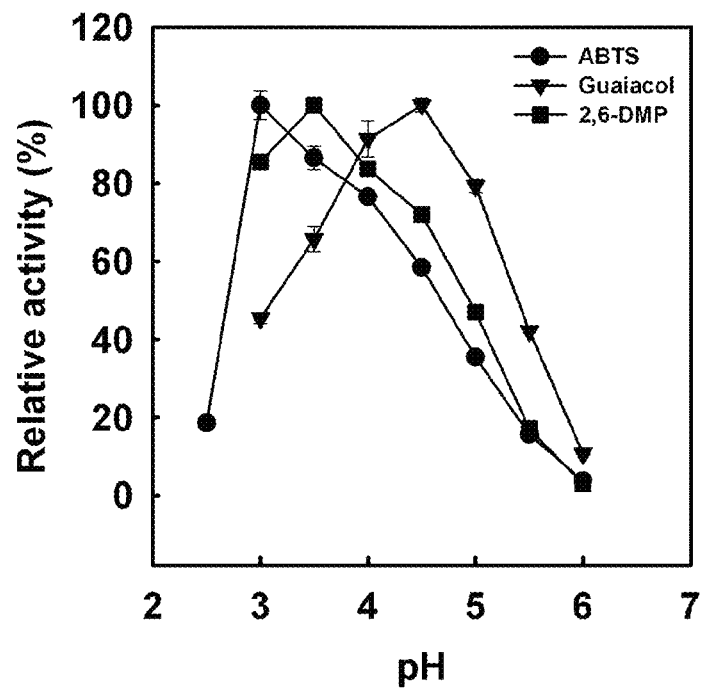
Figure 3:
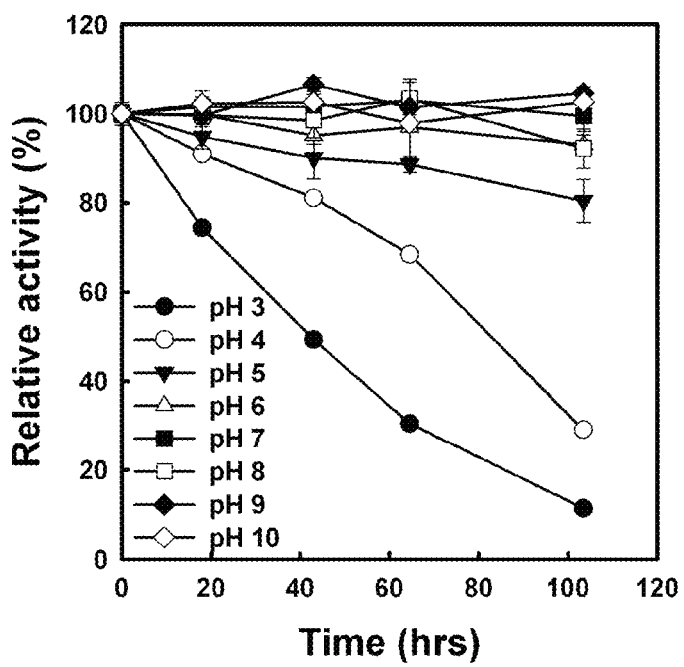

As shown in FIG. 3, panel A, the optimal temperature for Cerrena sp. WR1 Lcc3 was 50° C. when ABTS was used as the substrate and 70° C. when guaiacol or 2,6-DMP was used as the substrate. To test thermal stability, the enzyme was kept at various temperatures (50-80° C.) for 10-40 min and the remaining enzymatic activity was determined using the standard activity assay. Thermal stability at a particular temperature is represented by a $t_{1/2}$ value at that temperature, which represents the longest incubation period during which at least 50% of the enzymatic activity remains. The values of $t_{1/2}$ at 50° C., 60° C., and 70° C. were 120 min, 40 min, and 7.5 min, respectively. See FIG. 3, panel B. Surprisingly, the $t_{1/2}$ of the enzyme incubated at room temperature (25° C.) in a 50 mM sodium phosphate buffer (pH 6.0) was determined to be 40 days, indicating that this laccase is very stable at room temperature.

The effect of pH on the laccase activity was investigated at a pH range of 2.5-6.0. Four buffer systems were used in this study: 50 mM glycine-HCl buffer (pH 2.5), 50 mM citric acid buffer (pH 3.0-5.5), 50 mM sodium phosphate buffer (pH 6.0-8.0), and 50 mM glycine-NaOH buffer (pH 9.0-10). To determine the protein stability of laccase at a wide range of pH conditions, the enzyme (0.1 mg/mL in each reaction) was pre-incubated at pH 3.0-10 at 25° C. for 0-5 days and then the residual enzyme activity was determined.

Lcc3 showed a maximal activity at pH 3.0, 3.5, and 4.5, using ABTS, 2,6-DMP, and guaiacol as the substrates, respectively. See FIG. 3, panel C. This laccase was found to be stable under a neutral or basic environment (pH 6-10). It maintained about 100% activity at pH 6-10 after 63 hr incubation. See FIG. 3, panel D. On the other hand, Lcc3 was found to be less stable at an acidic environment (pH 3.0-5.0).

To test the effects of various organic solvents on laccase activity, the enzymatic assay described above was carried out in the presence of one of the organic solvents shown in Table 1 below at various concentrations (1%, 10% and 25%). A T. versicolor (Fluka) laccase was used as a reference enzyme in this study. The enzyme concentration used in this study was 0.2 mg/ml. As shown in Table 1, Lcc3 retained at least 81% activity in the presence of 25% methanol and N,N-dimethyl formamide. Further, more than 80% laccase activity remained in the presence of 10% acetonitrile or dimethyl sulfoxide.

TABLE 1

Effect of Various Organic Solvent on Cerrena sp. WR1. Lcc3

| Organic solvents | Relative activity (%)* | | |
| --- | --- | --- | --- |
| | 1% | 10% | 25% |
| Methanol | 93.0 ± 1.5 | 85.5 ± 0.9 | 74.6 ± 1.4 |
| Ethanol | 94.5 ± 1.8 | 93.9 ± 4.0 | 84.8 ± 3.3 |
| Acetonitrile | 92.7 ± 2.5 | 86.7 ± 0.8 | 77.5 ± 3.2 |
| N,N-dimethylformamide | 100 ± 0.9 | 98.4 ± 0.5 | 81.2 ± 0.5 |
| Dimethyl sulfoxide | 93.5 ± 1.4 | 81.1 ± 2.2 | 55.8 ± 1.7 |

*Assay reactions were performed in 50 mM citric acid buffer (pH 3.0) at 30° C., with ABTS used as the substrate.

To examine the effect of ethanol on Cerrena sp. WR1 laccase stability, the enzyme was incubated in a 50 mM sodium phosphate buffer (pH 6.0) containing 1%, 10%, or 25% ethanol at room temperature for up to 52 days and the residual enzyme activity was measured at different time points during incubation. A T. versicolor laccase (LccTv) was used as a reference enzyme. The results indicate that LccTv lost approximately 50% activity after being incubated with 25% ethanol for 8 days, while it maintained about 50% activity after a 21-day incubation in the absence of ethanol. Differently, Lcc3 retained around 90% activity after being incubated with 25% ethanol for 10 days and retained approximately 50% enzymatic activity after a 40-day incubation period. This enzyme also retained about 50% enzymatic activity after a 45-day incubation period with 10% ethanol and a 40-day incubation without ethanol. After a 52-day incubation period with 1% ethanol, Lcc3 still exhibited about 61% activity. These results demonstrate that Lcc3 is stable when exposed to ethanol, indicating that this enzyme has a great potential in biofuel industry.

(iv) Laccase Kinetics

Kinetic parameters $K_m$ and $V_{max}$ were determined as follows. Enzymatic activity using various substrates at various concentrations (i.e., ABTS: 1-1000 µM; guaiacol: 1-3000 µM; and 2,6-DMP: 1-2000 µM) was determined in a citrate buffer (50 mM) at the optimum temperature and pH conditions mentioned above. The oxidation reactions of guaiacol and 2,6-DMP were monitored by determining $OD_{436}$ values ($\epsilon$=6,400 $M^{-1}cm^{-1}$) and $OD_{468}$ values ($\epsilon$=49,600 $M^{-1}$ $cm^{-1}$), respectively. The kinetic parameters were determined by non-linear regression analysis (ENZFITTER software program, Elsevier-Biosoft, Cambridge, UK) using the Michaelis-Menten model.

The affinities ($K_m$), turnover rate ($k_{cat}$), and catalytic efficiency ($k_{cat}/K_m$) of Lcc3 were determined to be 3.27 µM, 934.6 $s^{-1}$, and 285.8 $s^{-1}µM^{-1}$ for ABTS, 849.1 µM, 147.9 $s^{-1}$, and 0.21 $s^{-1}$ $µM^{-1}$ for guaiacol, and 392.7 µM, 109.2 $s^{-1}$, and 0.28 $s^{-1}µM^{-1}$ for 2,6-DMP, respectively. The kinetics of the Cerrena sp. WR1 laccases were compared with laccases from other fungal species and the results are shown in Table 2 below:

TABLE 2

Kinetic properties of laccases from various microorganisms

| Fungal Species | Specific activity (U/mg) | $k_{cat}$ (s$^{-1}$) | $K_m$ (µM) | $k_{cat}/K_m$ (s$^{-1}$µM$^{-1}$) | Optimum temperature (°C.) | $t_{1/2}$ (min) |
|---|---|---|---|---|---|---|
| *Cerrena* sp. WR1 [a] | 1013.5 | 934.6 | 3.27 | 285.8 | 50 (at pH 3.0) | 120 (at 50° C.), 40 (at 60° C.) 8 (at 70° C.) |
| *Cerrena* sp. WR1 [b] | 189.7 | 147.9 | 849.1 | 0.21 | 70 (at pH 4.5) | — |
| *Cerrena* sp. WR1 [c] | 118.3 | 109.2 | 392.7 | 0.28 | 70 (at pH 3.5) | — |
| *Trametes versicolor* [a] | 750 | — | — | — | 50 (at pH 3.0) | 15 (at 50° C.), 5 (at 70° C.) |
| *Melanocarpus* sp. [a] | 42.45 | — | — | — | 70 (at pH 6.0) | >360 (at 50° C.) <15 (at 70° C.) |
| *Coriolus versicolor* [a] | 0.3 | — | — | — | 25 (at pH 4.5) | — |
| *Trametes versicolor* [a] | 310 | 351.3 | 37.3 | 9.4 | 55 (at pH 4.0) | — |
| *Trametes* C30 LAC2 [a] | 934 | 683.33 | 536 | 1.27 | 55 (at pH 5.7) | — |
| *Trametes pubescens* LAP2 [a] | 1100 | 350 | 43 | 8.14 | 25 (at pH 4.0) | — |
| *Cerrena unicolor* [a] | | | 800 | | 70 (at pH 3.5) | <25 (at 50° C.) |
| *Panus*(*Lentinus*)*tigrinus* 8/18 [a] | | | 33.4 | | | |
| *Agaricus blazei* [a] | 174.6 | 21 | 63 | 0.33 | 25 (at pH 2.3) | >250 (at 25° C.) |
| *Panus tigrinus* [a] | — | 185.69 | 31 | 5.99 | 30 (at pH 3.5) | 150 (at 25° C.) |
| *Pleurofus sajor-caju* [a] | 1244.4 | 520.24 | 56 | 9.29 | 40 (at pH 5.0) | — |
| *Pycnoporus sanguineus* [a] | 340.76 | 1.155 | 77 | 0.015 | 25 (at pH 3.0) | — |

[a] Kinetic properties with ABTS used as the substrate.
[b] Kinetic properties with guaiacol used as the substrate.
[c] Kinetic properties with 2,6-DMP used as the substrate.

(v) Lignin Degradation and Dye Decoloration Analysis

Figure 4:
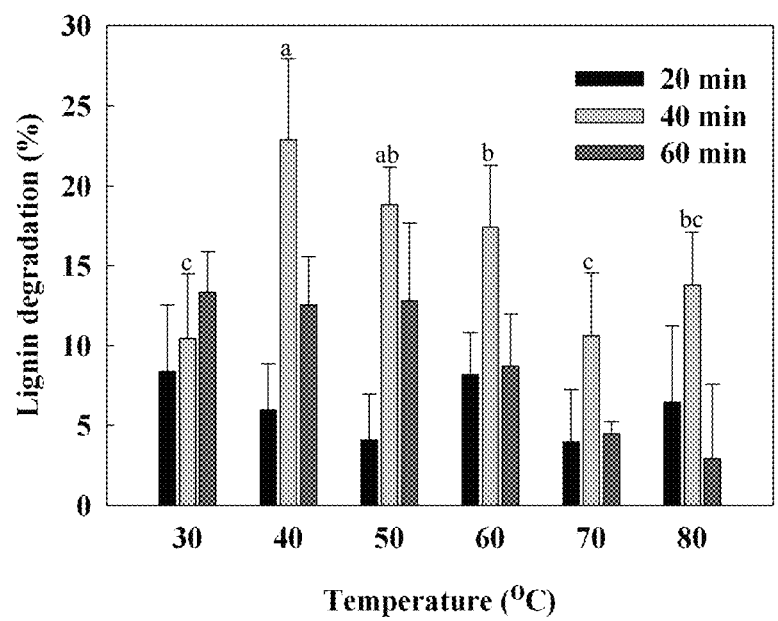
FIG. 4 is a chart showing lignin degradation (panel A) and RBBR decoloration (panel B) by crude laccase fraction from *Cerrena* sp. WR1 or by Lcc3.
Figure 4:
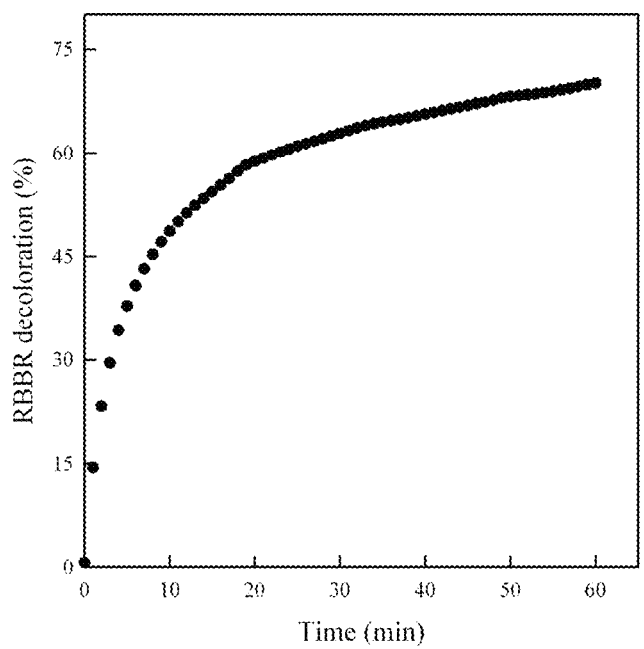

Lignin degradation reaction was carried out by mixing a crude laccase broth (containing 100 U enzyme) with 50 ml reaction buffer (50 mM citric acid solution; pH 3.0) containing 100 mg smashed rice straw materials. The mixture was incubated at 30-80° C. for 20-60 min. Sodium azide was added to the mixture at a final concentration of 1 mM to stop the enzymatic reaction. The processed rice straw was collected by filtration and dried at 60° C. The lignin contents in the rice straw before and after treatment were determined following the method described in kappa number of ISO 302:2004 (International Organization for Standardization). The results were shown in FIG. 4, panel A. The highest lignin degradation efficiency per 100 U Lcc3 was around 22.9%, which was observed when performing the degradation reaction at 40° C. for 40 min.

Dye decoloration reaction was performed by mixing a partially purified laccase broth (containing 8 U enzyme) with a 1 ml reaction buffer (50 mM citric acid solution; pH 3.0) containing 0.02% RBBR (Sigma). The mixture was incubated at 20° C. for 1 h. Dye decoloration was determined by monitoring the change in absorbance at 595 nm and the dye decoloration efficiency (%) was defined as the relative amount of dye reduced after the treatment. See FIG. 4, panel B. Lcc3 exhibited 70.1% decoloration efficiencies against RBBR at 20° C.

(vi) Cloning of Laccase Genes from *Cerrena* Sp. WR1 and Expressing Laccases in *Pichia*

Mycelia of *Cerrena* sp. WR1, after being cultured in PDB for 13 days, were harvested by paper filtration and ground in liquid nitrogen. Total RNA was isolated from the mycelia using the RNeasy® Mini Kit (Qiagen). The first pool of cDNA fragments was obtained by RT-PCR with the SuperScript® III RTS First-Strand cDNA Synthesis Kit (Invitrogen). The *Cerrena* sp. WR1 laccase genes were then amplified using two degenerative primers LAC-N1 (5'-CAYTGGCAYGGNTTYTTYCA-3'; SEQ ID NO:27) and LAC-C1 (5'-TGRAARTCDATRTGRCARTG-3'; SEQ ID NO:28). These two primers were designed based on the sequences in highly conserved copper-binding regions I and IV in fungal laccases. See Hoshida et al., The Society for Biotechnology, Japan, 92(4):372-380. The PCR products were cloned into a vector plasmid, using the Zero Blunt® TOPO® PCR Cloning Kit (Invitrogen), and subjected to sequencing analysis to determine the full-length cDNA sequences coding for the laccases.

Three *Cerrena* sp. WR1 laccase genes, i.e., lcc1, lcc2, and lcc3, were identified. lcc1 cDNA (SEQ ID NO:19), including 1,557 bp, encodes a polypeptide of 518 amino acid residues (SEQ ID NO:7); the lcc2 cDNA (SEQ ID NO:20), including 1,554 bp, encodes a polypeptide of 517 amino acid residues (SEQ ID NO:8); and the lcc3 cDNA (SEQ ID NO:21), including 1,551 bp, encodes a polypeptide of 516 amino acid residues (SEQ ID NO:9). Each of the three polypeptides are in precursor form including a 21-amino-acid long signal peptide at its N-terminus.

The EasySelect™ *Pichia* Expression System (Invitrogen) was used in this study for expression of Lcc1, Lcc2, and Lcc3 laccases. cDNA fragments coding for these three laccases were cloned into *Pichia* expression vector pPICZA or pPICZaB via EcoRI and NotI restriction sites. More specifically, the lcc1 gene coding for Lcc1 precursor (including a signal peptide sequence) was cloned into pPICA to generate expression plasmid pPICZA-lcc1 and the lcc2 and lcc3 genes coding for mature Lcc2 and Lcc3 were cloned into pPICZaB to obtain expression plasmids pPICZaB-lcc2 and pPICZaB-lcc3, respectively. The three expression plasmids were introduced into *P. pastoris* X-33 cells following the method described in Invitrogen's protocol. Positive transformants were cultured in BMMY (1% yeast extract, 2% peptone, 100 mM potassium phosphate, pH 6.0, 1.34% yeast nitrogen base, 0.00004% biotin, and 0.5% methanol) at 25° C., 200 rpm for 12-26 days. Methanol was added to the culture media daily to reach a final concentration of 0.5%. During the cultivation, 1 ml of the supernatant was collected at various time points.

The laccase activity and cell density in the supernatant were determined following the method described above or routine procedures.

Figure 5:
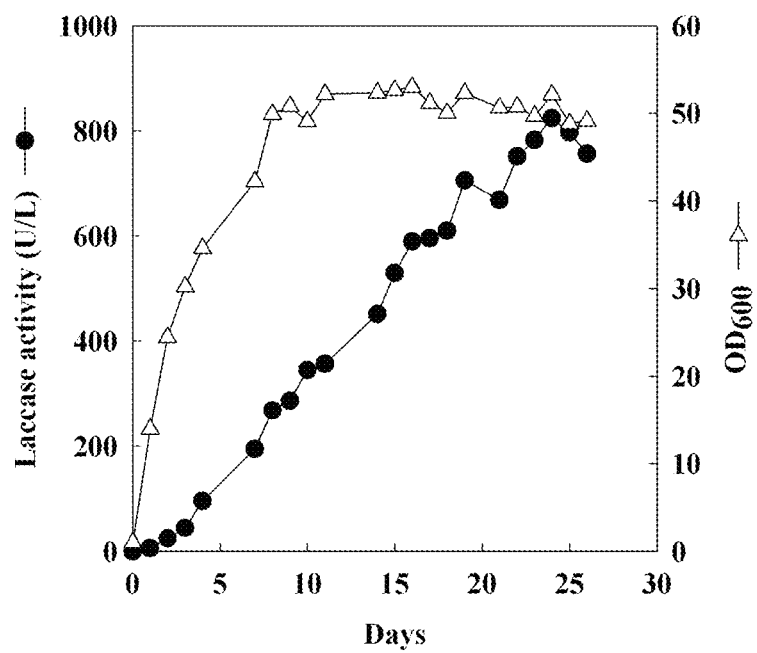
FIG. 5 is a diagram showing production of Lcc1, Lcc2, and Lcc3 in *P. pastoris* host cells via recombinant technology and growth curves of the host cells. Panel A: Lcc1; Panel B; Lcc2, and Panel C: Lcc3.
Figure 5:
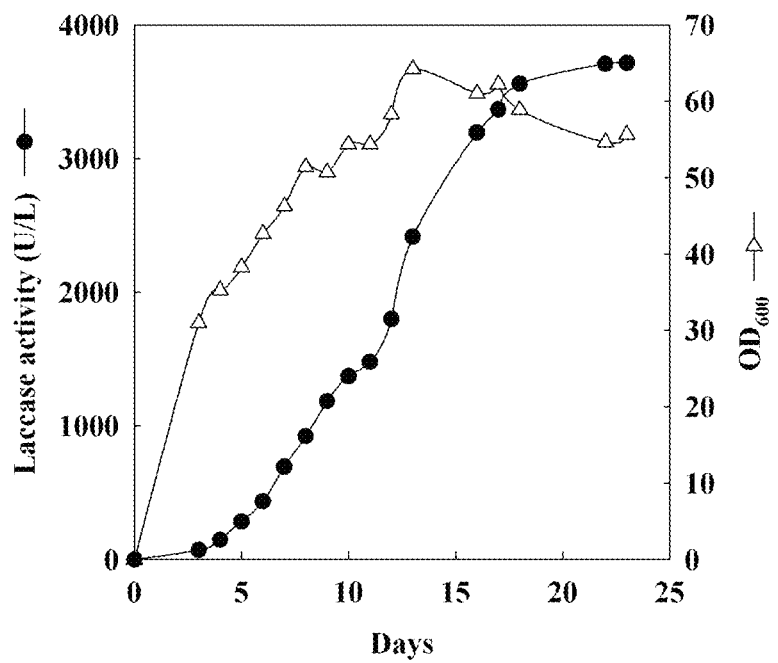
Figure 5:
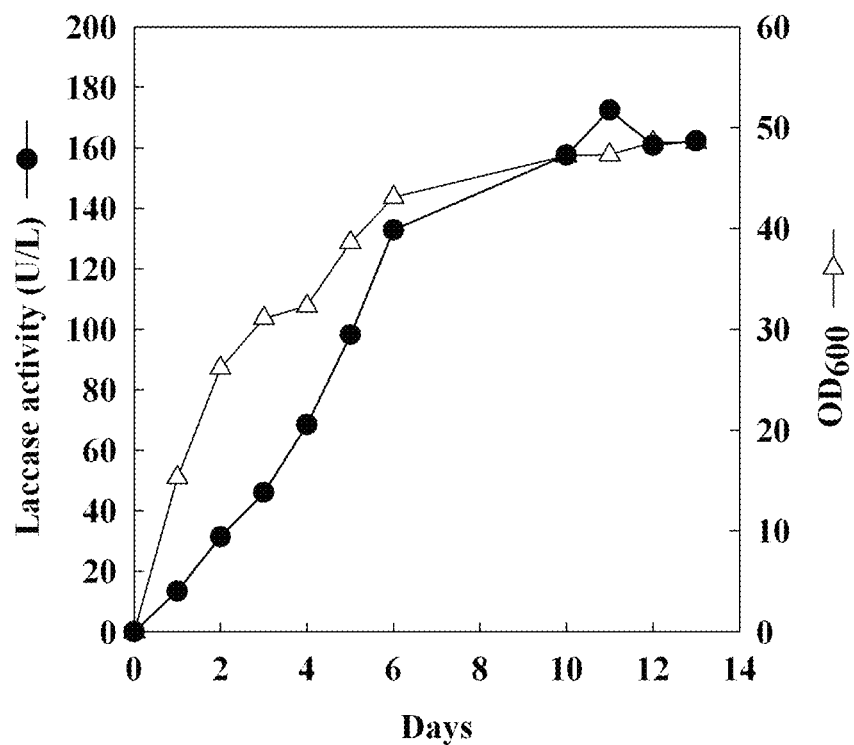

Precursor Lcc1 and mature Lcc2 and Lcc3 were successfully expressed in *P. pastoris* strain X-33 via routine procedures. As shown in FIG. 5, approximately 800 U/L (Lcc1), 160 U/L (Lcc2), and 3700 U/L (Lcc3) were observed in culture media after 13-26 day cultivation.

EXAMPLE 2

Isolation and Characterization of Three Novel Laccases from *Lentinus* sp.

(i) *Lentinus* Sp. Cultivation and Laccase Production

A target *Lentinus* sp. strain was maintained on a potato dextrose agar (PDA) plate following routine procedures. A mycelium from the slant was transferred to a fresh PDA plate and incubated at 28° C. for 5 days. The resulting mycelial discs from the peripheral region of an actively growing colony were used as an inoculum.

Figure 6:
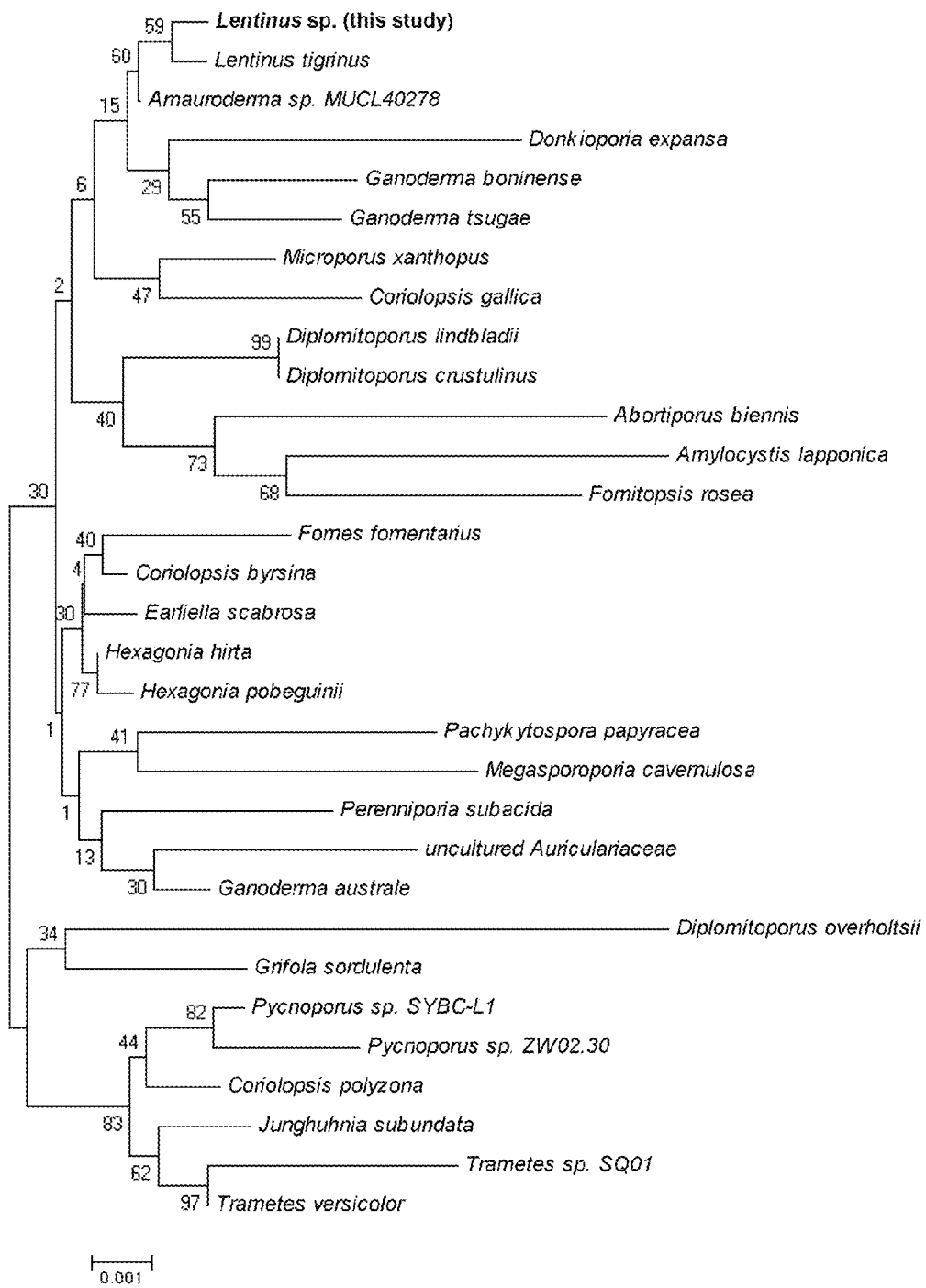
FIG. 6 is a diagram showing the phylogenetic relationship between *Lentinus* sp. and other fungal strains. Bootstrap values at nodes refer to the percentage of 500 replicates. Scale bar: base substitutions per 100 bases.

The phylogeny of the target *Lentinus* sp. strain was determined based on its 18S rDNA sequence, following the method described in Example 1 above. Briefly, DNA fragments encoding 18S rRNA were obtained by PCR as described above. The resultant DNA fragments, including 1783 bp, were confirmed by double-strand DNA sequencing as coding for the 18S rRNA. The rDNA sequence thus obtained was compared with other fungal 18S rDNA sequences obtained from the GenBank database via the Clustal method using the MEGA 4.1 software (DNASTAR, Madison, Wis.). The alignment result was then analyzed with the same software for calculation of distance matrix. Neighbor-joining correction of distances was used to construct a phylogenetic tree, shown in FIG. 6.

The result indicate that the target *Lentinus* sp. strain in the current study was closest to the species of *Lentinus tigrinus* (GenBank accession no. AY946269), with 99.2% 18S rDNA sequence identity as determined by the neighbor-joining method.

(ii) Protein Purification and Characterization

A *Lentinus* sp. strain inoculum, prepared as described above, was inoculated into a medium containing 2.4% potato dextrose broth, 5% soytone, and 0.4 mM $CuSO_4$ and cultured at 25° C. and 150 rpm for 18 days. Three days after inoculation, 2,5-xylidine was added to a final concentration of 2 mM as an inducer for laccase production. During the cultivation, 1 ml of the supernatant was collected at various time points and the laccase activity/protein concentration in the supernatant was determined as described in Example 1 above. More than 90% of the laccase proteins were found to be secreted into the culture medium.

After the 18-day cultivation, the culture medium was collected and concentrated using the Labscale™ TFF System (Millipore, Billerica, Mass.) with a 10K Pellicon®-XL filter. The filtrate was dialyzed against a 50 mM sodium phosphate buffer (pH 6.0), and then purified using two sequential Q Sepharose columns (2.6×30.0 cm, GE Healthcare, Uppsala, Sweden), both of which were pre-equilibrated with the same buffer. Proteins were eluted with a 0-1.0 M NaCl gradient in a 50 mM sodium phosphate buffer (pH 6.0) at a flow rate of 0.5 ml/min. The fractions exhibiting laccase activity were pooled and dialyzed against a 50 mM sodium phosphate buffer (pH 6.0) containing 1.0 M NaCl and then concentrated with an Amicon Ultra-15 centrifugal filter device (Millipore). A final gel filtration purification procedure using a Superdex 200 column (GE Healthcare) (1.6×90 cm, flow rate: 0.2 ml/min) was performed to obtain a purified laccase protein fraction with >96% homogeneity as determined by SDS-PAGE.

Zymography analysis was performed as described above to determine laccase activity. The exact mass of the purified laccase was determined by use of Thermo Finnegan ProteomeX LTQ (LC-ESI-MS/MS) (Thermo, MA) at the Proteomics Core Laboratory, Institute of Plant and Microbial Biology, Academia Sinica, Taiwan. The purified laccase was also subjected to Glycoprotein analysis following the method described in Example 1 above.

Figure 7:
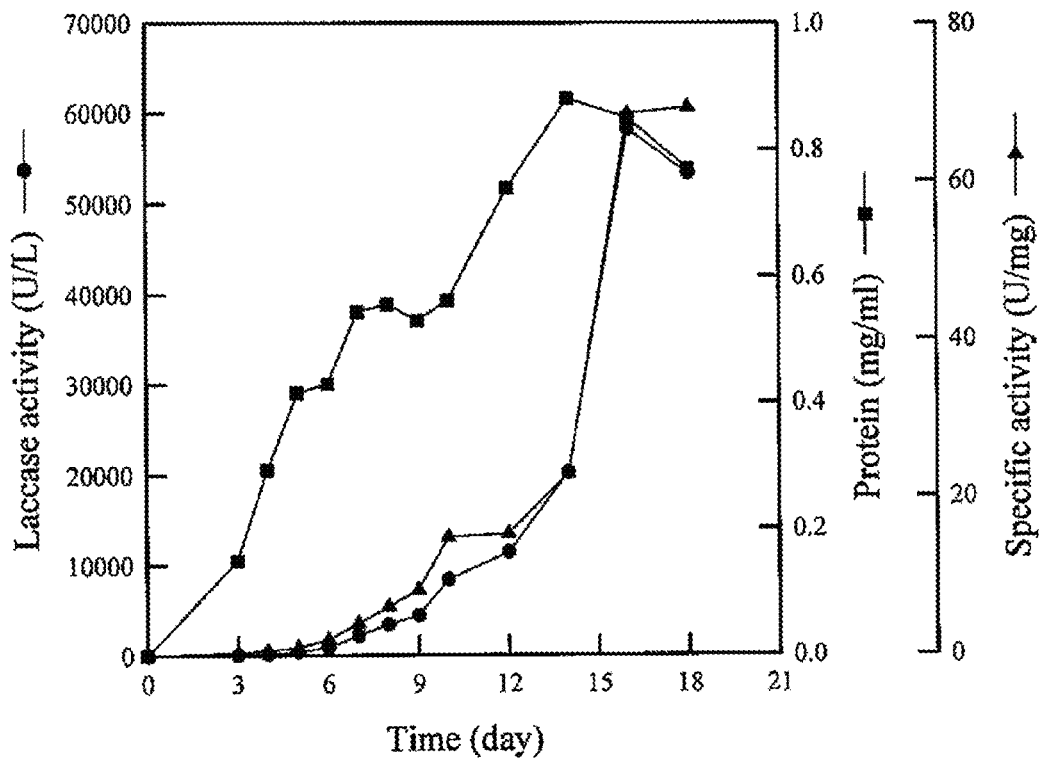
FIG. 7 is a chart showing a time course of laccase activities, protein levels, and specific activities during a 13-day fermentation period of *Lentinus* sp.
Figure 8:
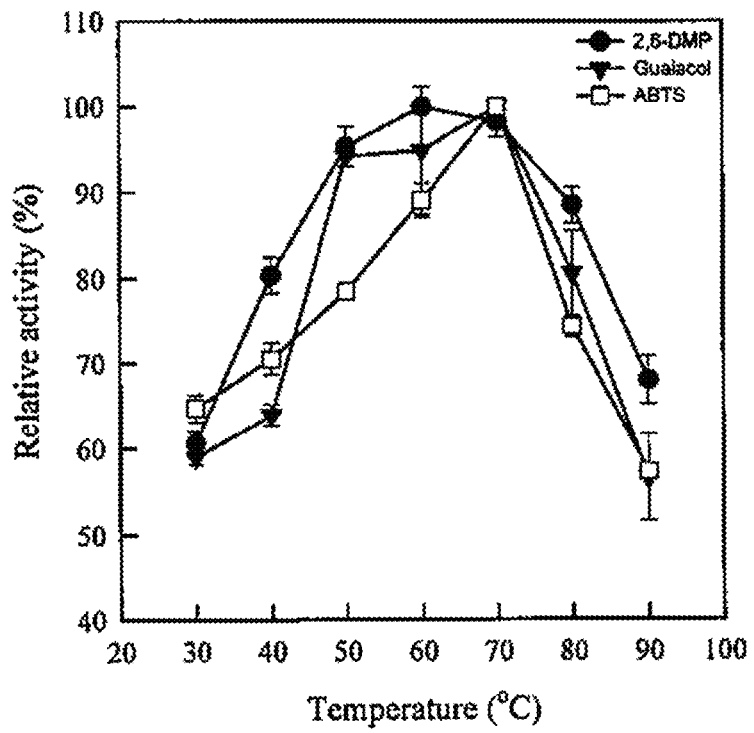
FIG. 8 is a diagram showing the effects of temperature and pH on activity and stability of *Lentinus* sp. laccases. Panel A: effect of temperature on laccase activity; Panel B: effect of temperature on laccase stability; Panel C: effect of pH on laccase activity; Panel D: effect of pH on laccase stability.
Figure 8:
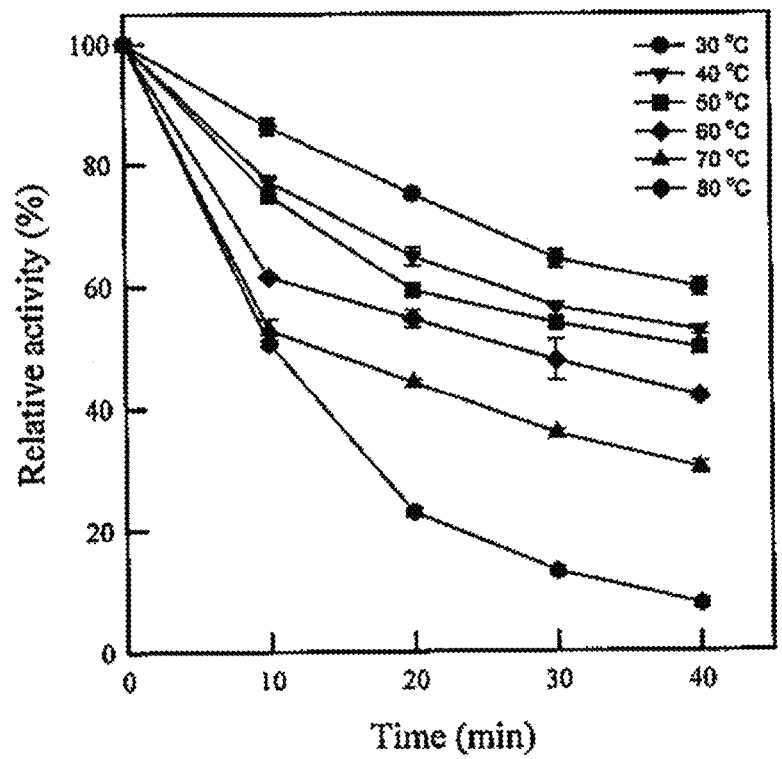
Figure 8:
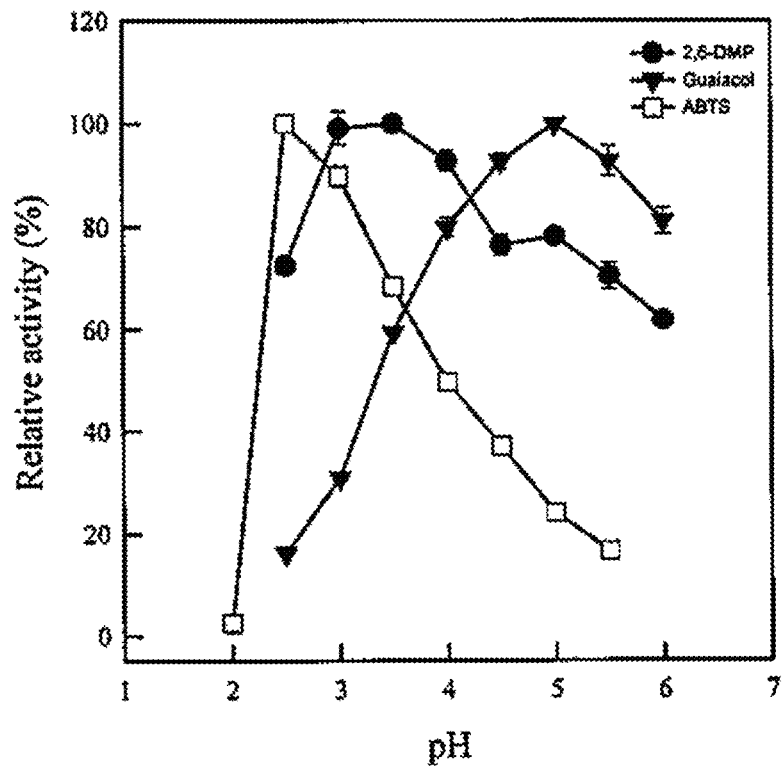
Figure 8:
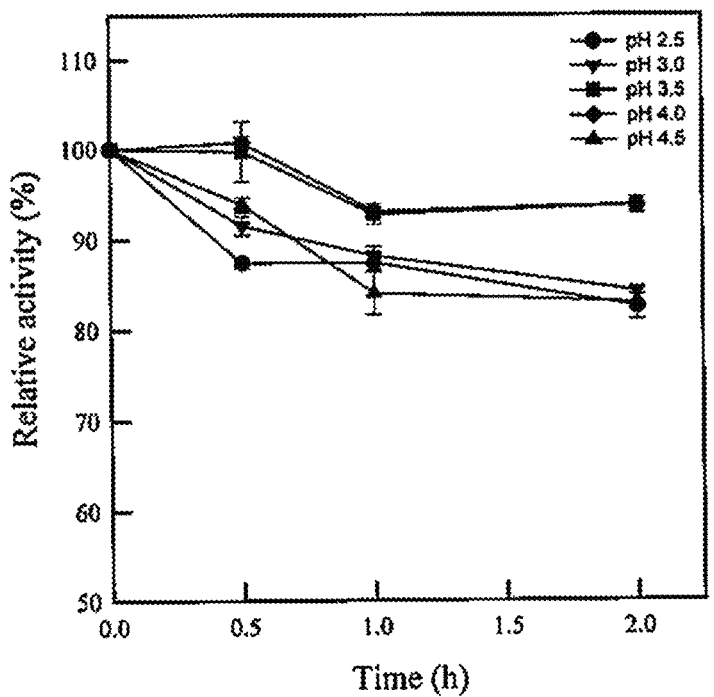

The optimized laccase production in liquid culture of *Lentinus* sp. is shown in FIG. 7. After a 16-day cultivation at 25° C., the laccase activity in the culture medium peaked at approximately 58,273 U/L, and the specific activity in the medium reached around 68.6 U/mg. See FIG. 7. Further, laccase was enriched about 35.1-fold with a 3.6% yield after the anion-exchange and gel-filtration column chromatography. The specific activity of the enriched laccase fraction (with >96% homogeneity) was determined to be 1427.1 U/mg at 30° C. and pH 3.0. The results obtained from the zymography analysis and glycoprotein analysis of the purified *Lentinus* sp. laccase indicate that this enzyme has a molecule weight of 59.1 (glycosylated) and 55.2 kDa (deglycosylated). The glycosylation level in the enzyme was about 6.6%. UV-Vis absorption spectral analysis showed that the purified enzyme has a dominant absorption peak at 600 nm and a broad shoulder absorption at 330 nm, indicating that this enzyme contains both type I and type III copper ions. Results from a DSC assay as described above show that the *Lentinus* sp. laccase denatured at a high temperature, with a midpoint temperature ($T_m$) of 77.1° C.

(iii) Effect of Temperature, pH, and Solvent on Laccase Activity and Stability

To determine the effect of temperature on the enzyme activity, a standard enzymatic activity assay was performed under various temperatures (i.e., 30-90° C.). For thermal stability study, laccase was pre-incubated in a 50 mM citric acid buffer (pH 3.0) at 30-80° C. for 10-40 min and the residual enzymatic activity was then determined by the standard assay. See Example 1 above. Values of $t_{1/2}$ were determined accordingly.

The results show that the optimal temperature for the *Lentinus* sp. laccase was 70° C. when ABTS or guaiacol was used as the substrate and the optimal temperature was 60° C. when 2,6-dimethoxyphenol (2,6-DMP) was used as the substrate. Values of $t_{1/2}$ at 50° C., 60° C., and 70° C. were 30 min, 20 min, and 15 min, respectively. When determined at 30° C. or 40° C., the $t_{1/2}$ value was greater than 40 min. The $t_{1/2}$ of the enzyme incubated at room temperature (25° C.) in 50 mM sodium phosphate buffer was around 118 h.

The effect of pH on laccase activity was investigated at pH 2.0-6.0, using a glycine-HCl buffer (pH 2.0-2.5) or a citric acid buffer (pH 2.5-6.0). To determine protein stability in different pH conditions, the enzyme was pre-incubated at pH 2.5-4.5 at 25° C. for 0-2 h and the residual enzyme activity was determined by the standard enzymatic assay.

The purified *Lentinus* sp. laccase showed a maximal activity at pH 2.5, 3.5, and 5.0 when ABTS, 2,6-DMP, and guaiacol, respectively, were used as the substrates. This enzyme was also found to be very stable under acidic conditions. More specifically, it remained more than 80% of its original activity against ABTS after being incubated at pH 2.5-4.5 for 2 h.

The enzyme stability in the presence of an organic solvent was investigated as follows. The purified *Lentinus* sp. laccase was pre-incubated in 50 mM sodium phosphate buffer (pH 6.0) containing 1%, 10%, or 25% of an organic solvent (i.e., methanol, ethanol, acetonitrile; acetone, and N,N-dimethyl formamide) at room temperature for up to 120 hours. *T. versicolor* (Fluka No. 53739) laccase was used as a reference enzyme in this study. The residual enzymatic activity was determined at different time intervals during the incubation by the standard assay. The results are shown in Table 3 below:

TABLE 3

Effects of various organic solvents on *Lentinus* sp. laccase activity

| Organic solvents | Relative activity (%)* | |
|---|---|---|
| | 1% | 10% |
| Methanol | 101.4 ± 6.4 | 101.0 ± 4.1 |
| Ethanol | 103.6 ± 8.7 | 88.3 ± 3.9 |
| Acetone | 69.2 ± 3.0 | 62.8 ± 2.9 |
| Acetonitrile | 91.8 ± 1.7 | 86.4 ± 6.8 |
| N,N-Dimethylformamide | 79.9 ± 5.0 | 56.3 ± 5.4 |
| Dimethyl sulfoxide | 78.4 ± 6.1 | 1.5 ± 0.8 |

*Assay reactions were performed in 50 mM citric acid buffer (pH 3.0) at 30° C., with ABTS used as the substrate.

The laccase stability after incubation with methanol or ethanol for an extended period was further investigated. The *Lentinus* sp. laccase or the reference laccase was incubated with 1-25% methanol or ethanol in a 50 mM sodium phosphate buffer (pH 6.0) at room temperature for up to 120 hours and enzymatic activities were determined at various time intervals during the incubation, using ABTS as the substrate. Surprisingly, the *Lentinus* sp. laccase showed an increased enzymatic activity (i.e., 149%) 6 hours after incubation with 10% of methanol or ethanol. The enzyme activity of the *Lentinus* sp. laccase maintained as 95% in 25% ethanol while that of the reference laccase reduced to 41%. This result indicates that the *Lentinus* sp. laccase is resistant to ethanol/methanol, rendering it an ideal candidate enzyme for use in the biofuel industry.

(iv) Laccase Kinetics

Kinetic parameters were determined following conventional methods. See also Example 1 above. The results are shown in Table 4 below:

(v) Lignin Degradation and Decoloration Analysis

Figure 9:
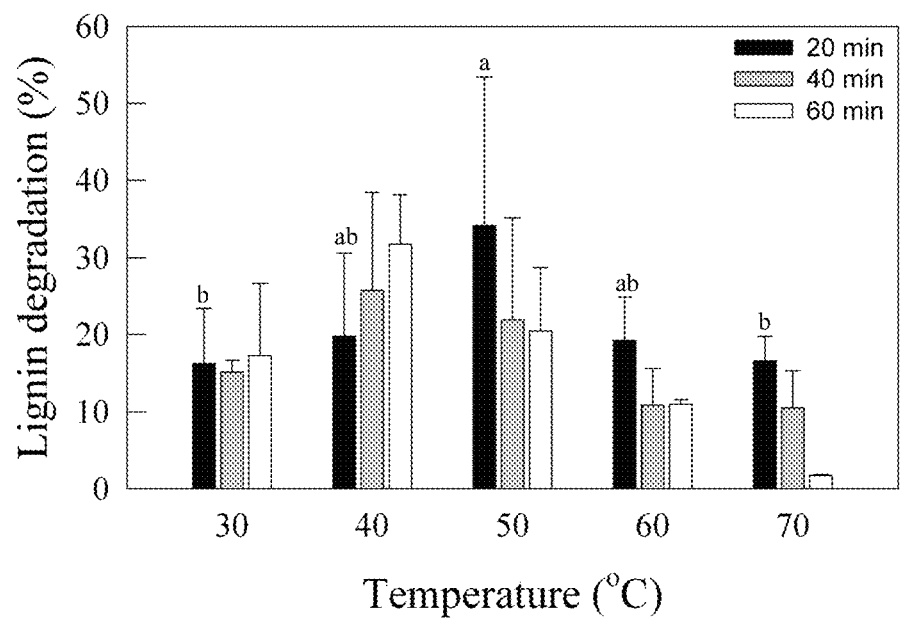
FIG. 9 is a chart showing lignin degradation (panel A) and RBBR decoloration (panel B) by crude laccase fraction from *Lentinus* sp.
Figure 9:
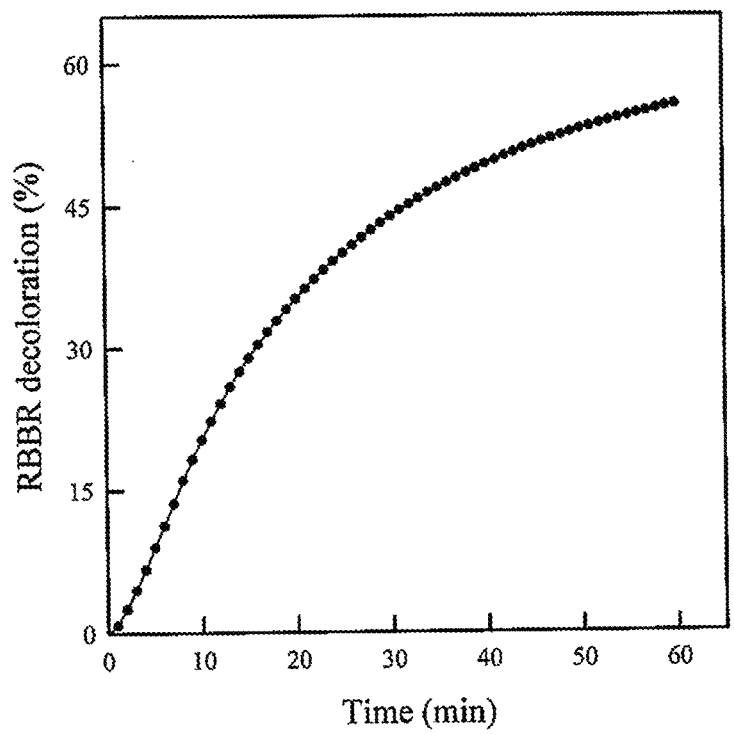

The lignin degradation reaction and the dye decoloration reaction were carried out following the methods described in Example 1 above. The results show that the highest lignin degradation efficiency, i.e., 34.1%, was observed when the reaction was carried out at 50° C. for 20 min. See FIG. 9, pane A. The lignin degradation efficiencies were 22%-25% at 40-50° C. for 40 min and 32% at 40° C. for 60 min. See FIG. 9, panel A. The results also show that the highest RBBR decoloration efficiency is around 47.7%. See FIG. 9, panel B.

(vi) Cloning of Laccase Genes from *Lentinus* sp. and Expressing Laccases in *Pichia*

Total RNAs from *Lentinus* sp. were isolated and cDNAs encoding laccases were amplified via PCR, following the methods described in Example 1 above.

Full-length laccase cDNAs were then amplified using the following specific primers:

```
                                           (SEQ ID NO: 29)
lcc5-1:   5'-GCGACGTGATACCAATCGGCGAGAGTTA-3';

(SEQ ID NO: 30)
lcc5-2:   5'-CCATGCTGAAATCCACAAGTATCCACTG-3';

(SEQ ID NO: 31)
lcc3-1:   5'-CCTAACCTGCGCATCGGCTTCCCCCAGC-3';
and (SEQ ID NO: 32)
lcc3-2:   5'-CGCAAAAACCCTGCGTCCGCATTACCCAGC-3'.
```

Three *Lentinus* sp. laccase genes, designated lccA (SEQ ID NO: 22; GenBank accession no. FJ693715), lccB (SEQ ID NO: 23; GenBank accession no. FJ693716), and lccC (SEQ ID NO: 24; GenBank accession no. GQ220322), were identified. lccA includes 1,566 bp and encodes a polypeptide of 521 amino acid residues (SEQ ID NO:10); lccB gene includes 1,467 bp and encodes a polypeptide of 488 amino acid residues (SEQ ID NO:11); lccC gene includes 1,566 bp and encodes a polypeptide of 521 amino acid residues (SEQ ID NO:12). All of the encoded polypeptides are in precursor form, i.e., including a 21-amino-acid signal peptide at the N-terminus.

TABLE 4

Kinetic properties of laccases from various microorganisms

| Fungal species | Specific activity (U/mg) | $k_{cat}$ (s$^{-1}$) | $K_m$ (μm) | $k_{cat}/K_m$ (s$^{-1}$μM$^{-1}$) | Optimum temperature (° C.) | $t_{1/2}$ (min) |
|---|---|---|---|---|---|---|
| *Lentinus* sp.$^a$ | 2047.1 | 2016.5 | 8.4 | 239.5 | 70 (at pH 2.5) | >40 (at 50° C.) 15 (at 70° C.) |
| *Lentinus* sp.$^b$ | 310.3 | 305.5 | 523.5 | 0.58 | 70 (at pH 5.0) | — |
| *Lentinus* sp.$^c$ | 123.8 | 121.9 | 434.5 | 0.28 | 60 (at pH 3.5) | — |
| *Coriolus versicolor$^a$* (Sigma No. 38837) | 0.3 | — | — | — | 25 (at pH 4.5) | — |
| *Trametes versicolor$^a$* (Fluka No. 53739) | 750 | — | — | — | 50 (at pH 3.0) | 15 (at 50° C.) 5 (at 70° C.) |
| *Melanocarpus* sp.$^a$ (U.S. Pat. No. 7,183,090 B2) | 42.45 | — | — | — | 70 (at pH 6.0) | >360 (at 50° C.) <15 (at 70° C.) |
| *Agaricus blazei$^a$* | 174.6 | 21 | 63 | 0.33 | 25 (at pH 2.3) | >250 (at 25° C.) |
| *Panus tigrinus$^a$* | — | 185.69 | 31 | 5.99 | 30 (at pH 3.5) | 150 (at 25° C.) |
| *Pleurofus sajor-caju$^a$* | 1244.4 | 520.24 | 56 | 9.29 | 40 (at pH 5.0) | — |
| *Pycnoporus sanguineus$^a$* | 340.76 | 1.155 | 77 | 0.015 | 25 (at pH 3.0) | — |
| *Trametes C30 LAC2$^a$* | 934 | 683.33 | 536 | 1.27 | 55 (at pH 5.7) | — |
| *Trametes pubescens LAP2$^a$* | 1100 | 350 | 43 | 8.14 | 25 (at pH 4.0) | — |
| *Trametes versicolor$^a$* | 310.0 | 351.3 | 37.3 | 9.4 | 55 (at pH 4.0) | — |

The full-length *Lentinus* sp. lccA gene was amplified via PCR using primers lcc1-F: 5'-TTCGAAACGAGGAATTC-CCACCATG-3' (SEQ ID NO: 33) and lcc1-R: 5'-TTCTA-GATCCTGATCATCAGAACTG-3' (SEQ ID NO: 34). The PCR product was cloned into the *Pichia* expression vector pPICZB (Invitrogen) via the EcoRI and XbaI cloning sites to obtain an expression plasmid pPICZ-lccA.

pPICZ-lccA was introduced into *Pichia pastoris* strain X-33 host cells (Invitrogen) and positive transformants were selected for LccA expression. Briefly, a positive transformant was cultured in BMMY medium containing 1% yeast extract, 2% peptone, 1.34% yeast nitrogen base, 0.00004% biotin, and 0.5% methanol at 25° C. and 200 rpm for 20 days. Methanol was daily added to reach a final concentration of 0.5%. Within the 20-day cultivation, 1 ml of the supernatant was collected; laccase activity and cell growth were determined.

Figure 10:
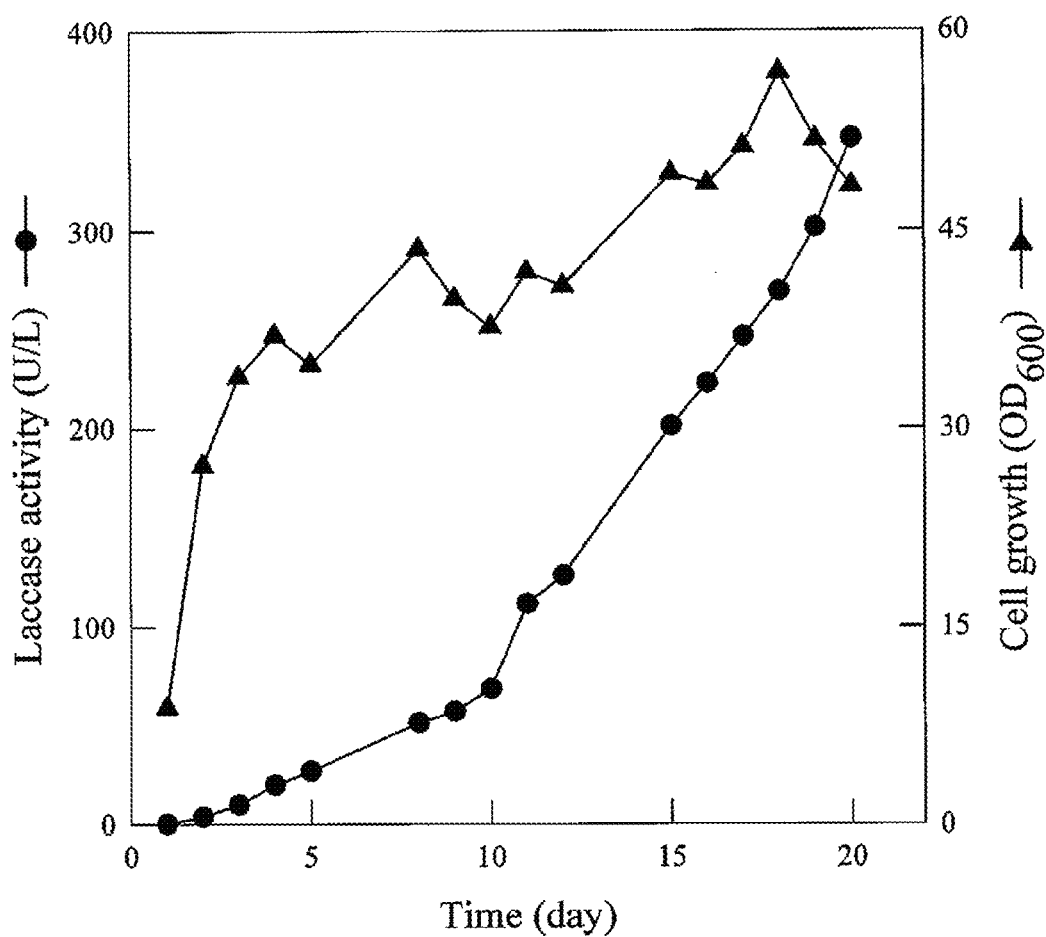
FIG. 10 is a diagram showing production of LccA in *P. pastoris* host cells via recombinant technology and growth curves of the host cells.

As shown in FIG. 10, a high laccase activity (about 400 U/L) was detected in the culture medium after 18-day cultivation, indicating that the expressed LccA was secreted into the medium.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An isolated polypeptide, comprising an amino acid sequence that is at least 95% identical to the sequence of SEQ ID NO:3, the polypeptide having four conserved laccase copper binding sites, wherein the polypeptide exhibits laccase enzymatic activity.

2. The isolated polypeptide of claim 1, comprising an amino acid sequence that is at least 98% identical to the sequence of SEQ ID NO:3.

3. The isolated polypeptide of claim 1, comprising the amino acid sequence of SEQ ID NO:3.

4. The isolated polypeptide of claim 3, comprising the amino acid sequence of SEQ ID NO:9.

5. A method of oxidizing a laccase substrate, comprising contacting the isolated polypeptide of claim 1 with a laccase substrate.

6. The method of claim 5, wherein the substrate is selected from the group consisting of hardwood stem, softwood stem, nut shell, corn cob, paper, straw, sorted refuse, leaf, cotton seeds hair, swine waste, cattle manure, grass, sugar cane bagasse, bamboo, fiber, coffee pulp, banana waste, and yucca waste.

7. The method of claim 5, wherein the substrate is an aromatic dye, an industrial effluent, an environmental contaminant, or a toxic compound.

8. The method of claim 5, wherein the polypeptide contains the amino acid sequence of SEQ ID NO:3.

* * * * *

SEQUENCE LISTING

<160> NUMBER OF SEQ ID NOS: 34

<210> SEQ ID NO 1
<211> LENGTH: 497
<212> TYPE: PRT
<213> ORGANISM: Cerrena sp

<400> SEQUENCE: 1

```
Ala Ile Gly Pro Val Thr Asp Leu Glu Ile Thr Asn Gly Thr Ile Ser
1               5                   10                  15

Pro Asp Gly Tyr Ser Arg Ala Ala Val Leu Ala Gly Gly Ser Phe Pro
            20                  25                  30

Gly Pro Leu Ile Thr Gly Asn Lys Ser Asp Asn Phe Gln Ile Asn Val
        35                  40                  45

Val Asn Ser Leu Ala Asp Ser Asp Met Leu Lys Ser Thr Thr Val His
    50                  55                  60

Trp His Gly Phe Phe Gln Lys Gly Thr Asn Trp Ala Asp Gly Pro Ala
65                  70                  75                  80

Phe Val Asn Gln Cys Pro Ile Ala Thr Gly Asn Ser Phe Leu Tyr Asn
                85                  90                  95

Phe Asn Ala Thr Asp Gln Ala Gly Thr Phe Trp Tyr His Ser His Leu
            100                 105                 110

Glu Thr Gln Tyr Cys Asp Gly Leu Arg Gly Pro Met Val Val Tyr Asp
        115                 120                 125

Pro Asp Pro His Ala Asp Leu Tyr Asp Val Asp Asp Ser Thr
    130                 135                 140

Val Ile Thr Leu Ala Asp Trp Tyr His Thr Leu Ala Arg Leu Gly Ala
145                 150                 155                 160

Ala Phe Pro Thr Ser Asp Ala Thr Leu Ile Asn Gly Leu Gly Arg Tyr
                165                 170                 175

Ser Asp Gly Asn Thr Thr Asp Leu Ala Val Ile Thr Val Glu Ser Gly
            180                 185                 190

Lys Arg Tyr Arg Phe Arg Leu Val Ser Ile Ser Cys Asp Pro Asn Phe
        195                 200                 205

Thr Phe Ser Ile Asp Asn His Thr Met Thr Ile Ile Glu Ala Asp Ala
    210                 215                 220
```

```
Val Asn Tyr Thr Pro Leu Asp Val Asp Glu Ile Gln Ile Phe Ala Gly
225                 230                 235                 240

Gln Arg Tyr Ser Phe Ile Leu Thr Ala Asn Gln Thr Val Asp Asn Tyr
            245                 250                 255

Trp Ile Arg Ala Asp Pro Asn Val Gly Thr Thr Gly Phe Asp Asn Gly
            260                 265                 270

Ile Asn Ser Ala Ile Leu Arg Tyr Ser Gly Ala Asp Glu Val Glu Pro
            275                 280                 285

Thr Thr Asn Gln Thr Thr Ser Thr Asn Pro Leu Val Glu Ala Asn Leu
            290                 295                 300

Val Pro Leu Asp Gly Ala Ala Pro Gly Glu Ala Val Ala Gly Gly
305                 310                 315                 320

Val Asp Tyr Ala Leu Asn Leu Ala Leu Ala Phe Asp Gly Thr Asn Leu
            325                 330                 335

Asp Phe Thr Val Asn Gly Tyr Glu Tyr Thr Ser Pro Thr Val Pro Val
            340                 345                 350

Leu Leu Gln Ile Leu Ser Gly Ala Ser Ser Val Asp Asp Leu Leu Pro
            355                 360                 365

Ser Gly Ser Ile Tyr Ser Leu Pro Ser Asn Ser Thr Ile Glu Leu Ser
            370                 375                 380

Ile Pro Ala Leu Ala Val Gly Ala Pro His Pro Ile His Leu His Gly
385                 390                 395                 400

His Thr Phe Ser Val Val Arg Ser Ala Gly Ser Thr Thr Tyr Asn Tyr
            405                 410                 415

Asp Asn Pro Pro Arg Arg Asp Val Val Ser Ile Gly Thr Ala Thr Asp
            420                 425                 430

Asp Asn Val Thr Ile Arg Phe Thr Thr Asp Asn Pro Gly Pro Trp Phe
            435                 440                 445

Leu His Cys His Ile Asp Phe His Leu Glu Ala Gly Phe Ala Val Val
            450                 455                 460

Phe Ala Glu Asp Phe Asn Asp Thr Ala Ser Ala Asn Thr Val Thr Thr
465                 470                 475                 480

Glu Trp Ser Asp Leu Cys Thr Thr Tyr Asp Ala Leu Ser Ser Asp Asp
            485                 490                 495

Leu

<210> SEQ ID NO 2
<211> LENGTH: 496
<212> TYPE: PRT
<213> ORGANISM: Cerrena sp

<400> SEQUENCE: 2

Ala Ile Gly Pro Val Thr Asp Leu Thr Ile Thr Asn Ala Thr Ile Ser
1               5                   10                  15

Pro Asp Gly Phe Ser Arg Gln Ala Val Leu Ala Gly Val Phe Pro
            20                  25                  30

Gly Pro Leu Ile Thr Gly Asn Lys Gly Asp Asn Phe Gln Ile Asn Val
            35                  40                  45

Val Asn Ser Leu Glu Asn Ser Asp Met Leu Lys Ser Thr Thr Ile His
50                  55                  60

Trp His Gly Phe Phe Gln Lys Gly Thr Asn Trp Ala Asp Gly Pro Ala
65                  70                  75                  80

Phe Val Asn Gln Cys Pro Ile Ala Thr Gly Asn Ser Phe Leu Tyr Asn
            85                  90                  95
```

```
Phe Asn Ala Asp Asp Gln Ala Gly Thr Phe Trp Tyr His Ser His Leu
                100                 105                 110

Ser Thr Gln Tyr Cys Asp Gly Leu Arg Gly Pro Met Val Val Tyr Asp
            115                 120                 125

Pro Asn Asp Pro His Ala Ser Leu Tyr Asp Val Asp Asp Glu Ser Thr
        130                 135                 140

Val Ile Thr Leu Ala Asp Trp Tyr His Thr Leu Ala Arg Leu Gly Ala
145                 150                 155                 160

Ala Phe Pro Thr Ala Asp Ala Thr Leu Ile Asn Gly Leu Gly Arg Tyr
                165                 170                 175

Ser Asp Gly Thr Thr Ser Asp Leu Ala Val Ile Thr Val Glu Ser Gly
            180                 185                 190

Lys Arg Tyr Arg Phe Arg Leu Val Asn Ile Ser Cys Asp Pro Asn Tyr
        195                 200                 205

Thr Phe Ser Ile Asp Asn His Thr Phe Thr Val Ile Glu Val Asp Gly
                210                 215                 220

Val Asn His Ala Ala Leu Asp Val Asp Glu Ile Gln Ile Phe Ala Gly
225                 230                 235                 240

Gln Arg Tyr Ser Phe Val Leu Thr Ala Asn Gln Thr Val Asp Asn Tyr
                245                 250                 255

Trp Ile Arg Ala Asn Pro Asn Leu Gly Thr Thr Gly Phe Asp Asn Gly
            260                 265                 270

Ile Asn Ser Ala Ile Leu Arg Tyr Ser Gly Ala Asn Glu Thr Glu Pro
        275                 280                 285

Thr Thr Thr Gln Thr Thr Ala Thr Ala Ala Leu Ser Glu Ala Ser Leu
                290                 295                 300

Val Pro Leu Glu Asp Pro Ala Ala Pro Gly Glu Ala Val Ala Gly Gly
305                 310                 315                 320

Val Asp Tyr Ala Leu Asn Leu Ala Phe Ala Phe Asp Gly Ala Asn Leu
                325                 330                 335

Asp Phe Thr Val Asn Gly Glu Thr Tyr Val Ser Pro Thr Val Pro Val
            340                 345                 350

Leu Leu Gln Ile Leu Ser Gly Ala Ser Ser Val Ser Asp Leu Leu Pro
        355                 360                 365

Ala Gly Ser Val Tyr Ser Leu Pro Ser Asn Ser Thr Ile Glu Leu Ser
                370                 375                 380

Met Pro Gly Gly Val Val Gly Gly Gly His Pro Leu His Leu His Gly
385                 390                 395                 400

His Ala Phe Ser Val Val Arg Ser Ala Gly Ser Asp Thr Tyr Asn Tyr
                405                 410                 415

Val Asn Pro Pro Arg Arg Asp Val Val Asn Ile Gly Ala Ala Gly Asp
            420                 425                 430

Asn Val Thr Ile Arg Phe Thr Thr Asp Asn Pro Gly Pro Trp Phe Leu
        435                 440                 445

His Cys His Ile Asp Phe His Leu Glu Ala Gly Phe Ala Val Val Phe
                450                 455                 460

Ala Glu Asp Phe Asn Ala Thr Ala Ser Ser Asn Thr Val Thr Thr Glu
465                 470                 475                 480

Trp Ser Asn Leu Cys Thr Thr Tyr Asp Ala Leu Ser Ala Asp Asp Gln
                485                 490                 495

<210> SEQ ID NO 3
<211> LENGTH: 495
<212> TYPE: PRT
<213> ORGANISM: Cerrena sp
```

-continued

```
<400> SEQUENCE: 3

Ala Ile Gly Pro Val Ala Asp Leu His Ile Thr Asp Ala Asn Val Ser
1               5                   10                  15

Pro Asp Gly Phe Thr Arg Pro Ala Val Leu Ala Gly Gly Thr Phe Pro
            20                  25                  30

Gly Pro Leu Ile Thr Gly Lys Gln Gly Asp Asn Phe Gln Ile Asn Val
        35                  40                  45

Ile Asp Glu Leu Thr Asp Ala Thr Met Leu Lys Ser Thr Ser Ile His
    50                  55                  60

Trp His Gly Ile Phe Gln Lys Gly Thr Asn Trp Ala Asp Gly Pro Ser
65                  70                  75                  80

Phe Val Asn Gln Cys Pro Ile Thr Thr Gly Asn Ser Phe Leu Tyr Asp
                85                  90                  95

Phe Ser Val Pro Asp Gln Thr Gly Thr Tyr Trp Tyr His Ser His Leu
            100                 105                 110

Ser Thr Gln Tyr Cys Asp Gly Leu Arg Gly Ala Leu Val Ile Tyr Asp
        115                 120                 125

Asp Asn Asp Pro His Lys Asp Leu Tyr Asp Val Asp Asp Glu Thr Thr
    130                 135                 140

Val Ile Thr Leu Ala Asp Trp Tyr His Thr Gln Ala Arg Leu Ile Thr
145                 150                 155                 160

Gly Val Pro Val Ser Asp Ala Thr Leu Ile Asn Gly Leu Gly Arg Tyr
                165                 170                 175

Leu Asn Gly Pro Thr Asp Ala Pro Leu Ala Val Ile Thr Val Asp Gln
            180                 185                 190

Gly Lys Arg Tyr Arg Phe Arg Leu Val Ser Ile Ser Cys Asp Pro Asn
        195                 200                 205

Phe Val Phe Ser Ile Asp Asn His Ser Met Thr Val Ile Glu Val Asp
    210                 215                 220

Ala Val Asn Ser Gln Pro Leu Val Val Asp Ser Ile Gln Ile Phe Ala
225                 230                 235                 240

Ala Gln Arg Tyr Ser Phe Ile Leu Asn Ala Asn Gln Ser Val Gly Asn
                245                 250                 255

Tyr Trp Ile Arg Ala Asn Pro Asn Leu Gly Asn Thr Gly Phe Thr Asn
            260                 265                 270

Gly Ile Asn Ser Ala Ile Leu Arg Tyr Asn Gly Ala Pro Val Ala Glu
        275                 280                 285

Pro Asn Thr Thr Gln Thr Ala Ser Thr Asn Pro Leu Asn Glu Val Asn
    290                 295                 300

Leu His Pro Leu Val Pro Thr Pro Val Pro Gly Thr Pro Gln Pro Gly
305                 310                 315                 320

Gly Val Asp Val Val Gln Asn Leu Val Leu Gly Phe Ser Gly Gly Lys
                325                 330                 335

Phe Thr Ile Asn Gly Val Ala Phe Ser Pro Thr Val Pro Val Leu
            340                 345                 350

Leu Gln Ile Leu Ser Gly Thr Thr Thr Ala Gln Asp Leu Leu Pro Thr
        355                 360                 365

Gly Ser Ile Ile Glu Leu Pro Leu Gly Lys Thr Val Glu Leu Thr Leu
    370                 375                 380

Ala Ala Gly Val Leu Gly Gly Pro His Pro Phe His Leu His Gly His
385                 390                 395                 400

Thr Phe His Val Val Arg Ser Ala Gly Gln Thr Thr Pro Asn Tyr Val
                405                 410                 415
```

-continued

Asp Pro Ile Leu Arg Asp Thr Val Asn Thr Gly Ala Ala Gly Asp Asn
            420                 425                 430

Val Thr Ile Arg Phe Thr Thr Asp Asn Pro Gly Pro Trp Phe Leu His
            435                 440                 445

Cys His Ile Asp Trp His Leu Glu Ala Gly Phe Ala Val Val Phe Ala
            450                 455                 460

Glu Gly Leu Asn Gln Thr Asn Ala Ala Asn Pro Thr Pro Asp Ala Trp
465                 470                 475                 480

Asn Asn Leu Cys Asp Leu Tyr Asn Ala Leu Pro Ala Gly Asp Gln
            485                 490                 495

<210> SEQ ID NO 4
<211> LENGTH: 500
<212> TYPE: PRT
<213> ORGANISM: Lentinus sp

<400> SEQUENCE: 4

Gly Ile Gly Pro Ile Ala Ser Leu Val Val Thr Asp Ala Gln Ile Ser
1               5                   10                  15

Pro Asp Gly Tyr Leu Arg Asp Ala Ile Val Thr Asn Gly Val Phe Pro
            20                  25                  30

Ala Pro Leu Ile Thr Gly Arg Lys Gly Asp His Phe Gln Leu Asn Val
            35                  40                  45

Val Asp Ser Met Thr Asn His Thr Met Leu Lys Ser Thr Ile His
50                  55                  60

Trp His Gly Phe Phe Gln Lys Gly Thr Asn Trp Ala Asp Gly Pro Ala
65                  70                  75                  80

Phe Val Asn Gln Cys Pro Ile Ser Ser Gly His Ser Phe Leu Tyr Asp
            85                  90                  95

Phe His Val Pro Asp Gln Ala Gly Thr Phe Trp Tyr His Ser His Leu
            100                 105                 110

Ser Thr Gln Tyr Cys Asp Gly Leu Arg Gly Pro Met Val Val Tyr Asp
            115                 120                 125

Pro Asn Asp Pro His Ala Asn Leu Tyr Asp Ile Asp Asn Asp Ser Thr
            130                 135                 140

Val Ile Thr Leu Ala Asp Trp Tyr His Val Ala Ala Lys Leu Gly Pro
145                 150                 155                 160

Arg Phe Pro Leu Gly Ala Asp Ala Thr Leu Ile Asn Gly Lys Gly Arg
            165                 170                 175

Ser Pro Ala Thr Pro Thr Ala Ala Leu Ser Val Ile Asn Val Val Lys
            180                 185                 190

Gly Lys Arg Tyr Arg Phe Arg Leu Val Ser Ile Ser Cys Asp Pro Asn
            195                 200                 205

Tyr Val Phe Ser Ile Asp Asn His Thr Met Thr Val Ile Glu Ala Asp
            210                 215                 220

Thr Val Asn Thr Gln Pro Leu Ala Val Asp Ser Ile Gln Ile Phe Ala
225                 230                 235                 240

Ala Gln Arg Tyr Ser Phe Ile Leu Asn Ala Asn Gln Pro Val Asp Asn
            245                 250                 255

Tyr Trp Ile Arg Ala Asn Pro Asn Phe Gly Asn Val Gly Phe Thr Asp
            260                 265                 270

Gly Ile Asn Ser Ala Ile Leu Arg Tyr Thr Gly Ala Ala Leu Val Glu
            275                 280                 285

Pro Ser Ala Thr Thr Ala Pro Thr Leu Ser Asn Pro Leu Val Glu Thr
            290                 295                 300

```
Asn Leu His Pro Leu Ala Pro Met Pro Val Pro Gly Gln Pro Val Ser
305                 310                 315                 320

Gly Gly Val Asp Lys Ala Ile Asn Phe Ala Phe Asn Phe Asp Gly Thr
            325                 330                 335

Asp Phe Phe Ile Asn Gly Ala Ser Phe Val Pro Pro Thr Val Pro Val
                340                 345                 350

Leu Leu Gln Ile Met Ser Gly Ala Ser Thr Ala Gln Asp Leu Leu Pro
            355                 360                 365

Ser Gly Ser Val Tyr Pro Leu Pro Ser Asn Ala Thr Ile Glu Leu Ser
        370                 375                 380

Phe Pro Ala Thr Ala Ala Ala Pro Gly Ala Pro His Pro Phe His Leu
385                 390                 395                 400

His Gly His Val Phe Ala Val Val Arg Ser Ala Gly Ser Thr Thr Tyr
                405                 410                 415

Asn Tyr Asn Asn Pro Ile Trp Arg Asp Val Val Ser Thr Gly Thr Pro
            420                 425                 430

Ala Ala Gly Asp Asn Val Thr Ile Arg Phe Ser Thr Asn Asn Pro Gly
        435                 440                 445

Pro Trp Phe Leu His Cys His Ile Asp Phe His Leu Glu Ala Gly Phe
    450                 455                 460

Ala Val Val Met Ala Glu Asp Val Pro Asp Ile Pro Ser Ala Asn Pro
465                 470                 475                 480

Val Pro Gln Ala Trp Ser Asn Leu Cys Pro Thr Tyr Asn Ala Leu Ser
                485                 490                 495

Ser Asp Asp Gln
            500

<210> SEQ ID NO 5
<211> LENGTH: 467
<212> TYPE: PRT
<213> ORGANISM: Lentinus sp

<400> SEQUENCE: 5

Gly Ile Gly Pro Ile Ala Ser Leu Val Val Thr Asp Ala Gln Ile Ser
1               5                   10                  15

Pro Asp Gly Tyr Leu Arg Asp Ala Ile Val Thr Asn Gly Val Phe Pro
            20                  25                  30

Ala Pro Leu Ile Thr Gly Arg Lys Gly Asp His Phe Gln Leu Asn Val
        35                  40                  45

Val Asp Ser Met Thr Asn His Thr Met Leu Lys Ser Thr Ser Ile His
50                  55                  60

Trp His Gly Phe Phe Gln Lys Gly Thr Asn Trp Ala Asp Gly Pro Ala
65                  70                  75                  80

Phe Val Asn Gln Cys Pro Ile Ser Ser Gly His Ser Phe Leu Tyr Asp
                85                  90                  95

Phe His Val Pro Asp Gln Ala Gly Thr Phe Trp Tyr His Ser His Leu
            100                 105                 110

Ser Thr Gln Tyr Cys Asp Gly Leu Arg Gly Pro Met Val Val Tyr Asp
        115                 120                 125

Pro Asn Asp Pro His Ala Asn Leu Tyr Asp Ile Asp Asn Asp Ser Thr
130                 135                 140

Val Ile Thr Leu Ala Asp Trp Tyr His Val Ala Ala Lys Leu Gly Pro
145                 150                 155                 160

Arg Phe Pro Leu Gly Ala Asp Ala Thr Leu Ile Asn Gly Lys Gly Arg
                165                 170                 175
```

```
Ser Pro Ala Thr Pro Thr Ala Ala Leu Ser Val Ile Asn Val Val Lys
            180                 185                 190

Gly Lys Arg Tyr Arg Phe Arg Leu Val Ser Ile Ser Cys Asp Pro Asn
        195                 200                 205

Tyr Val Phe Ser Ile Asp Asn His Thr Met Thr Val Ile Glu Ala Asp
    210                 215                 220

Thr Val Asn Thr Gln Pro Leu Ala Val Asp Ser Ile Gln Ile Phe Ala
225                 230                 235                 240

Ala Gln Arg Tyr Ser Phe Ile Leu Asn Ala Asn Gln Pro Val Asp Asn
            245                 250                 255

Tyr Trp Ile Arg Ala Asn Pro Asn Phe Gly Asn Val Gly Phe Thr Asp
        260                 265                 270

Gly Ile Asn Ser Ala Ile Leu Arg Tyr Thr Gly Ala Ala Leu Val Glu
    275                 280                 285

Pro Ser Ala Thr Thr Ala Pro Thr Leu Ser Asn Pro Leu Val Glu Thr
290                 295                 300

Asn Leu His Pro Leu Ala Pro Met Pro Val Pro Gly Gln Pro Val Ser
305                 310                 315                 320

Gly Gly Val Asp Lys Ala Ile Asn Phe Ala Phe Asn Phe Asp Gly Thr
            325                 330                 335

Asp Phe Phe Ile Asn Gly Ala Ser Phe Val Pro Pro Thr Val Pro Val
        340                 345                 350

Leu Leu Gln Ile Met Ser Gly Ala Ser Thr Ala Gln Asp Leu Leu Pro
    355                 360                 365

Ser Gly Ser Val Tyr Pro Leu Pro Ser Asn Ala Thr Ile Glu Leu Ser
370                 375                 380

Phe Pro Ala Thr Ala Ala Pro Gly Ala Pro His Pro Phe His Leu
385                 390                 395                 400

His Gly His Val Phe Ala Val Val Arg Ser Ala Gly Ser Thr Thr Tyr
            405                 410                 415

Asn Tyr Asn Asn Pro Ile Trp Arg Asp Val Val Ser Thr Gly Thr Pro
        420                 425                 430

Ala Ala Gly Asp Asn Val Thr Ile Arg Phe Ser Thr Asn Asn Pro Gly
    435                 440                 445

Pro Trp Phe Leu His Cys His Ile Asp Phe His Leu Glu Ala Gly Phe
450                 455                 460

Ala Val Val
465

<210> SEQ ID NO 6
<211> LENGTH: 500
<212> TYPE: PRT
<213> ORGANISM: Lentinus sp

<400> SEQUENCE: 6

Ala Ile Gly Pro Val Ala Asp Leu Thr Ile Ser Asn Ala Gln Val Ser
1               5                  10                  15

Pro Asp Gly Phe Leu Arg Asp Ala Val Val Thr Asn Gly Leu Val Pro
            20                  25                  30

Gly Pro Leu Ile Thr Gly Asn Lys Gly Asp Arg Phe Gln Leu Asn Val
        35                  40                  45

Ile Asp Gln Met Thr Asn His Thr Met Leu Lys Thr Thr Ser Ile His
    50                  55                  60

Trp His Gly Phe Phe Gln Lys Gly Thr Asn Trp Ala Asp Gly Pro Ala
65              70                  75                  80
```

-continued

Phe Val Asn Gln Cys Pro Ile Ala Ser Gly Asn Ser Phe Leu Tyr Asp
                85                  90                  95

Phe Gln Val Pro Asp Gln Ala Gly Thr Phe Trp Tyr His Ser His Leu
            100                 105                 110

Ser Thr Gln Tyr Cys Asp Gly Leu Arg Gly Pro Leu Val Val Tyr Asp
            115                 120                 125

Pro Asn Asp Pro His Ala Ala Leu Tyr Asp Ile Asp Asp Asp Asn Thr
        130                 135                 140

Val Ile Thr Leu Thr Asp Trp Tyr His Thr Ala Ala Arg Leu Gly Pro
145                 150                 155                 160

Arg Phe Pro Leu Gly Ala Asp Ala Thr Leu Ile Asn Gly Leu Gly Arg
                165                 170                 175

Ser Pro Ala Thr Pro Thr Ala Asn Leu Thr Val Ile Asn Val Thr Gln
            180                 185                 190

Gly Lys Arg Tyr Arg Phe Arg Leu Val Ser Ile Ser Cys Asp Pro Asn
        195                 200                 205

Tyr Val Phe Ser Ile Asp Asn His Thr Met Ser Val Ile Glu Thr Asp
        210                 215                 220

Thr Val Asn Thr Gln Pro Leu Thr Val Asp Ser Ile Gln Ile Tyr Ala
225                 230                 235                 240

Ala Gln Arg Tyr Ser Phe Val Leu Thr Ala Asn Gln Ser Val Asp Asn
                245                 250                 255

Tyr Trp Ile Arg Ala Asn Pro Asn Phe Gly Asn Val Gly Phe Thr Asp
                260                 265                 270

Ala Ile Asn Ser Ala Ile Leu Arg Tyr Asp Gly Ala Pro Asp Ala Glu
        275                 280                 285

Pro Ser Ala Thr Thr Ala Pro Thr Leu Thr Asn Pro Leu Val Glu Ala
        290                 295                 300

Asn Leu His Pro Leu Ala Ser Met Pro Val Pro Gly Ser Pro Val Ser
305                 310                 315                 320

Gly Gly Val Asp Lys Ala Ile Asn Phe Val Phe Asn Phe Asn Gly Thr
                325                 330                 335

Asn Phe Ser Ile Asn Asn Ala Thr Phe Val Pro Pro Thr Val Pro Val
            340                 345                 350

Leu Leu Gln Ile Met Ser Gly Ala Asn Thr Ala Gln Asp Leu Leu Pro
            355                 360                 365

Ser Gly Ser Val Tyr Thr Leu Pro Ser Asn Ala Thr Ile Glu Leu Ser
        370                 375                 380

Phe Pro Ala Thr Ser Asn Ala Pro Gly Ala Pro His Pro Phe His Leu
385                 390                 395                 400

His Gly His Val Phe Ala Val Val Arg Ser Ala Gly Ser Thr Val Tyr
                405                 410                 415

Asn Tyr Asp Asn Pro Ile Trp Arg Asp Val Val Ser Thr Gly Thr Pro
            420                 425                 430

Ala Ala Gly Asp Asn Val Thr Ile Arg Phe Gln Thr Asn Asn Pro Gly
        435                 440                 445

Pro Trp Phe Leu His Cys His Ile Asp Phe His Leu Asp Ala Gly Phe
        450                 455                 460

Ala Val Val Met Ala Glu Asp Pro Val Asp Thr Pro Thr Ala Asp Pro
465                 470                 475                 480

Val Pro Gln Ala Trp Ser Asp Leu Cys Pro Thr Tyr Asp Ala Leu Ser
                485                 490                 495

Val Asp Asp Gln

<210> SEQ ID NO 7
<211> LENGTH: 518
<212> TYPE: PRT
<213> ORGANISM: Cerrena sp

<400> SEQUENCE: 7

```
Met Leu Asn Phe Asn Ser Leu Ser Thr Phe Ala Val Leu Ala Leu Ser
1               5                   10                  15

Met Arg Ala Asn Ala Ala Ile Gly Pro Val Thr Asp Leu Glu Ile Thr
            20                  25                  30

Asn Gly Thr Ile Ser Pro Asp Gly Tyr Ser Arg Ala Ala Val Leu Ala
        35                  40                  45

Gly Gly Ser Phe Pro Gly Pro Leu Ile Thr Gly Asn Lys Ser Asp Asn
50                  55                  60

Phe Gln Ile Asn Val Val Asn Ser Leu Ala Asp Ser Asp Met Leu Lys
65                  70                  75                  80

Ser Thr Thr Val His Trp His Gly Phe Phe Gln Lys Gly Thr Asn Trp
            85                  90                  95

Ala Asp Gly Pro Ala Phe Val Asn Gln Cys Pro Ile Ala Thr Gly Asn
            100                 105                 110

Ser Phe Leu Tyr Asn Phe Asn Ala Thr Asp Gln Ala Gly Thr Phe Trp
        115                 120                 125

Tyr His Ser His Leu Glu Thr Gln Tyr Cys Asp Gly Leu Arg Gly Pro
    130                 135                 140

Met Val Val Tyr Asp Pro Asp Pro His Ala Asp Leu Tyr Asp Val
145                 150                 155                 160

Asp Asp Asp Ser Thr Val Ile Thr Leu Ala Asp Trp Tyr His Thr Leu
            165                 170                 175

Ala Arg Leu Gly Ala Ala Phe Pro Thr Ser Asp Ala Thr Leu Ile Asn
            180                 185                 190

Gly Leu Gly Arg Tyr Ser Asp Gly Asn Thr Thr Asp Leu Ala Val Ile
        195                 200                 205

Thr Val Glu Ser Gly Lys Arg Tyr Arg Phe Arg Leu Val Ser Ile Ser
    210                 215                 220

Cys Asp Pro Asn Phe Thr Phe Ser Ile Asp Asn His Thr Met Thr Ile
225                 230                 235                 240

Ile Glu Ala Asp Ala Val Asn Tyr Thr Pro Leu Asp Val Asp Glu Ile
            245                 250                 255

Gln Ile Phe Ala Gly Gln Arg Tyr Ser Phe Ile Leu Thr Ala Asn Gln
        260                 265                 270

Thr Val Asp Asn Tyr Trp Ile Arg Ala Asp Pro Asn Val Gly Thr Thr
    275                 280                 285

Gly Phe Asp Asn Gly Ile Asn Ser Ala Ile Leu Arg Tyr Ser Gly Ala
290                 295                 300

Asp Glu Val Glu Pro Thr Thr Asn Gln Thr Thr Ser Thr Asn Pro Leu
305                 310                 315                 320

Val Glu Ala Asn Leu Val Pro Leu Asp Gly Ala Ala Pro Gly Glu
            325                 330                 335

Ala Val Ala Gly Gly Val Asp Tyr Ala Leu Asn Leu Ala Leu Ala Phe
            340                 345                 350

Asp Gly Thr Asn Leu Asp Phe Thr Val Asn Gly Tyr Glu Tyr Thr Ser
        355                 360                 365

Pro Thr Val Pro Val Leu Leu Gln Ile Leu Ser Gly Ala Ser Ser Val
```

```
                370                 375                 380
Asp Asp Leu Leu Pro Ser Gly Ser Ile Tyr Ser Leu Pro Ser Asn Ser
385                 390                 395                 400

Thr Ile Glu Leu Ser Ile Pro Ala Leu Ala Val Gly Ala Pro His Pro
                405                 410                 415

Ile His Leu His Gly His Thr Phe Ser Val Val Arg Ser Ala Gly Ser
                420                 425                 430

Thr Thr Tyr Asn Tyr Asp Asn Pro Pro Arg Arg Asp Val Val Ser Ile
                435                 440                 445

Gly Thr Ala Thr Asp Asp Asn Val Thr Ile Arg Phe Thr Thr Asp Asn
450                 455                 460

Pro Gly Pro Trp Phe Leu His Cys His Ile Asp Phe His Leu Glu Ala
465                 470                 475                 480

Gly Phe Ala Val Val Phe Ala Glu Asp Phe Asn Asp Thr Ala Ser Ala
                485                 490                 495

Asn Thr Val Thr Thr Glu Trp Ser Asp Leu Cys Thr Thr Tyr Asp Ala
                500                 505                 510

Leu Ser Ser Asp Asp Leu
            515

<210> SEQ ID NO 8
<211> LENGTH: 517
<212> TYPE: PRT
<213> ORGANISM: Cerrena sp

<400> SEQUENCE: 8

Met Ile Asn Phe Asn Ser Leu Leu Thr Phe Thr Val Leu Ala Leu Ser
1               5                   10                  15

Met Arg Ala His Ala Ala Ile Gly Pro Val Thr Asp Leu Thr Ile Thr
                20                  25                  30

Asn Ala Thr Ile Ser Pro Asp Gly Phe Ser Arg Gln Ala Val Leu Ala
            35                  40                  45

Gly Gly Val Phe Pro Gly Pro Leu Ile Thr Gly Asn Lys Gly Asp Asn
        50                  55                  60

Phe Gln Ile Asn Val Val Asn Ser Leu Glu Asn Ser Asp Met Leu Lys
65                  70                  75                  80

Ser Thr Thr Ile His Trp His Gly Phe Phe Gln Lys Gly Thr Asn Trp
                85                  90                  95

Ala Asp Gly Pro Ala Phe Val Asn Gln Cys Pro Ile Ala Thr Gly Asn
                100                 105                 110

Ser Phe Leu Tyr Asn Phe Asn Ala Asp Asp Gln Ala Gly Thr Phe Trp
            115                 120                 125

Tyr His Ser His Leu Ser Thr Gln Tyr Cys Asp Gly Leu Arg Gly Pro
        130                 135                 140

Met Val Val Tyr Asp Pro Asn Asp Pro His Ala Ser Leu Tyr Asp Val
145                 150                 155                 160

Asp Asp Glu Ser Thr Val Ile Thr Leu Ala Asp Trp Tyr His Thr Leu
                165                 170                 175

Ala Arg Leu Gly Ala Ala Phe Pro Thr Ala Asp Ala Thr Leu Ile Asn
                180                 185                 190

Gly Leu Gly Arg Tyr Ser Asp Gly Thr Thr Ser Asp Leu Ala Val Ile
            195                 200                 205

Thr Val Glu Ser Gly Lys Arg Tyr Arg Phe Arg Leu Val Asn Ile Ser
        210                 215                 220

Cys Asp Pro Asn Tyr Thr Phe Ser Ile Asp Asn His Thr Phe Thr Val
```

-continued

```
            225                 230                 235                 240

Ile Glu Val Asp Gly Val Asn His Ala Ala Leu Asp Val Asp Glu Ile
                245                 250                 255

Gln Ile Phe Ala Gly Gln Arg Tyr Ser Phe Val Leu Thr Ala Asn Gln
            260                 265                 270

Thr Val Asp Asn Tyr Trp Ile Arg Ala Asn Pro Asn Leu Gly Thr Thr
        275                 280                 285

Gly Phe Asp Asn Gly Ile Asn Ser Ala Ile Leu Arg Tyr Ser Gly Ala
    290                 295                 300

Asn Glu Thr Glu Pro Thr Thr Thr Gln Thr Thr Ala Thr Ala Ala Leu
305                 310                 315                 320

Ser Glu Ala Ser Leu Val Pro Leu Glu Asp Pro Ala Ala Pro Gly Glu
                325                 330                 335

Ala Val Ala Gly Gly Val Asp Tyr Ala Leu Asn Leu Ala Phe Ala Phe
            340                 345                 350

Asp Gly Ala Asn Leu Asp Phe Thr Val Asn Gly Glu Thr Tyr Val Ser
        355                 360                 365

Pro Thr Val Pro Val Leu Leu Gln Ile Leu Ser Gly Ala Ser Ser Val
    370                 375                 380

Ser Asp Leu Leu Pro Ala Gly Ser Val Tyr Ser Leu Pro Ser Asn Ser
385                 390                 395                 400

Thr Ile Glu Leu Ser Met Pro Gly Gly Val Val Gly Gly His Pro
                405                 410                 415

Leu His Leu His Gly His Ala Phe Ser Val Val Arg Ser Ala Gly Ser
            420                 425                 430

Asp Thr Tyr Asn Tyr Val Asn Pro Arg Arg Asp Val Val Asn Ile
        435                 440                 445

Gly Ala Ala Gly Asp Asn Val Thr Ile Arg Phe Thr Thr Asp Asn Pro
    450                 455                 460

Gly Pro Trp Phe Leu His Cys His Ile Asp Phe His Leu Glu Ala Gly
465                 470                 475                 480

Phe Ala Val Val Phe Ala Glu Asp Phe Asn Ala Thr Ala Ser Ser Asn
                485                 490                 495

Thr Val Thr Thr Glu Trp Ser Asn Leu Cys Thr Thr Tyr Asp Ala Leu
            500                 505                 510

Ser Ala Asp Asp Gln
            515

<210> SEQ ID NO 9
<211> LENGTH: 516
<212> TYPE: PRT
<213> ORGANISM: Cerrena sp

<400> SEQUENCE: 9

Met Ala Phe Arg Thr Gly Phe Ser Ala Phe Ile Ser Leu Ser Leu Ala
1               5                   10                  15

Leu Gly Ala Leu Ala Ala Ile Gly Pro Val Ala Asp Leu His Ile Thr
            20                  25                  30

Asp Ala Asn Val Ser Pro Asp Gly Phe Thr Arg Pro Ala Val Leu Ala
        35                  40                  45

Gly Gly Thr Phe Pro Gly Pro Leu Ile Thr Gly Lys Gln Gly Asp Asn
    50                  55                  60

Phe Gln Ile Asn Val Ile Asp Glu Leu Thr Asp Ala Thr Met Leu Lys
65                  70                  75                  80

Ser Thr Ser Ile His Trp His Gly Ile Phe Gln Lys Gly Thr Asn Trp
```

-continued

```
                85                  90                  95
Ala Asp Gly Pro Ser Phe Val Asn Gln Cys Pro Ile Thr Thr Gly Asn
            100                 105                 110

Ser Phe Leu Tyr Asp Phe Ser Val Pro Asp Gln Thr Gly Thr Tyr Trp
            115                 120                 125

Tyr His Ser His Leu Ser Thr Gln Tyr Cys Asp Gly Leu Arg Gly Ala
            130                 135                 140

Leu Val Ile Tyr Asp Asn Asp Pro His Lys Asp Leu Tyr Asp Val
145                 150                 155                 160

Asp Asp Glu Thr Thr Val Ile Thr Leu Ala Asp Trp Tyr His Thr Gln
                165                 170                 175

Ala Arg Leu Ile Thr Gly Val Pro Val Ser Asp Ala Thr Leu Ile Asn
            180                 185                 190

Gly Leu Gly Arg Tyr Leu Asn Gly Pro Thr Asp Ala Pro Leu Ala Val
            195                 200                 205

Ile Thr Val Asp Gln Gly Lys Arg Tyr Arg Phe Arg Leu Val Ser Ile
            210                 215                 220

Ser Cys Asp Pro Asn Phe Val Phe Ser Ile Asp Asn His Ser Met Thr
225                 230                 235                 240

Val Ile Glu Val Asp Ala Val Asn Ser Gln Pro Leu Val Val Asp Ser
                245                 250                 255

Ile Gln Ile Phe Ala Ala Gln Arg Tyr Ser Phe Ile Leu Asn Ala Asn
            260                 265                 270

Gln Ser Val Gly Asn Tyr Trp Ile Arg Ala Asn Pro Asn Leu Gly Asn
            275                 280                 285

Thr Gly Phe Thr Asn Gly Ile Asn Ser Ala Ile Leu Arg Tyr Asn Gly
            290                 295                 300

Ala Pro Val Ala Glu Pro Asn Thr Thr Gln Thr Ala Ser Thr Asn Pro
305                 310                 315                 320

Leu Asn Glu Val Asn Leu His Pro Leu Val Pro Thr Pro Val Pro Gly
                325                 330                 335

Thr Pro Gln Pro Gly Gly Val Asp Val Val Gln Asn Leu Val Leu Gly
            340                 345                 350

Phe Ser Gly Gly Lys Phe Thr Ile Asn Gly Val Ala Phe Ser Pro Pro
            355                 360                 365

Thr Val Pro Val Leu Leu Gln Ile Leu Ser Gly Thr Thr Thr Ala Gln
            370                 375                 380

Asp Leu Leu Pro Thr Gly Ser Ile Ile Glu Leu Pro Leu Gly Lys Thr
385                 390                 395                 400

Val Glu Leu Thr Leu Ala Ala Gly Val Leu Gly Gly Pro His Pro Phe
                405                 410                 415

His Leu His Gly His Thr Phe His Val Val Arg Ser Ala Gly Gln Thr
            420                 425                 430

Thr Pro Asn Tyr Val Asp Pro Ile Leu Arg Asp Thr Val Asn Thr Gly
            435                 440                 445

Ala Ala Gly Asp Asn Val Thr Ile Arg Phe Thr Thr Asp Asn Pro Gly
450                 455                 460

Pro Trp Phe Leu His Cys His Ile Asp Trp His Leu Glu Ala Gly Phe
465                 470                 475                 480

Ala Val Val Phe Ala Glu Gly Leu Asn Gln Thr Asn Ala Ala Asn Pro
                485                 490                 495

Thr Pro Asp Ala Trp Asn Asn Leu Cys Asp Leu Tyr Asn Ala Leu Pro
            500                 505                 510
```

Ala Gly Asp Gln
        515

<210> SEQ ID NO 10
<211> LENGTH: 521
<212> TYPE: PRT
<213> ORGANISM: Lentinus sp

<400> SEQUENCE: 10

Met Ala Lys Phe Gln Ser Leu Leu Ser Tyr Thr Leu Ser Leu Val
1               5                   10                  15

Ala Thr Val Tyr Ala Gly Ile Gly Pro Ile Ala Ser Leu Val Val Thr
            20                  25                  30

Asp Ala Gln Ile Ser Pro Asp Gly Tyr Leu Arg Asp Ala Ile Val Thr
            35                  40                  45

Asn Gly Val Phe Pro Ala Pro Leu Ile Thr Gly Arg Lys Gly Asp His
        50                  55                  60

Phe Gln Leu Asn Val Val Asp Ser Met Thr Asn His Thr Met Leu Lys
65                  70                  75                  80

Ser Thr Ser Ile His Trp His Gly Phe Phe Gln Lys Gly Thr Asn Trp
                85                  90                  95

Ala Asp Gly Pro Ala Phe Val Asn Gln Cys Pro Ile Ser Ser Gly His
            100                 105                 110

Ser Phe Leu Tyr Asp Phe His Val Pro Asp Gln Ala Gly Thr Phe Trp
            115                 120                 125

Tyr His Ser His Leu Ser Thr Gln Tyr Cys Asp Gly Leu Arg Gly Pro
            130                 135                 140

Met Val Val Tyr Asp Pro Asn Asp Pro His Ala Asn Leu Tyr Asp Ile
145                 150                 155                 160

Asp Asn Asp Ser Thr Val Ile Thr Leu Ala Asp Trp Tyr His Val Ala
                165                 170                 175

Ala Lys Leu Gly Pro Arg Phe Pro Leu Gly Ala Asp Ala Thr Leu Ile
            180                 185                 190

Asn Gly Lys Gly Arg Ser Pro Ala Thr Pro Thr Ala Ala Leu Ser Val
            195                 200                 205

Ile Asn Val Val Lys Gly Lys Arg Tyr Arg Phe Arg Leu Val Ser Ile
        210                 215                 220

Ser Cys Asp Pro Asn Tyr Val Phe Ser Ile Asp Asn His Thr Met Thr
225                 230                 235                 240

Val Ile Glu Ala Asp Thr Val Asn Thr Gln Pro Leu Ala Val Asp Ser
                245                 250                 255

Ile Gln Ile Phe Ala Ala Gln Arg Tyr Ser Phe Ile Leu Asn Ala Asn
            260                 265                 270

Gln Pro Val Asp Asn Tyr Trp Ile Arg Ala Asn Pro Asn Phe Gly Asn
            275                 280                 285

Val Gly Phe Thr Asp Gly Ile Asn Ser Ala Ile Leu Arg Tyr Thr Gly
            290                 295                 300

Ala Ala Leu Val Glu Pro Ser Ala Thr Ala Pro Thr Leu Ser Asn
305                 310                 315                 320

Pro Leu Val Glu Thr Asn Leu His Pro Leu Ala Pro Met Pro Val Pro
                325                 330                 335

Gly Gln Pro Val Ser Gly Gly Val Asp Lys Ala Ile Asn Phe Ala Phe
            340                 345                 350

Asn Phe Asp Gly Thr Asp Phe Phe Ile Asn Gly Ala Ser Phe Val Pro
            355                 360                 365

-continued

```
Pro Thr Val Pro Val Leu Leu Gln Ile Met Ser Gly Ala Ser Thr Ala
    370                 375                 380

Gln Asp Leu Leu Pro Ser Gly Ser Val Tyr Pro Leu Pro Ser Asn Ala
385                 390                 395                 400

Thr Ile Glu Leu Ser Phe Pro Ala Thr Ala Ala Pro Gly Ala Pro
            405                 410                 415

His Pro Phe His Leu His Gly His Val Phe Ala Val Val Arg Ser Ala
                420                 425                 430

Gly Ser Thr Thr Tyr Asn Tyr Asn Asn Pro Ile Trp Arg Asp Val Val
            435                 440                 445

Ser Thr Gly Thr Pro Ala Ala Gly Asp Asn Val Thr Ile Arg Phe Ser
    450                 455                 460

Thr Asn Asn Pro Gly Pro Trp Phe Leu His Cys His Ile Asp Phe His
465                 470                 475                 480

Leu Glu Ala Gly Phe Ala Val Val Met Ala Glu Asp Val Pro Asp Ile
                485                 490                 495

Pro Ser Ala Asn Pro Val Pro Gln Ala Trp Ser Asn Leu Cys Pro Thr
            500                 505                 510

Tyr Asn Ala Leu Ser Ser Asp Asp Gln
            515                 520

<210> SEQ ID NO 11
<211> LENGTH: 488
<212> TYPE: PRT
<213> ORGANISM: Lentinus sp

<400> SEQUENCE: 11

Met Ala Lys Phe Gln Ser Leu Leu Ser Tyr Thr Leu Leu Ser Leu Val
1               5                   10                  15

Ala Thr Val Tyr Ala Gly Ile Gly Pro Ile Ala Ser Leu Val Val Thr
            20                  25                  30

Asp Ala Gln Ile Ser Pro Asp Gly Tyr Leu Arg Asp Ala Ile Val Thr
        35                  40                  45

Asn Gly Val Phe Pro Ala Pro Leu Ile Thr Gly Arg Lys Gly Asp His
    50                  55                  60

Phe Gln Leu Asn Val Val Asp Ser Met Thr Asn His Thr Met Leu Lys
65                  70                  75                  80

Ser Thr Ser Ile His Trp His Gly Phe Phe Gln Lys Gly Thr Asn Trp
                85                  90                  95

Ala Asp Gly Pro Ala Phe Val Asn Gln Cys Pro Ile Ser Ser Gly His
            100                 105                 110

Ser Phe Leu Tyr Asp Phe His Val Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Met Val Val Tyr Asp Pro Asn Asp Pro His Ala Asn Leu Tyr Asp Ile
145                 150                 155                 160

Asp Asn Asp Ser Thr Val Ile Thr Leu Ala Asp Trp Tyr His Val Ala
                165                 170                 175

Ala Lys Leu Gly Pro Arg Phe Pro Leu Gly Ala Asp Ala Thr Leu Ile
            180                 185                 190

Asn Gly Lys Gly Arg Ser Pro Ala Thr Pro Thr Ala Ala Leu Ser Val
        195                 200                 205

Ile Asn Val Val Lys Gly Lys Arg Tyr Arg Phe Arg Leu Val Ser Ile
    210                 215                 220
```

```
Ser Cys Asp Pro Asn Tyr Val Phe Ser Ile Asp Asn His Thr Met Thr
225                 230                 235                 240

Val Ile Glu Ala Asp Thr Val Asn Thr Gln Pro Leu Ala Val Asp Ser
            245                 250                 255

Ile Gln Ile Phe Ala Ala Gln Arg Tyr Ser Phe Ile Leu Asn Ala Asn
        260                 265                 270

Gln Pro Val Asp Asn Tyr Trp Ile Arg Ala Asn Pro Asn Phe Gly Asn
    275                 280                 285

Val Gly Phe Thr Asp Gly Ile Asn Ser Ala Ile Leu Arg Tyr Thr Gly
290                 295                 300

Ala Ala Leu Val Glu Pro Ser Ala Thr Thr Ala Pro Thr Leu Ser Asn
305                 310                 315                 320

Pro Leu Val Glu Thr Asn Leu His Pro Leu Ala Pro Met Pro Val Pro
            325                 330                 335

Gly Gln Pro Val Ser Gly Gly Val Asp Lys Ala Ile Asn Phe Ala Phe
        340                 345                 350

Asn Phe Asp Gly Thr Asp Phe Phe Ile Asn Gly Ala Ser Phe Val Pro
    355                 360                 365

Pro Thr Val Pro Val Leu Leu Gln Ile Met Ser Gly Ala Ser Thr Ala
370                 375                 380

Gln Asp Leu Leu Pro Ser Gly Ser Val Tyr Pro Leu Pro Ser Asn Ala
385                 390                 395                 400

Thr Ile Glu Leu Ser Phe Pro Ala Thr Ala Ala Pro Gly Ala Pro
            405                 410                 415

His Pro Phe His Leu His Gly His Val Phe Ala Val Val Arg Ser Ala
        420                 425                 430

Gly Ser Thr Thr Tyr Asn Tyr Asn Asn Pro Ile Trp Arg Asp Val Val
    435                 440                 445

Ser Thr Gly Thr Pro Ala Ala Gly Asp Asn Val Thr Ile Arg Phe Ser
450                 455                 460

Thr Asn Asn Pro Gly Pro Trp Phe Leu His Cys His Ile Asp Phe His
465                 470                 475                 480

Leu Glu Ala Gly Phe Ala Val Val
                485

<210> SEQ ID NO 12
<211> LENGTH: 521
<212> TYPE: PRT
<213> ORGANISM: Lentinus sp

<400> SEQUENCE: 12

Met Ala Lys Phe Gln Ser Leu Leu Ser Tyr Thr Val Leu Ser Phe Val
1               5                   10                  15

Ala Ala Ala Tyr Ala Ala Ile Gly Pro Val Ala Asp Leu Thr Ile Ser
            20                  25                  30

Asn Ala Gln Val Ser Pro Asp Gly Phe Leu Arg Asp Ala Val Val Thr
        35                  40                  45

Asn Gly Leu Val Pro Gly Pro Leu Ile Thr Gly Asn Lys Gly Asp Arg
    50                  55                  60

Phe Gln Leu Asn Val Ile Asp Gln Met Thr Asn His Thr Met Leu Lys
65                  70                  75                  80

Thr Thr Ser Ile His Trp His Gly Phe Phe Gln Lys Gly Thr Asn Trp
                85                  90                  95

Ala Asp Gly Pro Ala Phe Val Asn Gln Cys Pro Ile Ala Ser Gly Asn
            100                 105                 110
```

```
Ser Phe Leu Tyr Asp Phe Gln Val Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Leu Val Val Tyr Asp Pro Asn Asp Pro His Ala Ala Leu Tyr Asp Ile
145                 150                 155                 160

Asp Asp Asp Asn Thr Val Ile Thr Leu Thr Asp Trp Tyr His Thr Ala
                165                 170                 175

Ala Arg Leu Gly Pro Arg Phe Pro Leu Gly Ala Asp Ala Thr Leu Ile
            180                 185                 190

Asn Gly Leu Gly Arg Ser Pro Ala Thr Pro Thr Ala Asn Leu Thr Val
        195                 200                 205

Ile Asn Val Thr Gln Gly Lys Arg Tyr Arg Phe Arg Leu Val Ser Ile
210                 215                 220

Ser Cys Asp Pro Asn Tyr Val Phe Ser Ile Asp Asn His Thr Met Ser
225                 230                 235                 240

Val Ile Glu Thr Asp Thr Val Asn Thr Gln Pro Leu Thr Val Asp Ser
                245                 250                 255

Ile Gln Ile Tyr Ala Ala Gln Arg Tyr Ser Phe Val Leu Thr Ala Asn
            260                 265                 270

Gln Ser Val Asp Asn Tyr Trp Ile Arg Ala Asn Pro Asn Phe Gly Asn
        275                 280                 285

Val Gly Phe Thr Asp Ala Ile Asn Ser Ala Ile Leu Arg Tyr Asp Gly
290                 295                 300

Ala Pro Asp Ala Glu Pro Ser Ala Thr Thr Ala Pro Thr Leu Thr Asn
305                 310                 315                 320

Pro Leu Val Glu Ala Asn Leu His Pro Leu Ala Ser Met Pro Val Pro
                325                 330                 335

Gly Ser Pro Val Ser Gly Gly Val Asp Lys Ala Ile Asn Phe Val Phe
            340                 345                 350

Asn Phe Asn Gly Thr Asn Phe Ser Ile Asn Asn Ala Thr Phe Val Pro
        355                 360                 365

Pro Thr Val Pro Val Leu Leu Gln Ile Met Ser Gly Ala Asn Thr Ala
370                 375                 380

Gln Asp Leu Leu Pro Ser Gly Ser Val Tyr Thr Leu Pro Ser Asn Ala
385                 390                 395                 400

Thr Ile Glu Leu Ser Phe Pro Ala Thr Ser Asn Ala Pro Gly Ala Pro
                405                 410                 415

His Pro Phe His Leu His Gly His Val Phe Ala Val Val Arg Ser Ala
            420                 425                 430

Gly Ser Thr Val Tyr Asn Tyr Asp Asn Pro Ile Trp Arg Asp Val Val
        435                 440                 445

Ser Thr Gly Thr Pro Ala Ala Gly Asp Asn Val Thr Ile Arg Phe Gln
450                 455                 460

Thr Asn Asn Pro Gly Pro Trp Phe Leu His Cys His Ile Asp Phe His
465                 470                 475                 480

Leu Asp Ala Gly Phe Ala Val Val Met Ala Glu Asp Pro Val Asp Thr
                485                 490                 495

Pro Thr Ala Asp Pro Val Pro Gln Ala Trp Ser Asp Leu Cys Pro Thr
            500                 505                 510

Tyr Asp Ala Leu Ser Val Asp Asp Gln
        515                 520

<210> SEQ ID NO 13
```

<211> LENGTH: 1494
<212> TYPE: DNA
<213> ORGANISM: Cerrena sp

<400> SEQUENCE: 13

| | | | | | |
|---|---|---|---|---|---|
| gctatcggtc | ctgtcactga | cttagaaatc | acgaacggca | ccatctctcc | cgatggctat | 60 |
| tctcgtgcag | ccgtccttgc | tggaggctct | ttccccggcc | cacttatcac | aggaaacaaa | 120 |
| agtgacaact | tccaaatcaa | cgttgtgaac | tcgttggccg | attccgacat | gcttaagtct | 180 |
| acaaccgttc | actggcacgg | tttcttccaa | aagggtacca | actgggctga | cggccctgct | 240 |
| ttcgtcaacc | agtgtcccat | tgcgacgggc | aactcttttcc | tttacaactt | caacgctacg | 300 |
| gaccaggctg | gtactttctg | gtaccattct | cacttggaga | ctcagtactg | tgatggtctt | 360 |
| cgtggcccga | tggttgtcta | tgacccagac | gatcctcatg | ctgacctcta | cgatgtcgac | 420 |
| gacgatagca | ctgtcattac | tcttgccgat | tggtatcaca | cccttgctcg | acttggtgcc | 480 |
| gctttcccga | cttcggacgc | tactttgatc | aacggtttgg | gccgttacag | cgatggtaac | 540 |
| acaaccgatc | tcgctgtcat | tactgtcgaa | tccggcaaga | ggtaccgatt | caggctggtc | 600 |
| agcatttctt | gcgatcccaa | cttcactttc | tccatcgaca | accacaccat | gacaatcatc | 660 |
| gaggctgatg | ctgtcaacta | tacccctc | gatgttgacg | agattcaaat | cttcgctggt | 720 |
| caacgttact | ccttcattct | cactgccaac | cagaccgtcg | acaactactg | gattcgtgct | 780 |
| gaccccaacg | ttggtacgac | tggcttcgac | aatggcatca | actccgctat | ccttcgttac | 840 |
| agcggtgccg | acgaggtcga | gcctaccacc | aaccagacca | ccagtactaa | ccctcttgtt | 900 |
| gaggctaact | tggttcctct | cgatggtgct | gctgctcccg | gtgaagctgt | cgctggaggt | 960 |
| gttgactatg | cgctgaactt | ggctctcgct | ttcgacggta | caaacctcga | tttcaccgtc | 1020 |
| aacggttacg | agtacacctc | tcctaccgtc | ccagtcctac | tccaaattct | cagcggtgcc | 1080 |
| tcttccgtcg | acgacttgct | ccccagtgga | agcatttact | cactgccaag | caactccact | 1140 |
| atcgagctca | gtattcccgc | acttgccgtc | ggtgctcccc | accctatcca | tttgcacggt | 1200 |
| cacactttct | ctgtcgttcg | tagtgccgga | tccaccacct | acaactacga | caaccccctt | 1260 |
| cgtcgtgacg | tcgtcagcat | tggtaccgcc | actgatgata | acgttaccat | tcgtttcacc | 1320 |
| accgacaacc | cgggaccttg | gttcctccac | tgtcacattg | acttccactt | ggaagctggt | 1380 |
| ttcgcagtcg | tctttgctga | agactttaat | gacactgctt | ctgctaacac | tgtcaccact | 1440 |
| gaatggagcg | acctctgcac | tacctacgat | gccctctcct | ccgatgacct | ctaa | 1494 |

<210> SEQ ID NO 14
<211> LENGTH: 1491
<212> TYPE: DNA
<213> ORGANISM: Cerrena sp

<400> SEQUENCE: 14

| | | | | | |
|---|---|---|---|---|---|
| gctatcggtc | ccgtcactga | cctcacaatc | actaatgcca | ccatttcccc | ggatggtttc | 60 |
| tctcgtcaag | ccgtgcttgc | tggaggtgtt | ttccctggtc | cgcttattac | cggaaacaag | 120 |
| ggcgacaact | tccaaatcaa | tgttgttaat | tcattggaaa | actctgacat | gcttaagtct | 180 |
| acgaccattc | actggcacgg | tttcttccag | aagggtacca | actgggccga | tggtcctgcc | 240 |
| ttcgttaacc | aatgccccat | cgccacgggc | aactcttttcc | tgtacaactt | caacgcagac | 300 |
| gaccaggctg | gtacattctg | gtaccactct | cacttgtcta | ctcaatattg | cgatggtctc | 360 |
| cgaggcccta | tggtcgtcta | cgacccgaac | gatcctcacg | cttccctcta | cgatgttgat | 420 |
| gatgagagca | ctgtgattac | cctcgccgat | tggtaccaca | cccttgcccg | acttggtgca | 480 |

```
gctttcccga ctgcggatgc taccctcatt aacggcttgg gtcgttacag cgatggtact       540
acttcggacc ttgctgttat caccgttgag tccggaaaga ggtaccgatt ccgattggtc       600
aacatttctt gcgaccccaa ctacactttc tctatcgaca accacacatt caccgtcatt       660
gaggtcgatg tgtcaacca cgcggcgctt gatgtcgatg aaatccagat cttcgctggt       720
caacgttact cctttgttct cactgctaac caaaccgtcg acaactactg gatccgtgca       780
aaccccaatc tcgaaccac cggcttcgac aacggcatca actccgctat cctccgttac       840
agcggtgcta acgagactga acccaccacc acccagacca ccgctactgc tgctctcagc       900
gaagctagcc tcgttcctct cgaggaccct gctgctcctg gtgaggccgt tgccggaggt       960
gtcgattatg ctttgaactt ggcattcgcc ttcgacggtg ccaaccttga cttcacagtc      1020
aacggtgaaa cctacgtctc ccctaccgtc cccgtcctcc tccaaattct tagcggtgct      1080
tcctccgtct ctgacttgct ccctgccgga agcgtctact ccttgcccag caactccacc      1140
atcgagctca gcatgcctgg aggtgtcgtc ggtggtggtc accccttca cttgcacggt      1200 cacgccttct ccgttgttcg tagtgccggc tctgacactt acaactacgt caaccccct       1260 cgccgtgatg ttgtcaacat tggtgctgct ggtgacaacg tcactatccg tttcaccact      1320 gacaacccg gaccctggtt cctccactgc cacatcgatt tccacttgga agctggcttc      1380
gctgtcgtct ttgctgagga cttcaacgcc accgcttctt ctaacaccgt caccactgag      1440
tggagcaacc tttgcaccac ctacgacgcc ctctctgccg acgatcagta a              1491

<210> SEQ ID NO 15
<211> LENGTH: 1488
<212> TYPE: DNA
<213> ORGANISM: Cerrena sp

<400> SEQUENCE: 15
gctatcggtc ctgttgctga ccttcacatc acgatgcga acgtttctcc tgatggcttc        60
actcgacctg ctgtccttgc tggtggcacc ttccccggcc ctctcattac gggaaagcag       120
ggtgacaact tccagatcaa tgtcatcgac gaactcacgg acgcgactat gttgaagtct       180
acgtctattc attggcacgg tatcttccag aaaggcacca ctgggctga cggcccctcc       240 ttcgtcaatc agtgccccat cactacagga aactcgttcc tgtacgactt ttctgtcccc       300
gaccagaccg gcacgtactg gtatcacagt catttatcca cccagtactg tgacggtttg       360
cgaggagccc ttgtcattta cgacgacaat gatcctcaca aggatctcta tgatgttgat       420
gatgagacta ccgtcatcac cctcgccgac tggtatcata cccaggctcg cctgatcact      480
ggtgtccctg tctccgatgc gactctgatc aacggtcttg gccgttatct taatggccca      540
accgatgctc cgctcgctgt tatcactgtc gaccaaggaa aacgttatcg tttccgtctc      600
gtctctattt catgcgaccc gaacttcgtc ttctccattg acaaccattc catgactgtc      660
attgaagtcg atgctgtcaa cagccagcct ctcgtcgtcg actctattca aatcttcgcg      720
gcacagcgat actccttcat tttgaatgcc aaccaaagtg tcggaaacta ctggatccgt      780 gccaaccca cttgggcaa cactggtttt acgaatggca ttaactcggc cattcttcgg       840
tacaatggtg ctcctgttgc tgagcccaac accacccaaa ctgctagcac caacccttg       900 aacgaggtta accttcaccc tctagttccc acgcccgtcc ctggtactcc tcagcctggc       960
ggtgttgatg ttgtccagaa ccttgtcctc ggtttcagcg gcggcaagtt cactatcaac      1020
ggtgttgcct tttctccccc gacggtccca gttctccttc aaatccttag cggtactact      1080
actgcccaag atcttcttcc cactggatcc attatcgagc ttccctcgg aaagactgtt       1140
```

```
gaacttaccc tggcagcggg cgttctcggt ggtccccacc ccttccactt gcacggtcac    1200
actttccacg ttgttcgcag cgctggtcag actactccta actacgtcga tcctattctt    1260
cgtgacactg tcaacaccgg tgctgctggc gacaatgtta ctatccgttt caccactgac    1320
aaccctggac cctggttcct ccactgccac attgattggc acttggaagc cggtttcgct    1380
gttgtcttcg ctgaaggtct taaccagacc aatgctgcta accccactcc tgatgcttgg    1440
aacaaccttt gcgacctcta caatgccctt cctgctggtg accagtag                 1488

<210> SEQ ID NO 16
<211> LENGTH: 1503
<212> TYPE: DNA
<213> ORGANISM: Lentinus sp

<400> SEQUENCE: 16
ggcatcggcc ccattgctag cctcgtcgtc accgatgccc agattagccc cgacggctac      60
ttgcgcgatg ctatcgtgac caatggggtc ttcccagccc ctctgatcac tggacgtaag    120
ggtgatcact ccagctgaa tgtcgtggat tccatgacaa accacaccat gctgaaatcc     180
acaagtatcc actggcatgg cttcttccag aagggcacaa actgggctga tggtcctgca    240
tttgtgaacc agtgccctat ttccagcggc cactcgttcc tctacgactt ccacgttccg    300
gaccaagcag ggacgttctg gtaccacagt cacttgtcca ctcaatactg cgacggtttg    360
aggggcccga tggttgtgta cgatcccaac gaccctcatg caaatctcta cgacatcgat    420
aacgacagca ctgtgataac tctcgccgat tggtatcacg tcgcggccaa gctcggccct    480
cgcttcccac ttggggctga tgctacccct atcaacggaa agggcagaag ccctgccact    540
cccacagcag cactgtccgt catcaacgtg gtcaaaggca gcggtatcg gttccgcttg     600 gtttcaatct cctgcgaccc gaactatgtg ttcagcatcg acaaccatac gatgacggtc    660
atcgaggccg ataccgtgaa cacccagccc ctcgccgtcg acagcatcca gatcttcgcg    720
gcccagcgtt actcattcat tctcaacgcc aaccagcccg tcgacaacta ctggattcgc    780
gccaacccga acttcgggaa cgtcggattt acggatggca tcaactctgc tatcctccgt    840
tacactgggg cggcactggt cgaaccgtct gcgaccaccg ctccgacact gagcaaccct    900
ctcgtcgaga caaacctgca tcctcttgcg cccatgcctg tgcccggaca acccgtttcc    960
ggtggtgtcg ataaggctat caacttcgcc ttcaacttcg atggcacgga cttcttcatc    1020
aacggcgcga gcttcgtccc acctacggtt ccggtccttc tccaaatcat gagcggcgcc    1080
agcacggcgc aggacctcct tccttccggc agcgtctacc cgcttccatc aaacgcgacg    1140
atcgagctct ccttcccggc gaccgccgct gcgcctggcg ccccccaccc cttccacttg    1200
cacggccacg tcttcgccgt cgtccgcagc gcgggaagca ccacctacaa ttacaacaac    1260
cccatctggc gcgatgtcgt cagcactggc accccctgcag cgggcgacaa cgtcaccatc    1320 cgttttttcga cgaacaaccc gggtccgtgg ttcctccact gccacatcga cttccacctc    1380
gaggcgggct tcgcagtagt catggccgaa gacgtccccg acattccgtc tgcgaaccct    1440
gtgccccagg cgtggtcgaa cctttgccca acttacaacg cgctcagttc tgatgatcag    1500
taa                                                                  1503

<210> SEQ ID NO 17
<211> LENGTH: 1404
<212> TYPE: DNA
<213> ORGANISM: Lentinus sp

<400> SEQUENCE: 17
```

```
ggcatcggcc ccattgctag cctcgtcgtc accgatgccc agattagccc cgacggctac      60
ttgcgcgatg ctatcgtgac caatggggtc ttcccagccc ctctgatcac tggacgtaag     120
ggtgatcact ccagctgaa tgtcgtggat ccatgacaa accacaccat gctgaaatcc      180
acaagtatcc actggcatgg cttcttccag aagggcacaa actgggctga tggtcctgca     240
tttgtgaacc agtgccctat ttccagcggc cactcgttcc tctacgactt ccacgttccg     300
gaccaagcag ggacgttctg gtaccacagt cacttgtcca ctcaatactg cgacggtttg     360
aggggcccga tggttgtgta cgatcccaac gaccctcatg caaatctcta cgacatcgat     420
aacgacagca ctgtgataac tctcgccgat tggtatcacg tcgcggccaa gctcggccct     480
cgcttcccac ttggggctga tgctacccct atcaacggaa agggcagaag ccctgccact     540
cccacagcag cactgtccgt catcaacgtg gtcaaaggca agcggtatcg gttccgcttg     600
gtttcaatct cctgcgaccc gaactatgtg ttcagcatcg acaaccatac gatgacggtc     660
atcgaggccg ataccgtgaa cacccagccc ctcgccgtcg acagcatcca gatcttcgcg     720
gcccagcgtt actcattcat tctcaacgcc aaccagcccg tcgacaacta ctggattcgc     780
gccaacccga acttcgggaa cgtcggattt acggatggca tcaactctgc tatcctccgt     840
tacactgggg cggcactggt cgaaccgtct gcgaccaccg ctccgacact gagcaaccct     900
ctcgtcgaga caaacctgca tcctcttgcg cccatgcctg tgcccggaca cccgttccc     960 ggtggtgtcg ataaggctat caacttcgcc ttcaacttcg atggcacgga cttcttcatc    1020
aacggcgcga gcttcgtccc acctacggtt ccggtccttc tccaaatcat gagcggcgcc    1080
agcacggcgc aggacctcct tccttccggc agcgtctacc cgcttccatc aaacgcgacg    1140
atcgagctct ccttcccggc gaccgccgct gcgcctggcg ccccccaccc cttccacttg    1200
cacggccacg tcttcgccgt cgtccgcagc gcgggaagca ccacctacaa ttacaacaac    1260
cccatctggc gcgatgtcgt cagcactggc acccctgcag cgggcgacaa cgtcaccatc    1320 cgttttcga cgaacaaccc gggtccgtgg ttcctccact gccacatcga cttccacctc    1380
gaggcgggct cgcagtagt ctag                                              1404
```

<210> SEQ ID NO 18
<211> LENGTH: 1503
<212> TYPE: DNA
<213> ORGANISM: Lentinus sp

<400> SEQUENCE: 18

```
gccatcggcc cagtcgctga ccttaccatc agcaatgccc aagtcagccc cgacggcttc     60
ctccgcgatg ccgtcgtgac caacggcctg gtccctgggc cctcatcac gggcaacaag     120 ggcgatcgct ccagttgaa tgtcattgat caaatgacca accacacgat gttgaagact     180
acgagcattc actggcacgg cttcttccag aagggcacca actgggctga tggacctgcg     240
tttgtgaacc agtgccccat tgccagcggc aactccttcc tctacgactt ccaggtccct     300
gaccaggctg gcaccttctg gtatcacagc cacctttcga cccagtactg cgacggtctc     360
cgggggcctc tcgttgtgta cgaccccaat gacccacacg ctgccctcta tgatatcgac     420
gatgataaca ccgttattac tttgactgac tggtaccata ctgcggccag gctcggacct     480
cgttccccgc tgggagcaga tgccactctc atcaacggcc tgggccgcag cccagccacg    540
ccgaccgcca acctaactgt catcaacgtt actcagggca agcgctaccg cttccgcctc    600
gtgtcgatct cttgcgaccc gaactatgtg ttcagcatcg acaaccacac gatgagcgtc     660
attgagacgg acactgtcaa cactcaaccg ctcacggtcg atagcattca gatctacgcc    720
```

-continued

```
gcccagcgct actcctttgt gctcaccgcc aaccagtccg tggataacta ctggatccgg      780
gcaaacccca acttcggtaa cgtcggcttc acgdatgcta tcaactcggc catcctccgc      840
tatgacggtg ctcccgacgc tgagccctcc gctaccactg caccgacgtt gaccaacccg      900
ctggttgagg cgaaccttca cccgcttgct tcgatgcccg tgcccggatc ccctgtgtct      960
ggcggtgtgg acaaggccat taacttcgtc ttcaacttca acggcacgaa cttctccatc     1020
aacaacgcga ctttcgttcc gcccaccgtt ccggtgctgc tccagatcat gagcggcgcc     1080
aacaccgccc aagacctcct gccctctggc agcgtgtaca cactcccgtc aacgctacc      1140 attgagctgt ccttccctgc gacgagcaac gccccggcg ctcctcaccc cttccacttg      1200
cacggtcacg tcttcgccgt tgtccgcagc gctggcagca ccgtctacaa ctacgacaac     1260
cccatctggc gcgacgtcgt cagcaccggc acccctgcag cgggcgacaa cgtcaccatc     1320
cgcttccaga ccaacaaccc tggtccctgg ttcctccact gtcacatcga cttccacctc     1380
gacgccggct tgccgtggt catggctgag accctgttg acactccgac ggcggatccc       1440
gttccccagg cgtggtccga tctctgcccg acatacgacg cgctttccgt cgacgaccag    1500
tga                                                                   1503
```

<210> SEQ ID NO 19
<211> LENGTH: 1557
<212> TYPE: DNA
<213> ORGANISM: Cerrena sp

<400> SEQUENCE: 19

```
atgcttaact ttaattcgct ttccaccttc gcagtccttg ctttgtcgat gcgcgcaaat       60
gccgctatcg gtcctgtcac tgacttagaa atcacgaacg gcaccatctc tcccgatggc      120
tattctcgtg cagccgtcct tgctggaggc tctttccccg gcccacttat cacaggaaac      180
aaaagtgaca acttccaaat caacgttgtg aactcgttgg ccgattccga catgcttaag      240
tctacaaccg ttcactggca cggtttcttc caaaagggta ccaactgggc tgacggccct      300
gctttcgtca ccagtgtcc cattgcgacg ggcaactctt ccttttacaa cttcaacgct      360
acggaccagg ctggtacttt ctggtaccat tctcacttgg agactcagta ctgtgatggt      420
cttcgtggcc cgatggttgt ctatgaccca gacgatcctc atgctgacct ctacgatgtc      480
gacgacgata gcactgtcat tactcttgcc gattggtatc acacccttgc tcgacttggt      540 gccgcttttcc cgacttcgga cgctactttg atcaacggtt gggccgttta cagcgatggt      600
aacacaaccg atctcgctgt cattactgtc gaatccggca agaggtaccg attcaggctg      660
gtcagcattt cttgcgatcc caacttcact ttctccatcg acaaccacac catgacaatc      720
atcgaggctg atgctgtcaa ctatacaccc ctcgatgttg acgagattca aatcttcgct      780
ggtcaacgtt actccttcat tctcactgcc aaccagaccg tcgacaacta ctggattcgt      840
gctgacccca acgttggtac gactggcttc gacaatggca tcaactccgc tatccttcgt      900
tacagcggtg ccgacgaggt cgagcctacc accaaccaga ccaccagtac taaccctctt      960
gttgaggcta acttggttcc tctcgatggt gctgctgctc ccggtgaagc tgtcgctgga     1020
ggtgttgact atgcgctgaa cttggctctc gctttcgacg gtacaaacct cgatttcacc     1080
gtcaacggtt acgagtacac ctctcctacc gtcccagtcc tactccaaat tctcagcggt     1140
gcctcttccg tcgacgactt gctccccagt ggaagcattt actcactgcc aagcaactcc     1200
actatcgagc tcagtattcc cgcacttgcc gtcggtgctc ccacccctat ccatttgcac     1260
ggtcacactt tctctgtcgt tcgtagtgcc ggatccacca cctacaacta cgacaacccc     1320
```

```
cctcgtcgtg acgtcgtcag cattggtacc gccactgatg ataacgttac cattcgtttc    1380
accaccgaca acccgggacc ttggttcctc cactgtcaca ttgacttcca cttggaagct    1440
ggtttcgcag tcgtctttgc tgaagacttt aatgacactg cttctgctaa cactgtcacc    1500
actgaatgga gcgacctctg cactacctac gatgccctct cctccgatga cctctaa      1557
```

<210> SEQ ID NO 20
<211> LENGTH: 1554
<212> TYPE: DNA
<213> ORGANISM: Cerrena sp

<400> SEQUENCE: 20

```
atgattaact ttaattcgtt acttactttc acagtcctag cactgtcgat gcgcgcacat     60
gccgctatcg gtcccgtcac tgacctcaca atcactaatg ccaccatttc cccggatggt    120
ttctctcgtc aagccgtgct tgctggaggt gtttttccctg gtccgcttat taccggaaac   180
aagggcgaca acttccaaat caatgttgtt aattcattgg aaaactctga catgcttaag    240
tctacgacca ttcactggca cggtttcttc cagaagggta ccaactgggc cgatggtcct    300
gccttcgtta accaatgccc catcgccacg ggcaactctt tcctgtacaa cttcaacgca    360
gacgaccagg ctggtacatt ctggtaccac tctcacttgt ctactcaata ttgcgatggt    420
ctccgaggcc ctatggtcgt ctacgacccg aacgatcctc acgcttccct ctacgatgtt    480
gatgatgaga gcactgtgat taccctcgcc gattggtacc acacccttgc ccgacttggt    540 gcagcttttcc cgactgcgga tgctaccctc attaacggct ggggtcgtta cagcgatggt    600
actacttcgg accttgctgt tatcaccgtt gagtccggaa agaggtaccg attccgattg    660
gtcaacattt cttgcgaccc caactacact ttctctatcg acaaccacac attcaccgtc    720
attgaggtcg atggtgtcaa ccacgcggcg cttgatgtcg atgaaatcca gatcttcgct    780
ggtcaacgtt actcctttgt tctcactgct aaccaaaccg tcgacaacta ctggatccgt    840
gcaaacccca atctcggaac caccggcttc gacaacggca tcaactccgc tatcctccgt    900
tacagcggtg ctaacgagac tgaacccacc accacccaga ccaccgctac tgctgctctc    960
agcgaagcta gcctcgttcc tctcgaggac cctgctgctc tggtgaggc cgttgccgga   1020 ggtgtcgatt atgctttgaa cttggcattc gccttcgacg tgccaacct tgacttcaca   1080 gtcaacggtg aaacctacgt ctcccctacc gtccccgtcc tcctccaaat tcttagcggt   1140
gcttcctccg tctctgactt gctccctgcc ggaagcgtct actccttgcc cagcaactcc   1200
accatcgagc tcagcatgcc tggaggtgtc gtcggtggtg tcaccccccct tcacttgcac   1260 ggtcacgcct ctccgttgt tcgtagtgcc ggctctgaca cttacaacta cgtcaacccc   1320
cctcgccgtg atgttgtcaa cattggtgct gctggtgaca acgtcactat ccgtttcacc   1380
actgacaacc ccgaccctg gttcctccac tgccacatcg atttccactt ggaagctggc   1440
ttcgctgtcg tctttgctga ggacttcaac gccaccgctt cttctaacac cgtcaccact   1500
gagtggagca acctttgcac cacctacgac gccctctctg ccgacgatca gtaa        1554
```

<210> SEQ ID NO 21
<211> LENGTH: 1551
<212> TYPE: DNA
<213> ORGANISM: Cerrena sp

<400> SEQUENCE: 21

```
atggccttcc gaaccggggtt ttccgctttc atctctctca gccttgccct tggtgcactc    60
gctgctatcg gtcctgttgc tgaccttcac atcacggatg cgaacgtttc tcctgatggc   120
```

-continued

```
ttcactcgac ctgctgtcct tgctggtggc accttccccg gccctctcat tacgggaaag      180
cagggtgaca acttccagat caatgtcatc gacgaactca cggacgcgac tatgttgaag      240
tctacgtcta ttcattggca cggtatcttc cagaaaggca ccaactgggc tgacggcccc      300
tccttcgtca atcagtgccc catcactaca ggaaactcgt tcctgtacga cttttctgtc      360
cccgaccaga ccggcacgta ctggtatcac agtcatttat ccacccagta ctgtgacggt      420
ttgcgaggag cccttgtcat ttacgacgac aatgatcctc acaaggatct ctatgatgtt      480
gatgatgaga ctaccgtcat caccctcgcc gactggtatc atacccaggc tcgcctgatc      540
actggtgtcc ctgtctccga tgcgactctg atcaacggtc ttggccgtta tcttaatggc      600
ccaaccgatg ctccgctcgc tgttatcact gtcgaccaag aaaacgtta tcgtttccgt       660
ctcgtctcta tttcatgcga cccgaacttc gtcttctcca ttgacaacca ttccatgact      720
gtcattgaag tcgatgctgt caacagccag cctctcgtcg tcgactctat tcaaatcttc      780
gcggcacagc gatactcctt cattttgaat gccaaccaaa gtgtcggaaa ctactggatc      840
cgtgccaacc ccaacttggg caacactggt ttacgaatg gcattaactc ggccattctt       900
cggtacaatg gtgctcctgt tgctgagccc aacaccaccc aaactgctag caccaacccc      960
ttgaacgagg ttaaccttca ccctctagtt cccacgcccg tccctggtac tcctcagcct     1020
ggcggtgttg atgttgtcca gaaccttgtc ctcggtttca gcggcggcaa gttcactatc     1080
aacggtgttg ccttttctcc cccgacggtc ccagttctcc ttcaaatcct tagcggtact     1140
actactgccc aagatcttct tcccactgga tccattatcg agcttcccct cggaaagact     1200
gttgaactta ccctggcagc gggcgttctc ggtggtcccc acccttcca cttgcacggt      1260
cacactttcc acgttgttcg cagcgctggt cagactactc ctaactacgt cgatcctatt     1320
cttcgtgaca ctgtcaacac cggtgctgct ggcgacaatg ttactatccg tttcaccact     1380
gacaaccctg acctggtt cctccactgc cacattgatt ggcacttgga agccggtttc       1440
gctgttgtct cgctgaagg tcttaaccag accaatgctg ctaaccccac tcctgatgct     1500
tggaacaacc tttgcgacct ctacaatgcc cttcctgctg gtgaccagta g             1551
```

<210> SEQ ID NO 22
<211> LENGTH: 1566
<212> TYPE: DNA
<213> ORGANISM: Lentinus sp

<400> SEQUENCE: 22

```
atggccaagt tcagtctttt gctctcctac acccttctct ccctcgtcgc cactgtctat       60
gcaggcatcg gccccattgc tagcctcgtc gtcaccgatg cccagattag ccccgacggc      120
tacttgcgcg atgctatcgt gaccaatggg gtcttcccag cccctctgat cactggacgt      180
aagggtgatc acttccagct gaatgtcgtg gattccatga caaaccacac catgctgaaa      240
tccacaagta tccactggca tggcttcttc cagaagggca caaactgggc tgatggtcct      300
gcatttgtga accagtgccc tatttccagc ggccactcgt tcctctacga cttccacgtt      360
ccggaccaag cagggacgtt ctggtaccac agtcacttgt ccactcaata ctgcgacggt      420
ttgaggggcc cgatggttgt gtacgatccc aacgaccctc atgcaaatct ctacgacatc      480
gataacgaca gcactgtgat aactctcgcc gattggtatc acgtcgcggc caagctcggc      540
cctcgcttcc cacttggggc tgatgctacc cttatcaacg gaaagggcag aagccctgcc      600
actcccacag cagcactgtc cgtcatcaac gtggtcaaag gcaagcggta tcggttccgc      660
ttggttttcaa tctcctgcga cccgaactat gtgttcagca tcgacaacca tacgatgacg      720
```

```
gtcatcgagg ccgataccgt gaacacccag cccctcgccg tcgacagcat ccagatcttc      780
gcggcccagc gttactcatt cattctcaac gccaaccagc ccgtcgacaa ctactggatt      840
cgcgccaacc cgaacttcgg gaacgtcgga tttacggatg gcatcaactc tgctatcctc      900
cgttacactg gggcggcact ggtcgaaccg tctgcgacca ccgctccgac actgagcaac      960
cctctcgtcg agacaaacct gcatcctctt gcgcccatgc ctgtgcccgg acaacccgtt     1020
tccggtggtg tcgataaggc tatcaacttc gccttcaact tcgatggcac ggacttcttc     1080
atcaacggcg cgagcttcgt cccacctacg gttccggtcc ttctccaaat catgagcggc     1140
gccagcacgg cgcaggacct ccttccttcc ggcagcgtct acccgcttcc atcaaacgcg     1200
acgatcgagc tctccttccc ggcgaccgcc gctgcgcctg gcgcccccca ccccttccac     1260
ttgcacggcc acgtcttcgc cgtcgtccgc agcgcgggaa gcaccaccta caattacaac     1320
aaccccatct ggcgcgatgt cgtcagcact ggcacccctg cagcgggcga caacgtcacc     1380
atccgttttt cgacgaacaa cccgggtccg tggttcctcc actgccacat cgacttccac     1440
ctcgaggcgg gcttcgcagt agtcatggcc gaagacgtcc ccgacattcc gtctgcgaac     1500
cctgtgcccc aggcgtggtc gaacctttgc ccaacttaca acgcgctcag ttctgatgat     1560
cagtaa                                                                1566

<210> SEQ ID NO 23
<211> LENGTH: 1467
<212> TYPE: DNA
<213> ORGANISM: Lentinus sp

<400> SEQUENCE: 23
atggccaagt ttcagtcttt gctctcctac acccttctct ccctcgtcgc cactgtctat       60
gcaggcatcg gccccattgc tagcctcgtc gtcaccgatg cccagattag ccccgacggc      120
tacttgcgcg atgctatcgt gaccaatggg gtcttcccag cccctctgat cactggacgt      180
aagggtgatc acttccagct gaatgtcgtg gattccatga caaaccacac catgctgaaa      240
tccacaagta tccactggca tggcttcttc cagaagggca caaactgggc tgatggtcct      300
gcatttgtga accagtgccc tatttccagc ggccactcgt tcctctacga cttccacgtt      360
ccggaccaag cagggacgtt ctggtaccac agtcacttgt ccactcaata ctgcgacggt      420
ttgaggggcc cgatggttgt gtacgatccc aacgaccctc atgcaaatct ctacgacatc      480
gataacgaca gcactgtgat aactctcgcc gattggtatc acgtcgcggc caagctcggc      540
cctcgcttcc cacttggggc tgatgctacc cttatcaacg gaaagggcag aagccctgcc      600
actcccacag cagcactgtc cgtcatcaac gtggtcaaag gcaagcggta tcggttccgc      660
ttggtttcaa tctcctgcga cccgaactat gtgttcagca tcgacaacca tacgatgacg      720
gtcatcgagg ccgataccgt gaacacccag cccctcgccg tcgacagcat ccagatcttc      780
gcggcccagc gttactcatt cattctcaac gccaaccagc ccgtcgacaa ctactggatt      840
cgcgccaacc cgaacttcgg gaacgtcgga tttacggatg gcatcaactc tgctatcctc      900
cgttacactg gggcggcact ggtcgaaccg tctgcgacca ccgctccgac actgagcaac      960
cctctcgtcg agacaaacct gcatcctctt gcgcccatgc ctgtgcccgg acaacccgtt     1020
tccggtggtg tcgataaggc tatcaacttc gccttcaact tcgatggcac ggacttcttc     1080
atcaacggcg cgagcttcgt cccacctacg gttccggtcc ttctccaaat catgagcggc     1140
gccagcacgg cgcaggacct ccttccttcc ggcagcgtct acccgcttcc atcaaacgcg     1200
acgatcgagc tctccttccc ggcgaccgcc gctgcgcctg gcgcccccca ccccttccac     1260
```

```
ttgcacggcc acgtcttcgc cgtcgtccgc agcgcgggaa gcaccaccta caattacaac    1320
aaccccatct ggcgcgatgt cgtcagcact ggcaccsctg cagcgggcga caacgtcacc    1380
atccgttttt cgacgaacaa cccgggtccg tggttcctcc actgccacat cgacttccac    1440
ctcgaggcgg gcttcgcagt agtctag                                        1467

<210> SEQ ID NO 24
<211> LENGTH: 1566
<212> TYPE: DNA
<213> ORGANISM: Lentinus sp

<400> SEQUENCE: 24
atggccaagt ccagtcgtt gctttcttac actgtcctct ccttcgtcgc ggctgcctat      60
gctgccatcg gcccagtcgc tgaccttacc atcagcaatg cccaagtcag ccccgacggc    120
ttcctccgcg atgccgtcgt gaccaacggc ctggtccctg ggcccctcat cacgggcaac    180
aagggcgatc gcttccagtt gaatgtcatt gatcaaatga ccaaccacac gatgttgaag    240
actacgagca ttcactggca cggcttcttc cagaagggca ccaactgggc tgatggacct    300
gcgtttgtga accagtgccc cattgccagc ggcaactcct tcctctacga cttccaggtc    360
cctgaccagg ctggcaccct ctggtatcac agccaccttt cgacccagta ctgcgacggt    420
ctccgggggc ctctcgttgt gtacgacccc aatgacccac acgctgccct ctatgatatc    480
gacgatgata acaccgttat tactttgact gactggtacc atactgcggc caggctcgga    540 cctcgttttcc cgctgggagc agatgccact ctcatcaacg gcctgggccg cagcccagcc    600
acgccgaccg ccaacctaac tgtcatcaac gttactcagg gcaagcgcta ccgcttccgc    660
ctcgtgtcga tctcttgcga cccgaactat gtgttcagca tcgacaacca cacgatgagc    720
gtcattgaga cggacactgt caacactcaa ccgctcacgg tcgatagcat tcagatctac    780
gccgcccagc gctactcctt tgtgctcacc gccaaccagt ccgtggataa ctactggatc    840 cgggcaaaacc ccaacttcgg taacgtcggc ttcacggatg ctatcaactc ggccatcctc    900
cgctatgacg tgctcccga cgctgagccc tccgctacca ctgcaccgac gttgaccaac    960
ccgctggttg aggcgaacct tcacccgctt gcttcgatgc ccgtgcccgg atcccctgtg    1020
tctggcggtg tggacaaggc cattaacttc gtcttcaact tcaacggcac gaacttctcc    1080
atcaacaacg cgactttcgt tccgcccacc gttccggtgc tgctccagat catgagcggc    1140
gccaacaccg cccaagacct cctgccctct ggcagcgtgt acacactccc gtccaacgct    1200
accattgagc tgtccttccc tgcgacgagc aacgcccccg gcgctcctca cccttccac    1260 ttgcacggtc acgtcttcgc cgttgtccgc agcgctggca gcaccgtcta caactacgac    1320
aaccccatct ggcgcgacgt cgtcagcacc ggcaccsctg cagcgggcga caacgtcacc    1380
atccgcttcc agaccaacaa ccctggtccc tggttcctcc actgtcacat cgacttccac    1440
ctcgacgccg gctttgccgt ggtcatggct gaggaccstg ttgacactcc gacggcggat    1500
cccgttcccc aggcgtggtc cgatctctgc ccgacatacg acgcgctttc cgtcgacgac    1560
cagtga                                                               1566

<210> SEQ ID NO 25
<211> LENGTH: 19
<212> TYPE: DNA
<213> ORGANISM: Artificial sequence
<220> FEATURE:
<223> OTHER INFORMATION: Synthetic primer

<400> SEQUENCE: 25
```

```
gtagtcatat gcttgtctc                                              19

<210> SEQ ID NO 26
<211> LENGTH: 19
<212> TYPE: DNA
<213> ORGANISM: Artificial sequence
<220> FEATURE:
<223> OTHER INFORMATION: Synthetic primer

<400> SEQUENCE: 26
ccgcagcttc acctacgga                                              19

<210> SEQ ID NO 27
<211> LENGTH: 20
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (12)..(12)
<223> OTHER INFORMATION: n is a, c, g, or t

<400> SEQUENCE: 27
caytggcayg gnttyttyca                                             20

<210> SEQ ID NO 28
<211> LENGTH: 20
<212> TYPE: DNA
<213> ORGANISM: Artificial sequence
<220> FEATURE:
<223> OTHER INFORMATION: Synthetic primer

<400> SEQUENCE: 28
tgraartcda trtgrcartg                                             20

<210> SEQ ID NO 29
<211> LENGTH: 28
<212> TYPE: DNA
<213> ORGANISM: Artificial sequence
<220> FEATURE:
<223> OTHER INFORMATION: Synthetic primer

<400> SEQUENCE: 29
gcgacgtgat accaatcggc gagagtta                                    28

<210> SEQ ID NO 30
<211> LENGTH: 28
<212> TYPE: DNA
<213> ORGANISM: Artificial sequence
<220> FEATURE:
<223> OTHER INFORMATION: Synthetic primer

<400> SEQUENCE: 30
ccatgctgaa atccacaagt atccactg                                    28

<210> SEQ ID NO 31
<211> LENGTH: 28
<212> TYPE: DNA
<213> ORGANISM: Artificial sequence
<220> FEATURE:
<223> OTHER INFORMATION: Synthetic primer

<400> SEQUENCE: 31
cctaacctgc gcatcggctt cccccagc                                    28

<210> SEQ ID NO 32
```

```
<211> LENGTH: 30
<212> TYPE: DNA
<213> ORGANISM: Artificial sequence
<220> FEATURE:
<223> OTHER INFORMATION: Synthetic primer

<400> SEQUENCE: 32
cgcaaaaacc ctgcgtccgc attacccagc                                          30

<210> SEQ ID NO 33
<211> LENGTH: 25
<212> TYPE: DNA
<213> ORGANISM: Artificial sequence
<220> FEATURE:
<223> OTHER INFORMATION: Synthetic primer

<400> SEQUENCE: 33
ttcgaaacga ggaattccca ccatg                                               25

<210> SEQ ID NO 34
<211> LENGTH: 25
<212> TYPE: DNA
<213> ORGANISM: Artificial sequence
<220> FEATURE:
<223> OTHER INFORMATION: Synthetic primer

<400> SEQUENCE: 34
ttctagatcc tgatcatcag aactg                                               25
```